United States Patent
Leis et al.

(10) Patent No.: US 10,300,080 B2
(45) Date of Patent: May 28, 2019

(54) METHODS AND COMPOUNDS TO INHIBIT ENVELOPED VIRUS RELEASE

(71) Applicants: Northwestern University, Evanston, IL (US); The Research Foundation for The State University of New York, Albany, NY (US)

(72) Inventors: Jonathan Leis, Chicago, IL (US); Carol Carter, Huntington, NY (US)

(73) Assignees: Northwestern University, Evanston, IL (US); The Research Foundation for the State University, Albany, NY (US)

( * ) Notice: Subject to any disclaimer, the term of this patent is extended or adjusted under 35 U.S.C. 154(b) by 176 days.

(21) Appl. No.: 14/937,182

(22) Filed: Nov. 10, 2015

(65) Prior Publication Data

US 2017/0095485 A1    Apr. 6, 2017

Related U.S. Application Data

(62) Division of application No. 14/138,053, filed on Dec. 21, 2013, now abandoned.

(60) Provisional application No. 61/745,336, filed on Dec. 21, 2012.

(51) Int. Cl.
| | |
|---|---|
| *A61K 31/65* | (2006.01) |
| *A61K 31/165* | (2006.01) |
| *A61K 31/4035* | (2006.01) |
| *A61K 31/4439* | (2006.01) |
| *A61K 31/53* | (2006.01) |
| *A61K 31/415* | (2006.01) |
| *A61K 31/437* | (2006.01) |

(52) U.S. Cl.
CPC ............ *A61K 31/65* (2013.01); *A61K 31/165* (2013.01); *A61K 31/4035* (2013.01); *A61K 31/415* (2013.01); *A61K 31/437* (2013.01); *A61K 31/4439* (2013.01); *A61K 31/53* (2013.01)

(58) Field of Classification Search
CPC ..... A61K 31/165; A61K 31/65; A61K 31/437
See application file for complete search history.

(56) References Cited

U.S. PATENT DOCUMENTS

| | | | | |
|---|---|---|---|---|
| 2002/0077276 | A1* | 6/2002 | Fredeking | A61K 35/14 435/5 |
| 2011/0262442 | A1* | 10/2011 | Hamilton et al. | A61K 39/395 424/139.1 |

FOREIGN PATENT DOCUMENTS

WO    2005004921 A1    1/2005

OTHER PUBLICATIONS

Lo, MC, et al., "Evaluation of fluorescence-based thermal shift assays for hit identification in drug discovery," Anal Biochem. (2004) 332:153-159.

(Continued)

*Primary Examiner* — San Ming R Hui
(74) *Attorney, Agent, or Firm* — Andrus Intellectual Property Law, LLP

(57) ABSTRACT

A compound having an antiviral activity for inhibiting release of an enveloped virus from a cell is disclosed, including methods of inhibiting release of an enveloped virus from a cell. The antiviral activity of the compound includes inhibiting formation of an associative complex or disrupting formation of an associative complex. The associative complex comprises an L-domain motif of the enveloped virus and at least one cellular polypeptide, or fragment thereof, capable of binding the L-domain motif of the enveloped virus.

7 Claims, 12 Drawing Sheets

Specification includes a Sequence Listing.

(56) References Cited

OTHER PUBLICATIONS

Luan, Ch, et al., "Ligand screening using Fluorescence Thermal Shift Analysis (FTS)," Structural Genomics and Drug Discovery: Methods and Protocols, Methods Mol. Biol. 2013, Chapter 20, pp. 263-285 (W.F. Anderson, ed.) Humana Press.

Myoung, J., et al., "Generation of a doxycycline-inducible KSHV producer cell line of endothelial origin: maintenance of tight latency with efficient reactivation upon induction," J. Virol. Methods (2011) 174(1-2):12-21.

Pantoliano, MW, et al., "High-density miniaturized thermal shift assays as a general strategy for drug discovery," J. Biomol. Screen (2001) 6(6):429-440.

Vieira, J., et al., "Use of the red fluorescent protein as a marker of Kaposi's sarcoma-associated herpes virus lytic gene expression," Virology (2004) 325(2):225-40.

Zhang, J., et al., "Patterns of microRNA expression characterize stages of human B-cell differentiation," Blood (2009) 113(19):4586-4594.

\* cited by examiner

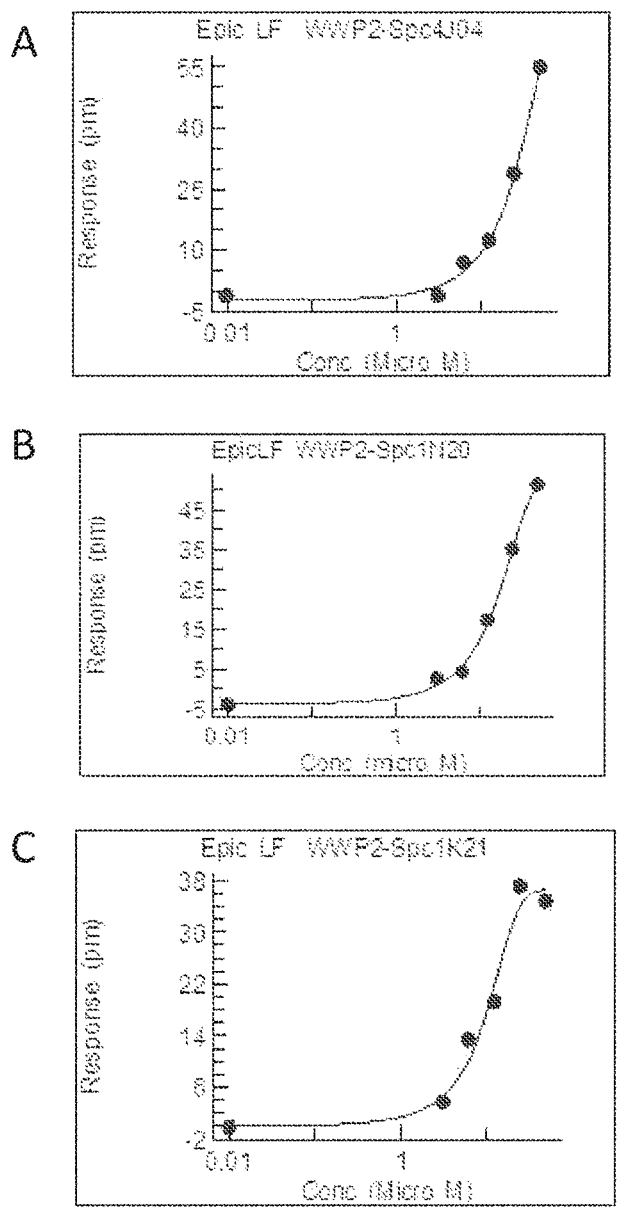
FIG. 5 A-C

SEQUENCE LISTING

```
<160> NUMBER OF SEQ ID NOS: 42

<210> SEQ ID NO 1
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 1

Ala Ala Pro Thr Ala Pro Pro Thr Gly Ala Ala Asp Ser Ile Pro Pro
1               5                   10                  15

Pro Tyr Ser Pro
            20

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Thr Ala Pro Ser Ser Pro Pro Pro Tyr Glu Glu
1               5                   10

<210> SEQ ID NO 3
<211> LENGTH: 17
<212> TYPE: PRT
<213> ORGANISM: Artificial Sequence
<220> FEATURE:
<223> OTHER INFORMATION: SYNTHETIC PEPTIDE
```

```
<400> SEQUENCE: 3

Met Arg Arg Val Ile Leu Pro Thr Ala Pro Pro Glu Tyr Met Glu Ala
1               5                   10                  15

Ile

<210> SEQ ID NO 4
<211> LENGTH: 16
<212> TYPE: PRT
<213> ORGANISM: Artificial Sequence
<220> FEATURE:
<223> OTHER INFORMATION: SYNTHETIC PEPTIDE

<400> SEQUENCE: 4

Asn Thr Tyr Met Gln Tyr Leu Asn Pro Pro Tyr Ala Asp His Ser
1               5                   10                  15

<210> SEQ ID NO 5
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 5

Pro Pro Ala Tyr
1

<210> SEQ ID NO 6
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 6

Pro Pro Thr Tyr
1

<210> SEQ ID NO 7
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 7

Pro Pro Pro Tyr
1

<210> SEQ ID NO 8
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 8

Pro Thr Ala Pro
1

<210> SEQ ID NO 9
<211> LENGTH: 14
<212> TYPE: PRT
<213> ORGANISM: Artificial Sequence
<220> FEATURE:
```

<223> OTHER INFORMATION: SYNTHETIC PEPTIDE

<400> SEQUENCE: 9

Gln Ser Ile Lys Ala Phe Pro Ile Val Ile Asn Ser Asp Gly
1               5                   10

<210> SEQ ID NO 10
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 10

Arg Leu Asn Ala Phe Pro Ile Val Met Gly Gln
1               5                   10

<210> SEQ ID NO 11
<211> LENGTH: 19
<212> TYPE: PRT
<213> ORGANISM: Artificial Sequence
<220> FEATURE:
<223> OTHER INFORMATION: SYNTHETIC PEPTIDE

<400> SEQUENCE: 11

Ala Thr Ala Ser Ala Pro Pro Pro Tyr Val Gly Ser Gly Leu Tyr
1               5                   10                  15

Pro Ser Leu

<210> SEQ ID NO 12
<211> LENGTH: 22
<212> TYPE: PRT
<213> ORGANISM: Artificial Sequence
<220> FEATURE:
<223> OTHER INFORMATION: SYNTHETIC PEPTIDE

<400> SEQUENCE: 12

Pro Glu Pro Thr Ala Pro Pro Phe Leu Gln Ser Arg Pro Glu Pro Thr
1               5                   10                  15

Ala Pro Pro Glu Glu Ser
            20

<210> SEQ ID NO 13
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 13

Asp Pro Gln Ile Pro Pro Pro Tyr Val Glu Pro Thr Ala Pro
1               5                   10

<210> SEQ ID NO 14
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 14

Gln Asn Leu Tyr Pro Asp Leu Ser Glu Ile Lys
1               5                   10

<210> SEQ ID NO 15

<211> LENGTH: 21
<212> TYPE: PRT
<213> ORGANISM: Artificial Sequence
<220> FEATURE:
<223> OTHER INFORMATION: SYNTHETIC PEPTIDE

<400> SEQUENCE: 15

Leu Gly Ile Ala Pro Pro Pro Tyr Glu Glu Asp Thr Ser Met Glu Tyr
1               5                   10                  15

Ala Pro Ser Ala Pro
            20

<210> SEQ ID NO 16
<211> LENGTH: 16
<212> TYPE: PRT
<213> ORGANISM: Artificial Sequence
<220> FEATURE:
<223> OTHER INFORMATION: SYNTHETIC PEPTIDE

<400> SEQUENCE: 16

Asp Asp Leu Trp Leu Pro Pro Pro Glu Tyr Val Pro Leu Lys Glu Leu
1               5                   10                  15

<210> SEQ ID NO 17
<211> LENGTH: 48
<212> TYPE: PRT
<213> ORGANISM: Artificial Sequence
<220> FEATURE:
<223> OTHER INFORMATION: SYNTHETIC PEPTIDE

<400> SEQUENCE: 17

Ala Thr Ala Ser Ala Pro Pro Pro Tyr Val Gly Ser Gly Gly Gly Ala
1               5                   10                  15

Thr Ala Ser Ala Pro Pro Pro Tyr Val Gly Ser Gly Gly Gly Ala Thr
            20                  25                  30

Ala Ser Ala Pro Pro Pro Tyr Val Gly Ser Gly Gly Gly Arg Arg Arg
        35                  40                  45

<210> SEQ ID NO 18
<211> LENGTH: 48
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MISC_FEATURE
<222> LOCATION: (1)..(1)
<223> OTHER INFORMATION: FITC-MODIFIED N-TERMINUS

<400> SEQUENCE: 18

Ala Thr Ala Ser Ala Pro Pro Pro Tyr Val Gly Ser Gly Gly Gly Ala
1               5                   10                  15

Thr Ala Ser Ala Pro Pro Pro Tyr Val Gly Ser Gly Gly Gly Ala Thr
            20                  25                  30

Ala Ser Ala Pro Pro Pro Tyr Val Gly Ser Gly Gly Gly Arg Arg Arg
        35                  40                  45

<210> SEQ ID NO 19
<211> LENGTH: 48
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MISC_FEATURE
<222> LOCATION: (1)..(1)

<223> OTHER INFORMATION: TAMRA-MODIFIED N-TERMINUS

<400> SEQUENCE: 19

Ala Thr Ala Ser Ala Pro Pro Tyr Val Gly Ser Gly Gly Gly Ala
1               5                   10                  15

Thr Ala Ser Ala Pro Pro Tyr Val Gly Ser Gly Gly Gly Ala Thr
            20                  25                  30

Ala Ser Ala Pro Pro Tyr Val Gly Ser Gly Gly Gly Arg Arg Arg
        35                  40                  45

<210> SEQ ID NO 20
<211> LENGTH: 36
<212> TYPE: PRT
<213> ORGANISM: Artificial Sequence
<220> FEATURE:
<223> OTHER INFORMATION: SYNTHETIC PEPTIDE

<400> SEQUENCE: 20

Arg Pro Gly Asn Phe Leu Gln Ser Arg Pro Glu Pro Thr Ala Pro Pro
1               5                   10                  15

Phe Leu Gln Ser Arg Pro Glu Pro Thr Ala Pro Pro Glu Glu Ser Phe
            20                  25                  30

Arg Arg Arg Arg
        35

<210> SEQ ID NO 21
<211> LENGTH: 36
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MISC_FEATURE
<222> LOCATION: (1)..(1)
<223> OTHER INFORMATION: FITC-MODIFIED N-TERMINUS

<400> SEQUENCE: 21

Arg Pro Gly Asn Phe Leu Gln Ser Arg Pro Glu Pro Thr Ala Pro Pro
1               5                   10                  15

Phe Leu Gln Ser Arg Pro Glu Pro Thr Ala Pro Pro Glu Glu Ser Phe
            20                  25                  30

Arg Arg Arg Arg
        35

<210> SEQ ID NO 22
<211> LENGTH: 36
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MISC_FEATURE
<222> LOCATION: (1)..(1)
<223> OTHER INFORMATION: TAMRA-MODIFIED N-TERMINUS

<400> SEQUENCE: 22

Arg Pro Gly Asn Phe Leu Gln Ser Arg Pro Glu Pro Thr Ala Pro Pro
1               5                   10                  15

Phe Leu Gln Ser Arg Pro Glu Pro Thr Ala Pro Pro Glu Glu Ser Phe
            20                  25                  30

Arg Arg Arg Arg
        35

```
<210> SEQ ID NO 23
<211> LENGTH: 2668
<212> TYPE: DNA
<213> ORGANISM: Artificial Sequence
<220> FEATURE:
<223> OTHER INFORMATION: pET28B-FLAG-WWP2 EXPRESSION VECTOR

<400> SEQUENCE: 23
gaattcggct tcgggatcca ccatggatta caaggatgac gacgataaga tggcatctgc      60
cagctctagc cgggcaggag tggccctgcc ttttgagaag tctcagctca ctttgaaagt     120
ggtgtccgca aagcccaagg tgcataatcg tcaacctcga attaactcct acgtggaggt     180
ggcggtggat ggactcccca gtgagaccaa aagactggg aagcgcattg ggagctctga     240
gcttctctgg aatgagatca tcattttgaa tgtcacggca cagagtcatt tagatttaaa     300
ggtctggagc tgccatacct tgagaaatga actgctaggc accgcatctg tcaacctctc     360
caacgtcttg aagaacaatg ggggcaaaat ggagaacatg cagctgaccc tgaacctgca     420
gacggagaac aaaggcagcg ttgtctcagg cggagagctg acaattttcc tggacgggcc     480
aactgttgat ctgggaaatg tgcctaatgg cagtgccctg acagatggat cacagctgcc     540
ttcgagagac tccagtggaa cagcagtagc tccagaaaac cggcaccagc cccccagcac     600
aaactgcttt ggtggaagat cccggacgca cagacattcg ggtgcttcag ccagaacaac     660
cccagcaacc ggcgagcaaa gccccggtgc tcggagccgg caccgccagc ccgtcaagaa     720
ctcaggccac agtggcttgg ccaatggcac agtgatgat gaacccacaa cagccactga     780
tcccgaagaa ccttccgttg ttggtgtgac gtccccacct gctgcaccct tgagtgtgac     840
cccgaatccc aacacgactt ctctccctgc cccagccaca ccggctgaag agaggaacc     900 cagcacttcg ggtacacagc agctcccagc ggctgcccag gccccgacg ctctgcctgc     960 tggatgggaa cagcgagagc tgcccaacgg acgtgtctat tatgttgacc acaataccaa    1020
gaccaccacc tgggagcggc cccttcctcc aggctgggaa aaacgcacag atccccgagg    1080
caggttttac tatgtggatc acaatactcg gaccaccacc tggcagcgtc cgaccgcgga    1140
gtacgtgcgc aactatgagc agtggcagtc gcagcggaat cagctccagg gggccatgca    1200
gcacttcagc caaagattcc tctaccagtc ttcgagtgct tcgactgacc atgatcccct    1260 gggcccctc cctcctggct gggagaagag acaggacaat ggacgggtgt attacgtgaa    1320
ccataacact cgcacgaccc agtgggagga tccccgacc caggggatga tccaggaacc    1380
agctctgccc ccaggatggg agatgaaata caccagcgag ggggtgcgat actttgtgga    1440
ccacaatacc cgcaccacca cctttaagga tcctcgcccg ggtttgagt cggggacgaa    1500 gcaaggttcc cctggtgctt atgaccgcag ttttcggtgg aagtatcacc agttccgttt    1560
cctctgccat tcaaatgccc tacctagcca cgtgaagatc agcgtttcca ggcagacgct    1620
tttcgaagat tccttccaac agatcatgaa catgaaaccc tatgacctgc gccgccggct    1680
ctacatcatc atgcgtggcg aggagggcct ggactatggg gcatcgcca gagagtggtt    1740 tttcctcctg tctcatgagg tgctcaaccc tatgtattgt ttatttgaat atgccggaaa    1800
gaacaattac tgcctgcaga tcaaccccgc ctcctccatc aacccggacc acctcaccta    1860
ctttcgcttt ataggcagat tcatcgccat ggcgctgtac catggaaagt tcatcgacac    1920
gggcttcacc ctccctttct acaagcggat gctcaataag agaccaaccc tgaaagacct    1980
ggagtccatt gaccctgagt tctacaactc cattgtctgg atcaaagaga caacctgga    2040 agaatgtggc ctggagctgt acttcatcca ggacatggag atactgggca aggtgacgac    2100
```

-continued

```
ccacgagctg aaggagggcg gcgagagcat ccgggtcaca gaggagaaca aggaagagta    2160
catcatgctg ctgactgact ggcgtttcac ccgaggcgtg gaagagcaga ccaaagcctt    2220
cctggatggc ttcaacgagg tggccccgct ggagtggctg cgctactttg acgagaaaga    2280
gctggagctg atgctgtgcg gcatgcagga gatagacatg agcgactggc agaagagcac    2340
catctaccgg cactacacca agaacagcaa gcagatccag tggttctggc aggtggtgaa    2400
ggagatggac aacgagaaga ggatccggct gctgcagttt gtcaccggta cctgccgcct    2460
gcccgtcggg ggatttgccg aactcatcgg tagcaacgga ccacagaagt tttgcattga    2520
caaagttggc aaggaaacct ggctgccacag aagccacacc tgcttcaacc gtctggatct    2580
tccaccctac aagagctacg aacagctgag agagaagctg ctgtatgcca ttgaggagac    2640
cgagggcttt ggacaggagt aactcgag                                       2668
```

<210> SEQ ID NO 24
<211> LENGTH: 879
<212> TYPE: PRT
<213> ORGANISM: Artificial Sequence
<220> FEATURE:
<223> OTHER INFORMATION: WWP2 RECOMBINANT PROTEIN

<400> SEQUENCE: 24

```
Met Asp Tyr Lys Asp Asp Asp Lys Met Ala Ser Ala Ser Ser
1               5                   10                  15

Arg Ala Gly Val Ala Leu Pro Phe Glu Lys Ser Gln Leu Thr Leu Lys
                20                  25                  30

Val Val Ser Ala Lys Pro Lys Val His Asn Arg Gln Pro Arg Ile Asn
            35                  40                  45

Ser Tyr Val Glu Val Ala Val Asp Gly Leu Pro Ser Glu Thr Lys Lys
        50                  55                  60

Thr Gly Lys Arg Ile Gly Ser Ser Glu Leu Leu Trp Asn Glu Ile Ile
65                  70                  75                  80

Ile Leu Asn Val Thr Ala Gln Ser His Leu Asp Leu Lys Val Trp Ser
                85                  90                  95

Cys His Thr Leu Arg Asn Glu Leu Leu Gly Thr Ala Ser Val Asn Leu
            100                 105                 110

Ser Asn Val Leu Lys Asn Asn Gly Gly Lys Met Glu Asn Met Gln Leu
        115                 120                 125

Thr Leu Asn Leu Gln Thr Glu Asn Lys Gly Ser Val Val Ser Gly Gly
    130                 135                 140

Glu Leu Thr Ile Phe Leu Asp Gly Pro Thr Val Asp Leu Gly Asn Val
145                 150                 155                 160

Pro Asn Gly Ser Ala Leu Thr Asp Gly Ser Gln Leu Pro Ser Arg Asp
                165                 170                 175

Ser Ser Gly Thr Ala Val Ala Pro Glu Asn Arg His Gln Pro Pro Ser
            180                 185                 190

Thr Asn Cys Phe Gly Gly Arg Ser Arg Thr His Arg His Ser Gly Ala
        195                 200                 205

Ser Ala Arg Thr Thr Pro Ala Thr Gly Glu Gln Ser Pro Gly Ala Arg
    210                 215                 220

Ser Arg His Arg Gln Pro Val Lys Asn Ser Gly His Ser Gly Leu Ala
225                 230                 235                 240

Asn Gly Thr Val Asn Asp Glu Pro Thr Thr Ala Thr Asp Pro Glu Glu
                245                 250                 255

Pro Ser Val Val Gly Val Thr Ser Pro Pro Ala Ala Pro Leu Ser Val
```

-continued

```
                260                 265                 270
Thr Pro Asn Pro Asn Thr Thr Ser Leu Pro Ala Pro Ala Thr Pro Ala
            275                 280                 285

Glu Gly Glu Glu Pro Ser Thr Ser Gly Thr Gln Gln Leu Pro Ala Ala
        290                 295                 300

Ala Gln Ala Pro Asp Ala Leu Pro Ala Gly Trp Glu Gln Arg Glu Leu
305                 310                 315                 320

Pro Asn Gly Arg Val Tyr Tyr Val Asp His Asn Thr Lys Thr Thr Thr
                325                 330                 335

Trp Glu Arg Pro Leu Pro Pro Gly Trp Glu Lys Arg Thr Asp Pro Arg
            340                 345                 350

Gly Arg Phe Tyr Tyr Val Asp His Asn Thr Arg Thr Thr Thr Trp Gln
        355                 360                 365

Arg Pro Thr Ala Glu Tyr Val Arg Asn Tyr Glu Gln Trp Gln Ser Gln
    370                 375                 380

Arg Asn Gln Leu Gln Gly Ala Met Gln His Phe Ser Gln Arg Phe Leu
385                 390                 395                 400

Tyr Gln Ser Ser Ser Ala Ser Thr Asp His Asp Pro Leu Gly Pro Leu
                405                 410                 415

Pro Pro Gly Trp Glu Lys Arg Gln Asp Asn Gly Arg Val Tyr Tyr Val
            420                 425                 430

Asn His Asn Thr Arg Thr Thr Gln Trp Glu Asp Pro Arg Thr Gln Gly
        435                 440                 445

Met Ile Gln Glu Pro Ala Leu Pro Pro Gly Trp Glu Met Lys Tyr Thr
    450                 455                 460

Ser Glu Gly Val Arg Tyr Phe Val Asp His Asn Thr Arg Thr Thr Thr
465                 470                 475                 480

Phe Lys Asp Pro Arg Pro Gly Phe Glu Ser Gly Thr Lys Gln Gly Ser
                485                 490                 495

Pro Gly Ala Tyr Asp Arg Ser Phe Arg Trp Lys Tyr His Gln Phe Arg
            500                 505                 510

Phe Leu Cys His Ser Asn Ala Leu Pro Ser His Val Lys Ile Ser Val
        515                 520                 525

Ser Arg Gln Thr Leu Phe Glu Asp Ser Phe Gln Gln Ile Met Asn Met
    530                 535                 540

Lys Pro Tyr Asp Leu Arg Arg Arg Leu Tyr Ile Ile Met Arg Gly Glu
545                 550                 555                 560

Glu Gly Leu Asp Tyr Gly Gly Ile Ala Arg Glu Trp Phe Phe Leu Leu
                565                 570                 575

Ser His Glu Val Leu Asn Pro Met Tyr Cys Leu Phe Glu Tyr Ala Gly
            580                 585                 590

Lys Asn Asn Tyr Cys Leu Gln Ile Asn Pro Ala Ser Ser Ile Asn Pro
        595                 600                 605

Asp His Leu Thr Tyr Phe Arg Phe Ile Gly Arg Phe Ile Ala Met Ala
    610                 615                 620

Leu Tyr His Gly Lys Phe Ile Asp Thr Gly Phe Thr Leu Pro Phe Tyr
625                 630                 635                 640

Lys Arg Met Leu Asn Lys Arg Pro Thr Leu Lys Asp Leu Glu Ser Ile
                645                 650                 655

Asp Pro Glu Phe Tyr Asn Ser Ile Val Trp Ile Lys Glu Asn Asn Leu
            660                 665                 670

Glu Glu Cys Gly Leu Glu Leu Tyr Phe Ile Gln Asp Met Glu Ile Leu
        675                 680                 685
```

Gly Lys Val Thr Thr His Glu Leu Lys Glu Gly Glu Ser Ile Arg
    690             695             700

Val Thr Glu Glu Asn Lys Glu Glu Tyr Ile Met Leu Leu Thr Asp Trp
705             710             715             720

Arg Phe Thr Arg Gly Val Glu Glu Gln Thr Lys Ala Phe Leu Asp Gly
            725             730             735

Phe Asn Glu Val Ala Pro Leu Glu Trp Leu Arg Tyr Phe Asp Glu Lys
            740             745             750

Glu Leu Glu Leu Met Leu Cys Gly Met Gln Glu Ile Asp Met Ser Asp
            755             760             765

Trp Gln Lys Ser Thr Ile Tyr Arg His Tyr Thr Lys Asn Ser Lys Gln
770             775             780

Ile Gln Trp Phe Trp Gln Val Val Lys Glu Met Asp Asn Glu Lys Arg
785             790             795             800

Ile Arg Leu Leu Gln Phe Val Thr Gly Thr Cys Arg Leu Pro Val Gly
            805             810             815

Gly Phe Ala Glu Leu Ile Gly Ser Asn Gly Pro Gln Lys Phe Cys Ile
            820             825             830

Asp Lys Val Gly Lys Glu Thr Trp Leu Pro Arg Ser His Thr Cys Phe
            835             840             845

Asn Arg Leu Asp Leu Pro Pro Tyr Lys Ser Tyr Glu Gln Leu Arg Glu
850             855             860

Lys Leu Leu Tyr Ala Ile Glu Glu Thr Glu Gly Phe Gly Gln Glu
865             870             875

<210> SEQ ID NO 25
<211> LENGTH: 7997
<212> TYPE: DNA
<213> ORGANISM: Artificial Sequence
<220> FEATURE:
<223> OTHER INFORMATION: pET28B-WWP2 EXPRESSION VECTOR

<400> SEQUENCE: 25

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct tgacgttgg agtccacgtt     300
ctttaatagt ggactcttgt tccaaactgg aacaacactc aaccctatct cggtctattc     360
ttttgattta agggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg aattaattct tagaaaaact catcgagcat caaatgaaac tgcaattta     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
```

```
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg caacgctac     1200 ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct  taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt cctgcgtta    2160 tccccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
```

| | |
|---|---|
| gagttgcatg ataaagaaga cagtcataag tgcggcgacg atagtcatgc cccgcgccca | 3420 |
| ccggaaggag ctgactgggt tgaaggctct caagggcatc ggtcgagatc cggtgccta | 3480 |
| atgagtgagc taacttacat taattgcgtt gcgctcactg cccgctttcc agtcgggaaa | 3540 |
| cctgtcgtgc cagctgcatt aatgaatcgg ccaacgcgcg gggagaggcg gtttgcgtat | 3600 |
| tgggcgccag ggtggttttt cttttcacca gtgagacggg caacagctga ttgcccttca | 3660 |
| ccgcctggcc ctgagagagt tgcagcaagc ggtccacgct ggtttgcccc agcaggcgaa | 3720 |
| aatcctgttt gatggtggtt aacggcggga tataacatga gctgtcttcg gtatcgtcgt | 3780 |
| atcccactac cgagatatcc gcaccaacgc gcagcccgga ctcggtaatg cgcgcattg | 3840 |
| cgcccagcgc catctgatcg ttggcaacca gcatcgcagt gggaacgatg ccctcattca | 3900 |
| gcatttgcat ggtttgttga aaaccggaca tggcactcca gtcgccttcc cgttccgcta | 3960 |
| tcggctgaat ttgattgcga gtgagatatt tatgccagcc agccagacgc agacgcgccg | 4020 |
| agacagaact taatgggccc gctaacagcg cgatttgctg gtgacccaat gcgaccagat | 4080 |
| gctccacgcc cagtcgcgta ccgtcttcat gggagaaaat aatactgttg atgggtgtct | 4140 |
| ggtcagagac atcaagaaat aacgccggaa cattagtgca ggcagcttcc acagcaatgg | 4200 |
| catcctggtc atccagcgga tagttaatga tcagcccact gacgcgttgc gcgagaagat | 4260 |
| tgtgcaccgc cgctttacag gcttcgacgc cgcttcgttc taccatcgac accaccacgc | 4320 |
| tggcacccag ttgatcggcg cgagatttaa tcgccgcgac aatttgcgac ggcgcgtgca | 4380 |
| gggccagact ggaggtggca acgccaatca gcaacgactg tttgcccgcc agttgttgtg | 4440 |
| ccacgcggtt gggaatgtaa ttcagctccg ccatcgccgc ttccactttt tcccgcgttt | 4500 |
| tcgcagaaac gtggctggcc tggttcacca cgcgggaaac ggtctgataa gagacaccgg | 4560 |
| catactctgc gacatcgtat aacgttactg gtttcacatt caccaccctg aattgactct | 4620 |
| cttccgggcg ctatcatgcc ataccgcgaa aggttttgcg ccattcgatg gtgtccggga | 4680 |
| tctcgacgct ctcccttatg cgactcctgc attaggaagc agcccagtag taggttgagg | 4740 |
| ccgttgagca ccgccgccgc aaggaatggt gcatgcaagg agatggcgcc caacagtccc | 4800 |
| ccggccacgg ggcctgccac catacccacg ccgaaacaag cgctcatgag cccgaagtgg | 4860 |
| cgagcccgat cttccccatc ggtgatgtcg gcgatatagg cgccagcaac cgcacctgtg | 4920 |
| gcgccggtga tgccggccac gatgcgtccg gcgtagagga tcgagatctc gatcccgcga | 4980 |
| aattaatacg actcactata ggggaattgt gagcggataa caattcccct ctagaaataa | 5040 |
| ttttgtttaa cttaagaaag gagatatacc atgggcagca gccatcatca tcatcatcac | 5100 |
| agcagcggcc tggtgccgcg cggcagccat atggctagca tgactggtgg acagcaaatg | 5160 |
| ggtcgcggat ccgaattcgg cttcgggatc caccatggat tacaaggatg acgacgataa | 5220 |
| gatggcatct gccagctcta gccgggcagg agtggccctg ccttttgaga gtctcagct | 5280 |
| cactttgaaa gtggtgtccg caaagcccaa ggtgcataat cgtcaacctc gaattaactc | 5340 |
| ctacgtggag gtggcggtgg atggactccc cagtgagacc aagaagactg ggaagcgcat | 5400 |
| tgggagctct gagcttctct ggaatgagat catcattttg aatgtcacgg cacagagtca | 5460 |
| tttagattta aaggtctgga gctgccatac cttgagaaat gaactgctag gcaccgcatc | 5520 |
| tgtcaacctc tccaacgtct tgaagaacaa tgggggcaaa atggagaaca tgcagctgac | 5580 |
| cctgaacctg cagacggaga acaaaggcag cgttgtctca ggcggagagc tgacaatttt | 5640 |
| cctggacggg ccaactgttg atctgggaaa tgtgcctaat ggcagtgccc tgacagatgg | 5700 |

```
atcacagctg ccttcgagag actccagtgg aacagcagta gctccagaga accggcacca    5760
gcccccagc acaaactgct ttggtggaag atcccggacg cacagacatt cgggtgcttc    5820
agccagaaca accccagcaa ccggcgagca agccccggt gctcggagcc ggcaccgcca    5880
gcccgtcaag aactcaggcc acagtggctt ggccaatggc acagtgaatg atgaacccac    5940
aacagccact gatcccgaag aaccttccgt tgttggtgtg acgtcccccac ctgctgcacc    6000
cttgagtgtg accccgaatc ccaacacgac ttctctccct gccccagcca caccggctga    6060
aggagaggaa cccagcactt cgggtacaca gcagctccca gcggctgccc aggcccccga    6120
cgctctgcct gctggatggg aacagcgaga gctgcccaac ggacgtgtct attatgttga    6180
ccacaatacc aagaccacca cctgggagcg gccccttcct ccaggctggg aaaaacgcac    6240
agatccccga ggcaggtttt actatgtgga tcacaatact cggaccacca cctggcagcg    6300
tccgaccgcg gagtacgtgc gcaactatga gcagtggcag tcgcagcgga atcagctcca    6360
gggggcatg cagcacttca gccaaagatt cctctaccag tcttcgagtg cttcgactga    6420
ccatgatccc ctgggccccc tccctcctgg ctggagaaag agacaggaca atggacgggt    6480
gtattacgtg aaccataaca ctcgcacgac ccagtgggag atccccggga cccaggggat    6540
gatccaggaa ccagctctgc ccccaggatg ggagatgaaa tacaccagcg aggggtgcg    6600
atactttgtg gaccacaata cccgcaccac cacctttaag gatcctcgcc cggggtttga    6660
gtcggggacg aagcaaggtt ccctggtgc ttatgaccgc agttttcggt ggaagtatca    6720
ccagttccgt ttcctctgcc attcaaatgc cctacctagc cacgtgaaga tcagcgtttc    6780
caggcagacg cttttcgaag attccttcca acagatcatg aacatgaaac cctatgacct    6840
gcgccgccgg ctctacatca tcatgcgtgg cgaggagggc ctggactatg ggggcatcgc    6900
cagagagtgt ttttcctcc tgtctcatga ggtgctcaac cctatgtatt gtttatttga    6960
atatgccgga aagaacaatt actgcctgca gatcaaccccc gcctcctcca tcaacccgga    7020
ccacctcacc tactttcgct ttataggcag attcatcgcc atggcgctgt accatggaaa    7080
gttcatcgac acgggcttca ccctcccttt ctacaagcgg atgctcaata agagaccaac    7140
cctgaaagac ctggagtcca ttgaccctga gttctacaac tccattgtct ggatcaaaga    7200
gaacaacctg gaagaatgtg gcctggagct gtacttcatc caggacatgg agatactggg    7260
caaggtgacg acccacgagc tgaaggaggg cggcgagagc atccgggtca cagaggagaa    7320
caaggaagag tacatcatgc tgctgactga ctggcgtttc acccgaggcg tggaagagca    7380
gaccaaagcc ttcctggatg gcttcaacga ggtggcccg ctggagtggc tgcgctactt    7440
tgacgagaaa gagctggagc tgatgctgtg cggcatgcag gagatagaca tgagcgactg    7500
gcagaagagc accatctacc ggcactacac caagaacagc aagcagatcc agtggttctg    7560
gcaggtggtg aaggagatgg acaacgagaa gaggatccgg ctgctgcagt tgtcaccgg    7620
tacctgccgc ctgcccgtcg ggggatttgc cgaactcatc ggtagcaacg gaccacagaa    7680
gttttgcatt gacaaagttg gcaaggaaac ctggctgccc agaagccaca cctgcttcaa    7740
ccgtctggat cttccacccct acaagagcta cgaacagctg agagagaagc tgctgtatgc    7800
cattgaggag accgagggct ttggacagga gtaactcgag caccaccacc accaccactg    7860
agatccggct gctaacaaag cccgaaagga agctgagttg gctgctgcca ccgctgagca    7920
ataactagca taaccccttg gggcctctaa acgggtcttg aggggttttt tgctgaaagg    7980
aggaactata tccggat                                                   7997
```

<210> SEQ ID NO 26
<211> LENGTH: 33
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 26
ataggattca tggccactgc ttcaccaagg tct                                33

<210> SEQ ID NO 27
<211> LENGTH: 35
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 27
atagcggccg ctcattcttg tccaaatccc tctgt                              35

<210> SEQ ID NO 28
<211> LENGTH: 2783
<212> TYPE: DNA
<213> ORGANISM: Artificial Sequence
<220> FEATURE:
<223> OTHER INFORMATION: WWP1 RECOMBINANT GENE INSERT SEQUENCE

<400> SEQUENCE: 28
gaattcatgg ccactgcttc accaaggtct gatactagta ataaccacag tggaaggttg     60
cagttacagg taactgtttc tagtgccaaa cttaaaagaa aaagaactg gttcggaaca     120 gcaatatata cagaagtagt tgtagatgga gaaattacga aacagcaaa atccagtagt    180 tcttctaatc caaatgggga tgaacagcta actgtaaatg ttacgccaca gactacattg    240
gaatttcaag tttggagcca tcgcacttta aaagcagatg ctttattagg aaaagcaacg   300
atagatttga acaagctct gttgatacac aatagaaaat tggaaagagt gaagaacaa    360 ttaaaacttt ccttggaaaa caagaatggc atagcacaaa ctggtgaatt gacagttgtg   420
cttgatggat tggtgattga gcaagaaaat ataacaaact gcagctcatc tccaaccata    480
gaaatacagg aaaatggtga tgccttacat gaaaatggag agccttcagc aaggacaact   540
gccaggttgg ctgttgaagg cacgaatgga atagataatc atgtacctac aagcactcta   600
gtccaaaact catgctgctc gtatgtagtt aatggagaca cacaccttc atctccgtct    660 caggttgctg ccagacccaa aaatacacca gctccaaaac cactcgcatc tgagcctgcc   720
gatgacactg ttaatggaga atcatcctca tttgcaccaa ctgataatgc gtctgtcacg    780
ggtactccag tagtgtctga agaaaatgcc ttgtctccaa attgcactag tactactgtt   840
gaagatcctc cagttcaaga aatactgact tcctcagaaa acaatgaatg tattccttct   900
accagtgcag aattggaatc tgaagctaga agtatattag agcctgacac ctctaattct   960
agaagtagtt ctgctttga agcagccaaa tcaagacagc cagatgggtg tatggatcct   1020
gtacggcagc agtctgggaa tgccaacaca gaaaccttgc catcagggtg ggaacaaaga  1080
aaagatcctc atggtagaac ctattatgtg gatcataata ctcgaactac cacatgggag  1140
agaccacaac ctttacctcc aggttgggaa agaagagttg atgatcgtag aagagtttat   1200
tatgtggatc ataacaccag aacaacaacg tggcagcggc taccatggga atctgtccga  1260
aattttgaac agtggcaatc tcagcggaac caattgcagg gagctatgca acagtttaac   1320
caacgatacc tctattcggc ttcaatgtta gctgcagaaa atgaccctta tggacctttg   1380

```
ccaccaggct gggaaaaaag agtggattca acagacaggg tttactttgt gaatcataac   1440
acaaaaacaa cccagtggga agatccaaga actcaaggct tacagaatga agaacccctg   1500
ccagaaggct gggaaattag atatactcgt gaaggtgtaa ggtactttgt tgatcataac   1560
acaagaacaa caacattcaa agatcctcgc aatgggaagt catctgtaac taaaggtggt   1620
ccacaaattg cttatgaacg cggctttagg tggaagcttg ctcacttccg ttatttgtgc   1680
cagtctaatg cactacctag tcatgtaaag atcaatgtgt cccggcagac attgtttgaa   1740
gattccttcc aacagattat ggcattaaaa ccctatgact tgaggaggcg cttatatgta   1800
atatttagag gagaagaagg acttgattat ggtggcctag cgagagaatg gtttttcttg   1860
ctttcacatg aagttttgaa cccaatgtat tgcttatttg agtatgcggg caagaacaac   1920
tattgtctgc agataaatcc agcatcaacc attaatccag accatctttc atacttctgt   1980
ttcattggtc gttttattgc catggcacta tttcatggaa agtttatcga tactggtttc   2040
tctttaccat tctacaagcg tatgttaagt aaaaaactta ctattaagga tttggaatct   2100
attgatactg aattttataa ctcccttatc tggataagag ataacaacat tgaagaatgt   2160
ggcttagaaa tgtactttc tgttgacatg gagatttttgg gaaaagttac ttcacatgac   2220
ctgaagttgg gaggttccaa tattctggtg actgaggaga caaagatga atatattggt   2280 ttaatgacag aatggcgttt ttctcgagga gtacaagaac agaccaaagc tttccttgat   2340
ggttttaatg aagttgttcc tcttcagtgg ctacagtact tcgatgaaaa agaattagag   2400
gttatgttgt gtggcatgca ggaggttgac ttggcagatt ggcagagaaa tactgtttat   2460
cgacattata caagaaacag caagcaaatc atttggtttt ggcagtttgt gaaagagaca   2520
gacaatgaag taagaatgcg actattgcag ttcgtcactg gaacctgccg tttacctcta   2580
ggaggatttg ctgagctcat gggaagtaat gggcctcaaa agttttgcat tgaaaaagtt   2640
ggcaaagaca cttggttacc aagaagccat acatgtttta atcgcttgga tctaccacca   2700
tataagagtt atgaacaact aaaggaaaaa cttcttttttg caatagaaga gacagaggga   2760
tttggacaag aatgagcggc cgc                                            2783
```

<210> SEQ ID NO 29
<211> LENGTH: 922
<212> TYPE: PRT
<213> ORGANISM: Artificial Sequence
<220> FEATURE:
<223> OTHER INFORMATION: WWP1 PEPTIDE SEQUENCE

<400> SEQUENCE: 29

```
Met Ala Thr Ala Ser Pro Arg Ser Asp Thr Ser Asn Asn His Ser Gly
1               5                   10                  15

Arg Leu Gln Leu Gln Val Thr Val Ser Ser Ala Lys Leu Lys Arg Lys
            20                  25                  30

Lys Asn Trp Phe Gly Thr Ala Ile Tyr Thr Glu Val Val Asp Gly
        35                  40                  45

Glu Ile Thr Lys Thr Ala Lys Ser Ser Ser Ser Asn Pro Lys Trp
    50                  55                  60

Asp Glu Gln Leu Thr Val Asn Val Thr Pro Gln Thr Thr Leu Glu Phe
65                  70                  75                  80

Gln Val Trp Ser His Arg Thr Leu Lys Ala Asp Ala Leu Leu Gly Lys
                85                  90                  95

Ala Thr Ile Asp Leu Lys Gln Ala Leu Leu Ile His Asn Arg Lys Leu
            100                 105                 110
```

-continued

Glu Arg Val Lys Glu Gln Leu Lys Leu Ser Leu Glu Asn Lys Asn Gly
            115                 120                 125

Ile Ala Gln Thr Gly Glu Leu Thr Val Val Leu Asp Gly Leu Val Ile
    130                 135                 140

Glu Gln Glu Asn Ile Thr Asn Cys Ser Ser Pro Thr Ile Glu Ile
145                 150                 155                 160

Gln Glu Asn Gly Asp Ala Leu His Glu Asn Gly Pro Ser Ala Arg
                165                 170                 175

Thr Thr Ala Arg Leu Ala Val Glu Gly Thr Asn Gly Ile Asp Asn His
            180                 185                 190

Val Pro Thr Ser Thr Leu Val Gln Asn Ser Cys Cys Ser Tyr Val Val
        195                 200                 205

Asn Gly Asp Asn Thr Pro Ser Ser Pro Ser Gln Val Ala Ala Arg Pro
210                 215                 220

Lys Asn Thr Pro Ala Pro Lys Pro Leu Ala Ser Glu Pro Ala Asp Asp
225                 230                 235                 240

Thr Val Asn Gly Glu Ser Ser Phe Ala Pro Thr Asp Asn Ala Ser
                245                 250                 255

Val Thr Gly Thr Pro Val Val Ser Glu Glu Asn Ala Leu Ser Pro Asn
            260                 265                 270

Cys Thr Ser Thr Thr Val Glu Asp Pro Pro Val Gln Glu Ile Leu Thr
    275                 280                 285

Ser Ser Glu Asn Asn Glu Cys Ile Pro Ser Thr Ser Ala Glu Leu Glu
    290                 295                 300

Ser Glu Ala Arg Ser Ile Leu Glu Pro Asp Thr Ser Asn Ser Arg Ser
305                 310                 315                 320

Ser Ser Ala Phe Glu Ala Ala Lys Ser Arg Gln Pro Asp Gly Cys Met
                325                 330                 335

Asp Pro Val Arg Gln Gln Ser Gly Asn Ala Asn Thr Glu Thr Leu Pro
            340                 345                 350

Ser Gly Trp Glu Gln Arg Lys Asp Pro His Gly Arg Thr Tyr Tyr Val
        355                 360                 365

Asp His Asn Thr Arg Thr Thr Thr Trp Glu Arg Pro Gln Pro Leu Pro
    370                 375                 380

Pro Gly Trp Glu Arg Arg Val Asp Asp Arg Arg Arg Val Tyr Tyr Val
385                 390                 395                 400

Asp His Asn Thr Arg Thr Thr Thr Trp Gln Arg Pro Thr Met Glu Ser
                405                 410                 415

Val Arg Asn Phe Glu Gln Trp Gln Ser Gln Arg Asn Gln Leu Gln Gly
            420                 425                 430

Ala Met Gln Gln Phe Asn Gln Arg Tyr Leu Tyr Ser Ala Ser Met Leu
        435                 440                 445

Ala Ala Glu Asn Asp Pro Tyr Gly Pro Leu Pro Pro Gly Trp Glu Lys
    450                 455                 460

Arg Val Asp Ser Thr Asp Arg Val Tyr Phe Val Asn His Asn Thr Lys
465                 470                 475                 480

Thr Thr Gln Trp Glu Asp Pro Arg Thr Gln Gly Leu Gln Asn Glu Glu
                485                 490                 495

Pro Leu Pro Glu Gly Trp Glu Ile Arg Tyr Thr Arg Glu Gly Val Arg
            500                 505                 510

Tyr Phe Val Asp His Asn Thr Arg Thr Thr Phe Lys Asp Pro Arg
        515                 520                 525

Asn Gly Lys Ser Ser Val Thr Lys Gly Gly Pro Gln Ile Ala Tyr Glu

```
        530                 535                 540
Arg Gly Phe Arg Trp Lys Leu Ala His Phe Arg Tyr Leu Cys Gln Ser
545                 550                 555                 560

Asn Ala Leu Pro Ser His Val Lys Ile Asn Val Ser Arg Gln Thr Leu
                565                 570                 575

Phe Glu Asp Ser Phe Gln Gln Ile Met Ala Leu Lys Pro Tyr Asp Leu
            580                 585                 590

Arg Arg Arg Leu Tyr Val Ile Phe Arg Gly Glu Glu Gly Leu Asp Tyr
        595                 600                 605

Gly Gly Leu Ala Arg Glu Trp Phe Phe Leu Leu Ser His Glu Val Leu
    610                 615                 620

Asn Pro Met Tyr Cys Leu Phe Glu Tyr Ala Gly Lys Asn Asn Tyr Cys
625                 630                 635                 640

Leu Gln Ile Asn Pro Ala Ser Thr Ile Asn Pro Asp His Leu Ser Tyr
                645                 650                 655

Phe Cys Phe Ile Gly Arg Phe Ile Ala Met Ala Leu Phe His Gly Lys
            660                 665                 670

Phe Ile Asp Thr Gly Phe Ser Leu Pro Phe Tyr Lys Arg Met Leu Ser
        675                 680                 685

Lys Lys Leu Thr Ile Lys Asp Leu Glu Ser Ile Asp Thr Glu Phe Tyr
    690                 695                 700

Asn Ser Leu Ile Trp Ile Arg Asp Asn Ile Glu Glu Cys Gly Leu
705                 710                 715                 720

Glu Met Tyr Phe Ser Val Asp Met Glu Ile Leu Gly Lys Val Thr Ser
                725                 730                 735

His Asp Leu Lys Leu Gly Gly Ser Asn Ile Leu Val Thr Glu Glu Asn
            740                 745                 750

Lys Asp Glu Tyr Ile Gly Leu Met Thr Glu Trp Arg Phe Ser Arg Gly
        755                 760                 765

Val Gln Glu Gln Thr Lys Ala Phe Leu Asp Gly Phe Asn Glu Val Val
    770                 775                 780

Pro Leu Gln Trp Leu Gln Tyr Phe Asp Glu Lys Glu Leu Glu Val Met
785                 790                 795                 800

Leu Cys Gly Met Gln Glu Val Asp Leu Ala Asp Trp Gln Arg Asn Thr
                805                 810                 815

Val Tyr Arg His Tyr Thr Arg Asn Ser Lys Gln Ile Ile Trp Phe Trp
            820                 825                 830

Gln Phe Val Lys Glu Thr Asp Asn Glu Val Arg Met Arg Leu Leu Gln
        835                 840                 845

Phe Val Thr Gly Thr Cys Arg Leu Pro Leu Gly Gly Phe Ala Glu Leu
    850                 855                 860

Met Gly Ser Asn Gly Pro Gln Lys Phe Cys Ile Glu Lys Val Gly Lys
865                 870                 875                 880

Asp Thr Trp Leu Pro Arg Ser His Thr Cys Phe Asn Arg Leu Asp Leu
                885                 890                 895

Pro Pro Tyr Lys Ser Tyr Glu Gln Leu Lys Glu Lys Leu Leu Phe Ala
            900                 905                 910

Ile Glu Glu Thr Glu Gly Phe Gly Gln Glu
        915                 920

<210> SEQ ID NO 30
<211> LENGTH: 8119
<212> TYPE: DNA
<213> ORGANISM: Artificial Sequence
```

<220> FEATURE:
<223> OTHER INFORMATION: pET28B-WWP1 EXPRESSION VECTOR

<400> SEQUENCE: 30

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggc tcccttttagg     180
gttccgattt agtgctttac ggcacctcga ccccaaaaaa cttgattagg gtgatggttc     240
acgtagtggg ccatcgccct gatagacggt ttttcgccct tgacgttgg agtccacgtt     300
ctttaatagt ggactcttgt tccaaactgg aacaacactc aaccctatct cggtctattc     360
ttttgattta tagggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga acgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc gaagggaga    1920
aaggcggaca ggtatccggt aagcggcagg gtcggaacag gagagcgcac gagggagctt    1980
ccaggggga acgcctggta tctttatagt cctgtcgggt ttcgccacct ctgacttgag    2040
cgtcgatttt tgtgatgctc gtcagggggg cggagcctat ggaaaaacgc cagcaacgcg    2100
gccttttttac ggttcctggc cttttgctgg cctttttgctc acatgttctt tcctgcgtta    2160
tccctgatt ctgtggataa ccgtattacc gcctttgagt gagctgatac cgctcgccgc    2220
```

```
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccgagac gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
```

```
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgggcagca gccatcatca tcatcatcac   5100
agcagcggcc tggtgccgcg cggcagccat atggctagca tgactggtgg acagcaaatg   5160
ggtcgcggat ccgaattcat ggccactgct tcaccaaggt ctgatactag taataaccac   5220
agtggaaggt tgcagttaca ggtaactgtt tctagtgcca aacttaaaag aaaaaagaac   5280
tggttcggaa cagcaatata tacagaagta gttgtagatg gagaaattac gaaaacagca   5340
aaatccagta gttcttctaa tccaaaatgg gatgaacagc taactgtaaa tgttacgcca   5400
cagactacat tggaatttca gtttggagc catcgcactt taaaagcaga tgctttatta   5460
ggaaaagcaa cgatagattt gaaacaagct ctgttgatac acaatagaaa attggaaaga   5520
gtgaaagaac aattaaaact ttccttggaa aacaagaatg gcatagcaca aactggtgaa   5580
ttgacagttg tgcttgatgg attggtgatt gagcaagaaa atataacaaa ctgcagctca   5640
tctccaacca tagaaataca ggaaaatggt gatgccttac atgaaaatgg agagccttca   5700
gcaaggacaa ctgccaggtt ggctgttgaa ggcacgaatg gaatagataa tcatgtacct   5760
acaagcactc tagtccaaaa ctcatgctgc tcgtatgtag ttaatggaga caacacacct   5820
tcatctccgt ctcaggttgc tgccagaccc aaaaatacac cagctccaaa accactcgca   5880
tctgagcctg ccgatgacac tgttaatgga gaatcatcct catttgcacc aactgataat   5940
gcgtctgtca cgggtactcc agtagtgtct gaagaaaatg ccttgtctcc aaattgcact   6000
agtactactg ttgaagatcc tccagttcaa gaaatactga cttcctcaga aaacaatgaa   6060
tgtattcctt ctaccagtgc agaattggaa tctgaagcta gaagtatatt agagcctgac   6120
acctctaatt ctagaagtag ttctgctttt gaagcagcca aatcaagaca gccagatggg   6180
tgtatggatc ctgtacggca gcagtctggg aatgccaaca cagaaacctt gccatcaggg   6240
tgggaacaaa gaaagatcc tcatggtaga acctattatg tggatcataa tactcgaact   6300
accacatggg agagaccaca acctttacct ccaggttggg aaagaagagt tgatgatcgt   6360
agaagagttt attatgtgga tcataacacc agaacaacaa cgtggcagcg gcctaccatg   6420
gaatctgtcc gaaattttga acagtggcaa tctcagcgga accaattgca gggagctatg   6480
caacagttta ccaacgata cctctattcg gcttcaatgt tagctgcaga aaatgaccct   6540
tatggacctt tgccaccagg ctgggaaaaa gagtggatt caacgacag gtttacttt   6600 gtgaatcata acacaaaaac aacccagtgg gaagatccaa gaactcaagg cttacagaat   6660
gaagaacccc tgccagaagg ctgggaaatt agatatactc gtgaaggtgt aaggtacttt   6720
gttgatcata cacaagaac aacaacattc aaagatcctc gcaatgggaa gtcatctgta   6780
actaaaggtg gtccacaaat tgcttatgaa cgcggcttta ggtggaagct tgctcacttc   6840
cgttatttgt gccagtctaa tgcactacct agtcatgtaa agatcaatgt gtcccggcag   6900
acattgtttg aagattcctt ccaacagatt atggcattaa aaccctatga cttgaggagg   6960
```

| | |
|---|---|
| cgcttatatg taatatttag aggagaagaa ggacttgatt atggtggcct agcgagagaa | 7020 |
| tggtttttct tgctttcaca tgaagttttg aacccaatgt attgcttatt tgagtatgcg | 7080 |
| ggcaagaaca actattgtct gcagataaat ccagcatcaa ccattaatcc agaccatctt | 7140 |
| tcatacttct gtttcattgg tcgttttatt gccatggcac tatttcatgg aaagtttatc | 7200 |
| gatactggtt tctctttacc attctacaag cgtatgttaa gtaaaaaact tactattaag | 7260 |
| gatttggaat ctattgatac tgaattttat aactcccctta tctggataag agataacaac | 7320 |
| attgaagaat gtggcttaga aatgtacttt tctgttgaca tggagatttt gggaaaagtt | 7380 |
| acttcacatg acctgaagtt gggaggttcc aatattctgg tgactgagga gaacaaagat | 7440 |
| gaatatattg gtttaatgac agaatggcgt ttttctcgag gagtacaaga acagaccaaa | 7500 |
| gctttccttg atggttttaa tgaagttgtt cctcttcagt ggctacagta cttcgatgaa | 7560 |
| aaagaattag aggttatgtt gtgtggcatg caggaggttg acttggcaga ttggcagaga | 7620 |
| aatactgttt atcgacatta tacaagaaac agcaagcaaa tcatttggtt ttggcagttt | 7680 |
| gtgaaagaga cagacaatga agtaagaatg cgactattgc agttcgtcac tggaacctgc | 7740 |
| cgtttacctc taggaggatt tgctgagctc atgggaagta atgggcctca aaagttttgc | 7800 |
| attgaaaaag ttggcaaaga cacttggtta ccaagaagcc atacatgttt taatcgcttg | 7860 |
| gatctaccac catataagag ttatgaacaa ctaaaggaaa aacttctttt tgcaatagaa | 7920 |
| gagacagagg gatttggaca agaatgagcg gccgcactcg agcaccacca ccaccaccac | 7980 |
| tgagatccgg ctgctaacaa agcccgaaag gaagctgagt tggctgctgc caccgctgag | 8040 |
| caataactag cataacccct tggggcctct aaacgggtct gaggggttt tttgctgaaa | 8100 |
| ggaggaacta tatccggat | 8119 |

<210> SEQ ID NO 31
<211> LENGTH: 1562
<212> TYPE: DNA
<213> ORGANISM: Artificial Sequence
<220> FEATURE:
<223> OTHER INFORMATION: TSG101 GENE SEQUENCE

<400> SEQUENCE: 31

| | |
|---|---|
| gaagcggaag tggtgtagtg gtgccgactt cctgttgttt gaggccgggt tgggggtgtg | 60 |
| cgattgtgtg ggacggtctg gggcagccca gcagcggctg accctctgcc tgcggggaag | 120 |
| ggagtcgcca ggcggccgtc atggcggtgt cggagagcca gctcaagaaa atggtgtcca | 180 |
| agtacaaata cagagaccta actgtacgtg aaactgtcaa tgttattact ctatacaaag | 240 |
| atctcaaacc tgttttggat tcatatgttt ttaacgatgg cagttccagg gaactaatga | 300 |
| acctcactgg aacaatccct gtgccttata gaggtaatac atacaatatt ccaatatgcc | 360 |
| tatggctact ggacacatac ccatataatc cccctatctg ttttgttaag cctactagtt | 420 |
| caatgactat taaacagga aagcatgttg atgcaaatgg aagatatat cttccttatc | 480 |
| tacatgaatg gaaacaccca cagtcagact tgttggggct tattcaggtc atgattgtgg | 540 |
| tatttggaga tgaacctcca gtcttctctc gtcctatttc ggcatcctat ccgccatacc | 600 |
| aggcaacggg gccaccaaat acttcctaca tgccaggcat gccaggtgga atctctccat | 660 |
| acccatccgg ataccctccc aatcccagtg gttaccaggg ctgtccttac ccacctggtg | 720 |
| gtccatatcc tgccacaaca agttctcagt acccttctca gcctcctgtg accactgttg | 780 |
| gtcccagtag ggatggcaca atcagcgagg acaccatccg agcctctctc atctctgcgg | 840 |
| tcagtgacaa actgagatgg cggatgaagg aggaaatgga tcgtgcccag gcagagctca | 900 |

-continued

```
atgccttgaa acgaacagaa gaagacctga aaagggtca ccagaaactg gaagagatgg    960
ttacccgttt agatcaagaa gtagccgagg ttgataaaaa catagaactt ttgaaaaaga   1020
aggatgaaga actcagttct gctctggaaa aaatggaaaa tcagtctgaa acaatgata   1080 tcgatgaagt tatcattccc acagctccct tatacaaaca gatcctgaat ctgtatgcag   1140
aagaaaacgc tattgaagac actatctttt acttgggaga agccttgaga aggggcgtga   1200
tagacctgga tgtcttcctg aagcatgtac gtcttctgtc ccgtaaacag ttccagctga   1260
gggcactaat gcaaaaagca agaaagactg ccggtctcag tgacctctac tgacttctct   1320
gataccagct ggaggttgag ctcttcttaa agtattcttc tcttccttt atcagtaggt    1380 gcccagaata agttattgca gtttatcatt caagtgtaaa atattttgaa tcaataatat    1440
attttctgtt ttcttttggt aaagactggc ttttattaat gcactttcta tcctctgtaa    1500 acttttgtg ctgaatgttg ggactgctaa ataaatttg ttgcataaaa aaaaaaaaaa     1560
aa                                                                  1562
```

<210> SEQ ID NO 32
<211> LENGTH: 390
<212> TYPE: PRT
<213> ORGANISM: Artificial Sequence
<220> FEATURE:
<223> OTHER INFORMATION: TSG101 PROTEIN SEQUENCE

<400> SEQUENCE: 32

```
Met Ala Val Ser Glu Ser Gln Leu Lys Lys Met Val Ser Lys Tyr Lys
1               5                   10                  15

Tyr Arg Asp Leu Thr Val Arg Glu Thr Val Asn Val Ile Thr Leu Tyr
                20                  25                  30

Lys Asp Leu Lys Pro Val Leu Asp Ser Tyr Val Phe Asn Asp Gly Ser
            35                  40                  45

Ser Arg Glu Leu Met Asn Leu Thr Gly Thr Ile Pro Val Pro Tyr Arg
        50                  55                  60

Gly Asn Thr Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Glu Trp Lys His Pro Gln Ser Asp Leu Leu Gly Leu Ile
        115                 120                 125

Gln Val Met Ile Val Val Phe Gly Asp Glu Pro Pro Val Phe Ser Arg
    130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
            180                 185                 190

Gly Gly Pro Tyr Pro Ala Thr Thr Ser Ser Gln Tyr Pro Ser Gln Pro
        195                 200                 205

Pro Val Thr Thr Val Gly Pro Ser Arg Asp Gly Thr Ile Ser Glu Asp
    210                 215                 220

Thr Ile Arg Ala Ser Leu Ile Ser Ala Val Ser Asp Lys Leu Arg Trp
225                 230                 235                 240
```

```
Arg Met Lys Glu Glu Met Asp Arg Ala Gln Ala Glu Leu Asn Ala Leu
                245                 250                 255

Lys Arg Thr Glu Glu Asp Leu Lys Lys Gly His Gln Lys Leu Glu Glu
            260                 265                 270

Met Val Thr Arg Leu Asp Gln Glu Val Ala Glu Val Asp Lys Asn Ile
        275                 280                 285

Glu Leu Leu Lys Lys Lys Asp Glu Glu Leu Ser Ser Ala Leu Glu Lys
    290                 295                 300

Met Glu Asn Gln Ser Glu Asn Asp Ile Asp Val Ile Ile Pro
305                 310                 315                 320

Thr Ala Pro Leu Tyr Lys Gln Ile Leu Asn Leu Tyr Ala Glu Glu Asn
                325                 330                 335

Ala Ile Glu Asp Thr Ile Phe Tyr Leu Gly Glu Ala Leu Arg Arg Gly
            340                 345                 350

Val Ile Asp Leu Asp Val Phe Leu Lys His Val Arg Leu Leu Ser Arg
        355                 360                 365

Lys Gln Phe Gln Leu Arg Ala Leu Met Gln Lys Ala Arg Lys Thr Ala
    370                 375                 380

Gly Leu Ser Asp Leu Tyr
385                 390

<210> SEQ ID NO 33
<211> LENGTH: 174
<212> TYPE: PRT
<213> ORGANISM: Artificial Sequence
<220> FEATURE:
<223> OTHER INFORMATION: TRUNCATED-LENGTH TSG101 RECOMBINANT PEPTIDE

<400> SEQUENCE: 33

Met Gly Ser Ser His His His His His His Ser Ser Gly Leu Val Pro
1               5                   10                  15

Arg Gly Ser His Met Ala Ser Glu Asn Leu Tyr Phe Gln Gly Ala Val
            20                  25                  30

Ser Glu Ser Gln Leu Lys Lys Met Val Ser Lys Tyr Lys Tyr Arg Asp
        35                  40                  45

Leu Thr Val Arg Glu Thr Val Asn Val Ile Thr Leu Tyr Lys Asp Leu
    50                  55                  60

Lys Pro Val Leu Asp Ser Tyr Val Phe Asn Asp Gly Ser Ser Arg Glu
65                  70                  75                  80

Leu Met Asn Leu Thr Gly Thr Ile Pro Val Pro Tyr Arg Gly Asn Thr
                85                  90                  95

Tyr Asn Ile Pro Ile Cys Leu Trp Leu Leu Asp Thr Tyr Pro Tyr Asn
            100                 105                 110

Pro Pro Ile Cys Phe Val Lys Pro Thr Ser Ser Met Thr Ile Lys Thr
        115                 120                 125

Gly Lys His Val Asp Ala Asn Gly Lys Ile Tyr Leu Pro Tyr Leu His
    130                 135                 140

Glu Trp Lys His Pro Gln Ser Asp Leu Leu Gly Leu Ile Gln Val Met
145                 150                 155                 160

Ile Val Val Phe Gly Asp Glu Pro Pro Val Phe Ser Arg Pro
                165                 170

<210> SEQ ID NO 34
<211> LENGTH: 5801
<212> TYPE: DNA
<213> ORGANISM: Artificial Sequence
```

<220> FEATURE:
<223> OTHER INFORMATION: pET28B-TRUNCATED-LENGTH TSG101 RECOMBINANT
      PEPTIDE EXPRESSION VECTOR

<400> SEQUENCE: 34

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tcccttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggatttt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | ccctatttg | tttatttttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatccttttt | ttctgcgcgt | aatctgctgc | ttgcaaacaa | aaaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |
| cagcggtcgg | gctgaacggg | gggttcgtgc | acacagccca | gcttggagcg | aacgacctac | 1860 |
| accgaactga | gatacctaca | gcgtgagcta | tgagaaagcg | ccacgcttcc | cgaagggaga | 1920 |
| aaggcggaca | ggtatccggt | aagcggcagg | gtcggaacag | gagagcgcac | gagggagctt | 1980 |
| ccagggggaa | acgcctggta | tctttatagt | cctgtcgggt | ttcgccacct | ctgacttgag | 2040 |
| cgtcgatttt | tgtgatgctc | gtcagggggg | cggagcctat | ggaaaaacgc | cagcaacgcg | 2100 |
| gcctttttac | ggttcctggc | cttttgctgg | ccttttgctc | acatgttctt | tcctgcgtta | 2160 |
| tcccctgatt | ctgtggataa | ccgtattacc | gcctttgagt | gagctgatac | cgctcgccgc | 2220 |

```
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgcccgac acccgccaac accgctgac gcgccctgac gggcttgtct      2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccgaa cattagtgca ggcagcttcc acagcaatgg     4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgca aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
```

```
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc aacagtccc    4800 ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgggcagca gccatcatca tcatcatcac    5100
agcagcggcc tggtgccgcg cggcagccat atggctagcg aaaacctgta cttccagggc    5160
gcggtgtcgg agagccagct caagaaaatg gtgtccaagt acaaatacag agacctaact    5220
gtacgtgaaa ctgtcaatgt tattactcta tacaaagatc tcaaacctgt tttggattca    5280
tatgttttta acgatggcag ttccagggaa ctaatgaacc tcactggaac aatccctgtg    5340
ccttatagag gtaatacata caatattcca atatgcctat ggctactgga cacatacccca    5400 tataatcccc ctatctgttt tgttaagcct actagttcaa tgactattaa acaggaaag    5460 catgttgatg caaatgggaa gatatatctt ccttatctac atgaatggaa acacccacag    5520
tcagacttgt tggggcttat tcaggtcatg attgtggtat ttggagatga acctccagtc    5580
ttctctcgtc cttgataagg atccgaattc gagctccgtc gacaagcttg cggccgcact    5640
cgagcaccac caccaccacc actgagatcc ggctgctaac aaagcccgaa aggaagctga    5700
gttggctgct gccaccgctg agcaataact agcataaccc cttggggcct ctaaacgggt    5760
cttgaggggt tttttgctga aaggaggaac tatatccgga t                       5801
```

<210> SEQ ID NO 35
<211> LENGTH: 60
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 35

```
ataggatcca ccggtcgcca ccggtggctc tggcaagaac ggcatcaagg tgaacttcaa    60
```

<210> SEQ ID NO 36
<211> LENGTH: 34
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 36

```
gtcgcggccg ctttacttgt acagctcgtc catg                                34
```

<210> SEQ ID NO 37
<211> LENGTH: 4
<212> TYPE: PRT
<213> ORGANISM: Artificial Sequence
<220> FEATURE:
<223> OTHER INFORMATION: INTERPEPTIDE LINKER

<400> SEQUENCE: 37

Gly Gly Ser Gly
1

```
<210> SEQ ID NO 38
<211> LENGTH: 17
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 38
gcagagctgg tttagtg                                                    17

<210> SEQ ID NO 39
<211> LENGTH: 17
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 39
gcagagctgg tttagtg                                                    17

<210> SEQ ID NO 40
<211> LENGTH: 58
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 40
atactcgaga tctgagtacc cagagccaga gccaccctgc ttgtcggcca tgatatag       58

<210> SEQ ID NO 41
<211> LENGTH: 6
<212> TYPE: PRT
<213> ORGANISM: Artificial Sequence
<220> FEATURE:
<223> OTHER INFORMATION: INTERPEPTIDE LINKER

<400> SEQUENCE: 41

Gly Gly Ser Gly Ser Gly
1               5

<210> SEQ ID NO 42
<211> LENGTH: 17
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 42
gtgggaggtt ttttaaa                                                    17
```

METHODS AND COMPOUNDS TO INHIBIT ENVELOPED VIRUS RELEASE

CROSS-REFERENCE TO RELATED APPLICATIONS

This application is a divisional of U.S. patent application Ser. No. 14/138,053, filed Dec. 21, 2013, which claims benefit of priority to U.S. provisional application Ser. No. 61/745,336 filed Dec. 21, 2012, which is incorporated by reference in its entirety.

STATEMENT REGARDING FEDERALLY SPONSORED RESEARCH OR DEVELOPMENT

This invention was made with government support under AI068463 awarded by the National Institutes of Health. The government has certain rights in the invention.

SEQUENCE LISTING

The instant application contains a Sequence Listing that has been submitted in ASCII format via EFS-Web and is hereby incorporated by reference in its entirety. Said ASCII copy, created in final form on Dec. 20, 2013, is named NWNO1-012-US ST25.txt, and is 68,266 bytes in size.

FIELD OF THE INVENTION

This invention relates to methods for identifying compounds that inhibit interactions with the Nedd4 family of ubiquitin ligases and Tsg101, including inhibitors of virus budding.

BACKGROUND OF THE INVENTION

There is considerable interest developing antiviral reagents to combat viral infections. The two most prevalent antiviral strategies focus on creating immunity to viral infection by use of vaccines or by interfering with a necessary virus-specific process essential to virus maintenance, replication and propagation in the host.

Vaccines have been successfully developed for many viruses to combat viral infections. So-called live vaccines containing attenuated version(s) of the target virus provide a convenient means of conferring immunity as typically only one inoculation is required. The drawbacks to most live virus vaccines lie in their limited shelf life, the requirement for maintaining appropriate storage conditions to preserve the vaccine reagent, and the possibility of revertance to high virulence due to their active replication. These drawbacks can be avoided by using so-called inactivated virus vaccines containing a completely inert virus particle or a sub-viral component like a protein. The drawback to inactive viral vaccines is that multiple inoculations are required to confer full immunity. Furthermore, vaccines have an attendant risk that adverse reactions might arise in certain populations following immunization (for example, autoimmunity responses associated with Guillain-Barré syndrome (GBS)).

Antiviral compounds that specifically target a viral replication process have also proven effective for treating some virus infections. Examples of such reagents include small molecule inhibitors selective for a given viral protein, such as a viral replicase (for example, the nucleoside analog 3'-azidothymidine for inhibiting the HIV-1 reverse transcriptase) or a viral protease (for example, Darunavir for inhibiting HIV-1 protease). Owing to their small molecular size and chemical composition, antiviral compounds can be formulated as pharmaceutical compositions having significant shelf life and can typically retain their potency over a larger temperature range during storage than many vaccines. However, HIV-1 and other virus can mutate to escape the effectiveness of the antiviral drugs when such drugs are targeted against virus-specific proteins. In particular, HIV-specific drugs have side-effects that cause patients to interrupt therapy that can lead to drug-resistant viral strains.

Generally, antiviral compounds are typically used in combinations for maximum efficacy and durability. Though most aspects of the viral replication process are susceptible to targeting and inhibition, the primary focus of antiviral inhibitor drug development is on early stage processes of viral replication, when the copy number of viral protein or nucleic acid targets is relatively low.

Late stage replication events include those associated with virus particle assembly and release from the host cell. These viral processes are more difficult targets to develop antiviral reagents. This is due in part to the vastly larger number of virus particles that result from active viral replication.

Enveloped virus particles adopt an outer membrane structure composed of the host cell membrane in its final virus form. Examples of enveloped viruses include retroviruses (for example, human immunodeficiency virus, type 1), rhabdoviruses (for example, rabies virus), and herpes viruses (for example, herpes simplex virus, type 1). For enveloped viruses, the final stages of virus replication include envelope maturation, budding and release.

No antiviral therapeutic reagents have been developed that target the processes of enveloped virus budding and release. This is due in large part to the inability to target virus-specific proteins, owing to the large number of viral proteins present during late phase infection. But more importantly, the host cell-virus interactions responsible for enveloped virus particle maturation, budding and release are only poorly understood.

BRIEF SUMMARY OF THE INVENTION

In a first aspect, a compound having an antiviral activity for inhibiting release of an enveloped virus from a cell is disclosed. In one aspect, the compound has an antiviral activity that includes inhibiting formation of an associative complex or disrupting formation of an associative complex. The associative complex comprises an L-domain motif of the enveloped virus and at least one cellular polypeptide, or fragment thereof, capable of binding the L-domain motif of the enveloped virus.

In a second aspect, a method of inhibiting release of an enveloped virus from a cell is disclosed. The method includes the step of contacting the cell with a compound having an antiviral activity. The antiviral activity includes inhibiting formation of an associative complex or disrupting formation of an associative complex. The associative complex comprises an L-domain motif of the enveloped virus and at least one cellular polypeptide, or fragment thereof, capable of binding the L-domain motif of the enveloped virus.

In a third aspect, a pharmaceutical composition comprising a compound having an antiviral activity for inhibiting release of an enveloped virus from a cell and optionally a pharmaceutically acceptable carrier is disclosed.

BRIEF DESCRIPTION OF THE DRAWINGS

The application file contains at least one drawing executed in color. Copies of this patent or patent application publication with color drawing(s) will be provided by the Office upon request and payment of the necessary fee.

FIG. 5A depicts EPIC label-free binding assay data with Celastrol and WWP2 (SEQ ID NO:24).

FIG. 5B depicts EPIC label-free binding assay data with Oxytetracycline and WWP2 (SEQ ID NO:24).

FIG. 5C depicts EPIC label-free binding assay data with Benserazide HCl and WWP2 (SEQ ID NO:24).

DETAILED DESCRIPTION OF THE INVENTION

Disclosed herein are methods and materials to inhibit the interaction of the above-mentioned cellular proteins or fragments thereof with L domain-containing peptides of enveloped viruses. Applicants made the seminal discovery that enveloped viruses use cellular pathways for mediating virus budding and that inhibiting these pathways results in significantly decreased rates of enveloped virus release from cell surfaces. The methods disclosed herein provide a robust, high-throughput approach to identify lead compounds having potent inhibitory effects on enveloped virus protein interactions with the components of these pathways and, thereby, virus particle release.

Figure 1:
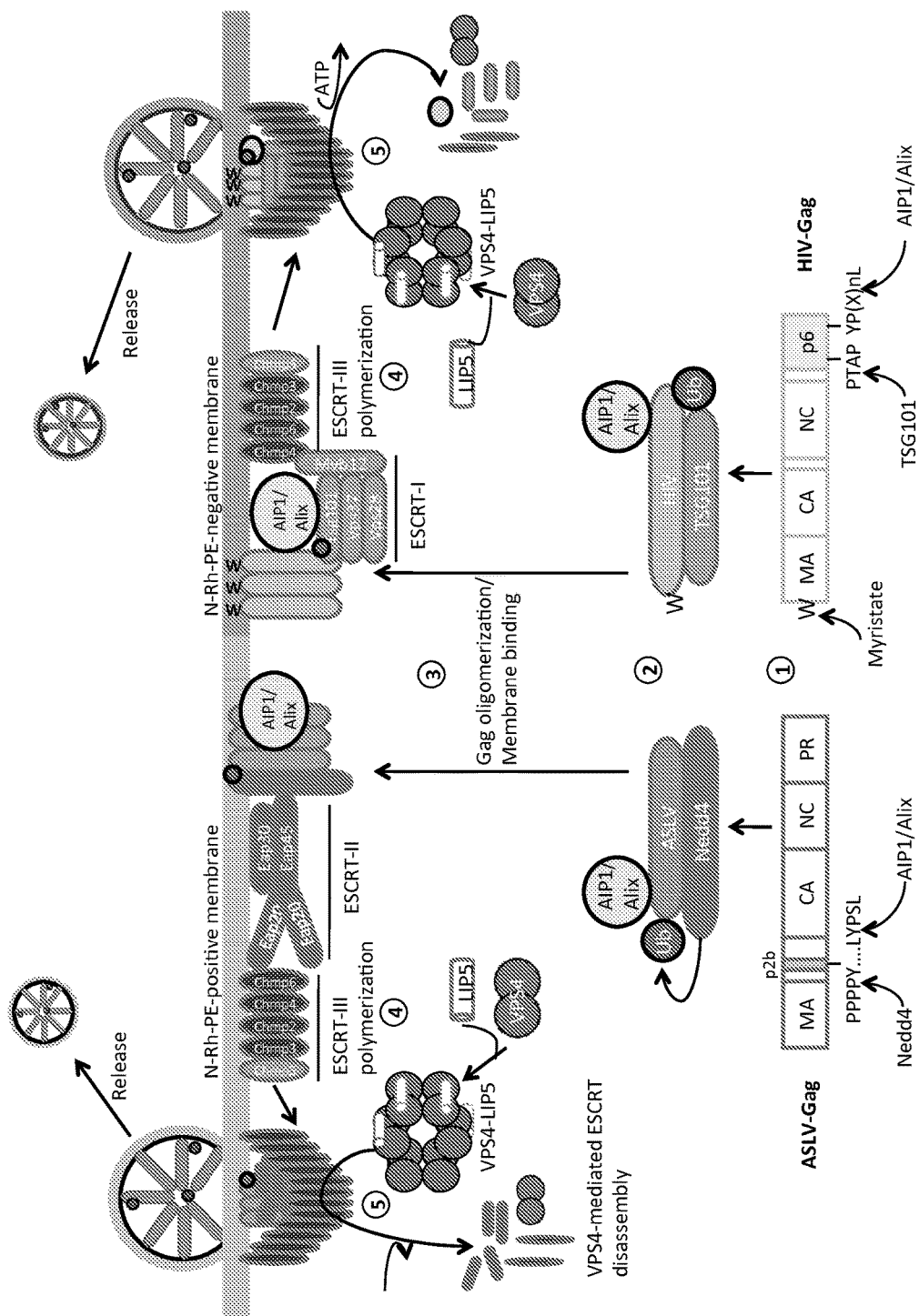
FIG. 1 depicts parallel pathways used by ASLV and HIV-1 Gag to bud from cells.

Referring to FIG. 1, enveloped viruses such as avian sarcoma and leukosis virus (ASLV) and human immunodeficiency virus, type 1 (HIV-1) include late assembly domains ("L-domains") encoded within their Gag protein sequence that interact with cellular components of the endosomal sorting complex required for transport ("ESCRT") machinery for virus budding and release from cells. The L-domains have been identified in a variety of enveloped viruses and families of enveloped viruses. Applicants have identified a consensus subset of L-domain motifs that interact with the critical ESCRT-dependent processes that enveloped viruses use to bud from cell membranes (see Table I, underlined, bold sequences).

TABLE I

L-domains found in enveloped virus proteins.

| Virus species | Virus[1] | Protein | Amino acid sequence containing the L-domain[2] | SEQ ID NO: |
|---|---|---|---|---|
| Arenavirus | LFV | Z | AAPTAPPTGAADSIPPPYSP | 1 |
| | LCMV | Z | TAPSSPPPYEE | 2 |
| Filovirus | EboV | VP40 | MRRVILPTAPPEYMEAI | 3 |
| | MarV | VP40 | NTYMQYLNPPPYADHS | 4 |
| Hepadnavirus | HBV | Core | PPAY | 5 |
| Herpesvirus | HSV-1 | E | PPTY | 6 |
| | HSV-2 | UL56 | PPPY | 7 |
| | CMV | UL32 | PTAP | 8 |
| Paramyxovirus | SV5 | M | QSIKAFPIVINSDG | 9 |
| | MuV | M | RLNAFPIVMGQ | 10 |
| Retrovirus | ASLV | p2B (Gag) | ATASAPPPPYVGSGLYPSL | 11 |
| | HIV-1 | p6 (Gag) | PEPTAPPFLQSRPEPTAPPEES | 12 |
| | HTLV-I | MA (Gag) | DPQIPPPYVEPTAP | 13 |
| | EIAV | p9 (Gag) | QNLYPDLSEIK | 14 |
| Rhabdovirus | VSV | M | LGIAPPPYEEDTSMEYAPSAP | 15 |
| | RV | M | DDLWLPPPEYVPLKEL | 16 |

[1] Virus names corresponding to the abbreviations presented are as follows: LFV, Lassa fever virus; LCMV, lymphocytic choriomeningitis virus; EboV, Ebola virus; MarV, Marberg virus; HBV, hepatitis B virus; HSV-1, Herpes simplex virus, type 1; HSV-2, Herpes simplex virus, type 2; CMV, cytomegalovirus; SV5, Simian virus, type 5; MuV, Mumps virus; ASLV, avian sarcoma leucosis virus; HIV-1, human immunodeficiency virus, type 1; HTLV-I, human T-lymphotrophic virus, type 1; EIAV, equine infectious anemia virus; VSV, vesicular stomatitis virus; and RV, rabies virus.
[2] Underlined, bolded sequences indicate the consensus sequences within the L-domains.

One of these L-domain motifs, termed the PTAP motif (for example, from HIV-1), interacts with the TSG101 protein that becomes recruited as part of the ESCRT complexes. Another of these L-domain motifs, termed PPPY motif (also referred to as the "PY motif" or the "PY L-domain motif;" for example, from ASLV), interacts with the Nedd4 family of proteins that is also recruited by ESCRT-associated proteins. While it is often the case that certain viruses have a viral protein might encode both types of L-domains, typically only one predominates in the viral budding process through interactions with ESCRT machinery. The Applicants have devised novel, robust screening methods to identify compounds that interfere with the interaction between viral L-domains that include the PPPY motif or PTAP motif and ESCRT component, TSG101 or ESCRT-linked component, Nedd4 family proteins. These screening methods enable one to rapidly identify compounds that inhibit the interactions of both Nedd4 and TSG101 with the viral L-domain motifs, thereby providing a high-throughput strategy to obtain candidate lead compounds having utility as novel antiviral agents for inhibiting virus budding and release from infected cells.

Some candidate lead compounds can display potency at inhibiting only Nedd4- or TSG101-mediated ESCRT pathways, thereby offering specific antiviral activity for one type of virus or virus family. Yet other candidate lead compounds can display potency at inhibiting both Nedd4- or TSG101-mediated ESCRT pathways, thereby offering broad-spectrum antiviral activity to a plurality of diverse enveloped virus families. Thus, the screening methods disclosed herein contemplate identification of compounds having either narrow- or broad-spectrum antiviral effects.

Figure 2:
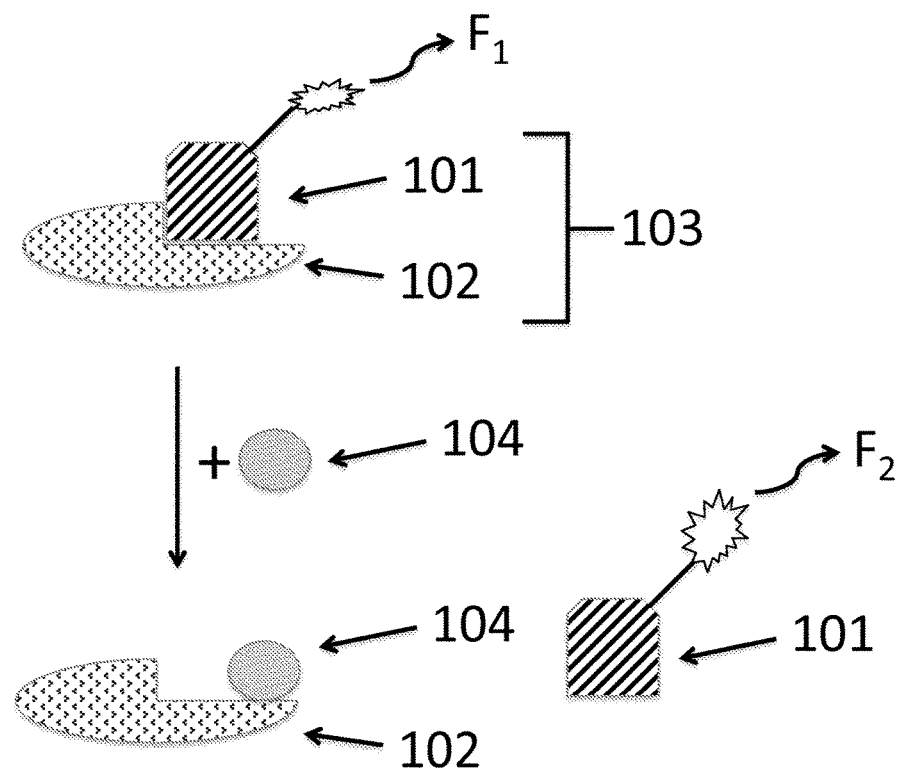
FIG. 2 depicts a first embodiment to screen in vitro for the ability of a test compound (104) to inhibit an associative complex (103) formed between a fluorescently-labeled viral peptide probe (101) containing a viral L-domain motif and a cellular ESCRT complex protein (102). The fluorescence of 101 in 103 is denoted as $F_1$, while the fluorescence of 101 free is denoted as $F_2$. Note that compound 104 need not bind to the same site as probe 101 on protein 102 or that probe 101 need be completely dissociated from 102 to have $F_2$ arise.

One preferred embodiment of such a screening method is depicted in FIG. 2. Briefly, the assay is based upon changes in the fluorescence polarization of a fluorescently-labeled viral peptide probe 101 that includes an L-domain motif in an associative complex 103 with selected cellular ESCRT-associated protein 102 (for example, TSG101 (SEQ ID NOs: 32 or 33) or a Nedd4 family polypeptide (for example, WWP1 (SEQ ID NO:29), WWP2 (SEQ ID NO:24), Nedd4 L, among others), or a fragment thereof) as a function of the presence or absence of test compound 104. Because the associative complex 103 restricts motion of the fluorescently labeled viral peptide probe 101, the latter displays characteristic fluorescent polarization properties (denoted by $F_1$ of FIG. 2). Upon introduction of compound 104 into solutions containing the associative complex 103, an interaction between compound 104 and the associative complex 103 that alters or releases the fluorescently-labeled viral peptide probe 101 will result in a change in fluorescence polarization of the solution (denoted $F_2$ of FIG. 2.)

Permutations and variations of the embodiment of the screening assay (FIG. 2) are recognized to one skilled in the art based upon this disclosure and fall within the scope of the invention. For example, the selection of the fluorescent label and its attachment within probe 101 can be varied, provided that associative complex 103 can form having a discernible fluorescence polarization signal. For example labels can be introduced at the amino terminus, the carboxy terminus or at suitable locations within the peptide probe using coupling chemistries that are well known in the art. In particular, the type of fluorescent label selected will depend upon a variety of factors, such as whether the spectral properties of the label can be discerned under assay conditions such as the presence of fluorescent species derived from assays components like the viral peptide sequences that form probe 101, the selected cellular ESCRT protein 102, and the test compound 104.

Likewise, the preferred choices of the viral peptide sequences for inclusion in probe 101 are routine in nature, as are the preferred choices of whether a single copy or a plurality of copies of said viral sequences are to be included in probe 101. For example, three tandemly-linked copies of the PPPY motif from the Δp2b Gag protein of ALSV (for example, SEQ ID NO:17) provided a $K_d$ of 0.20 μM for the WWP2 polypeptide (SEQ ID NO:24), as compared to the corresponding monomer that had a $K_d$ of 18 μM. Though any specific viral peptide sequence can be included in probe 101, preferred embodiments include L-domain motifs, including those of Table I (SEQ ID NOS: 1-16) and ESCRT-linked protein (for example, Nedd4 family polypeptides (for example, WWP1 (SEQ ID NO:29), WWP2 (SEQ ID NO:24), Nedd4 L, among others) and TSG101 polypeptide, or a fragment thereof), binding variants thereof, as well as others known in the art.

Furthermore, additional representative viral L-domain motifs can be identified from a variety of viruses belonging to different enveloped virus families using standard biochemical and molecular techniques. These L-domain motifs can be screened using modifications of the assay presented in FIG. 2. Representative viruses for this purpose include Lassa fever virus; lymphocytic choriomeningitis virus; Ebola virus; Marberg virus; West Nile Virus; hepatitis B virus; Herpes simplex virus, type 1; Herpes simplex virus, type 2; cytomegalovirus; Simian virus, type 5; Mumps virus; avian sarcoma leucosis virus; human immunodeficiency virus, type 1; human T-lymphotrophic virus, type 1; equine infectious anemia virus; vesicular stomatitis virus; and rabies virus, among others.

Likewise, the choice of cellular ESCRT component polypeptides of Nedd4 family members (for example, WWP1 (SEQ ID NO:29), WWP2 (SEQ ID NO:24), Nedd4 L, among others) and TSG101 depends upon the solubility attributes of the selected protein. For example, while the recombinant Nedd4 polypeptides are soluble under assay conditions, the full-length TSG101 was not. In the case of conducting this screening assay with TSG101, a soluble recombinant polypeptide fragment derived from the full-length protein having the binding domain for the viral L-domain motifs was prepared and used for screening assays (See SEQ ID NO:33, Table VI). One particularly sensitive assay for detecting candidate inhibitor interactions with TSG101 (SEQ ID NO:33) is based upon the ability of the candidate to alter the thermal denaturation profile of protein folding for a soluble fragment of TSG101 peptide (SEQ ID NO:33), as assessed by fluorescence methods. These assays and other aspects are described in detail in the Examples.

A high-throughput assay using the screening method of FIG. 2 was devised to screen a library of 70,000 compounds for the ability to disrupt complexes formed between Nedd4 WWP2 (SEQ ID NO:24) and the ASLV L-domain motif containing PPPY (for example, SEQ ID NO: 17). The results of this initial screen (for example with FITC-labeled probe 101 (SEQ ID NO:18)) yielded about 700 candidate compounds having the desired molecular inhibitory properties. Owing to the possibility of false-positives arising in these assays, the initial collection candidate compounds are rescreened in a secondary assay fitted with viral probe 101 containing a different fluorescent label (for example, with TAMRA-labeled probe 101 (SEQ ID NO:19)). The results of the secondary screen with the identified collection of 700 compounds provided a further reduction of viable candidates to 130 compounds having properties for inhibiting virus release from cells.

Figure 3:
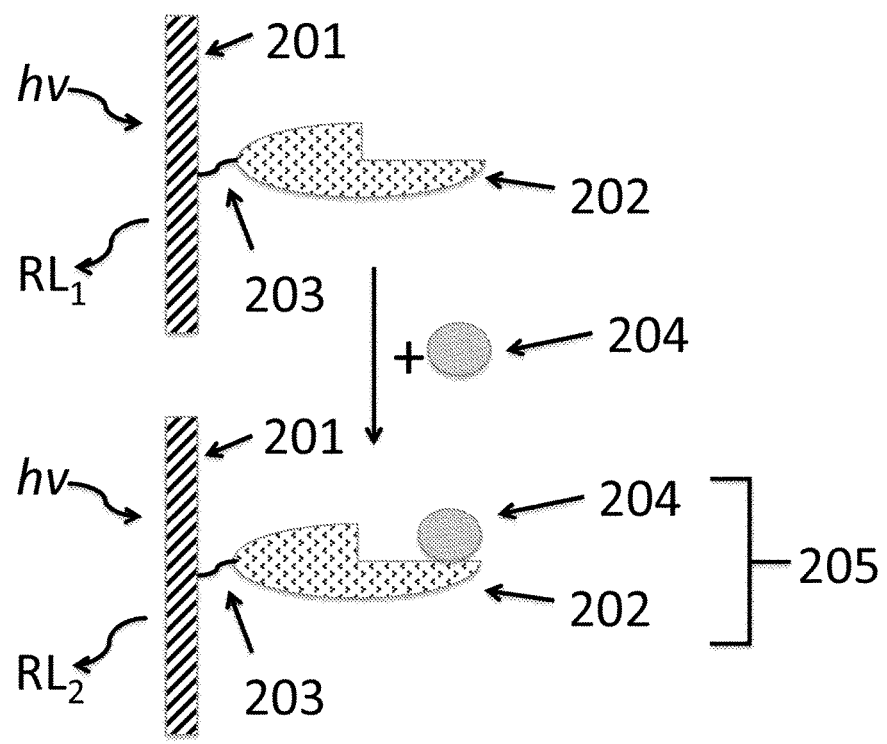
FIG. 3 depicts a second embodiment to screen in vitro for the ability of a test compound (204) to bind to a cellular ESCRT complex protein (202) that is immobilized to substrate (201) via a linking group (203). The assay measures changes in the index of refraction upon a binding event (205) by comparing the wavelength of the reflected light ($RL_1$) in the absence of 204 to the wavelength of the reflected light ($RL_2$) in the presence of 204.

Another preferred embodiment of an in vitro screening method is depicted in FIG. 3. In this method, the ability of the candidate compound 204 to directly interact with the cellular ESCRT-linked component protein (for example, Nedd4 family of polypeptides [for example, WWP1 (SEQ ID NO:29), WWP2 (SEQ ID NO:24), Nedd4 L, among others]) or TGS101 is evaluated. According to this embodiment, a cellular ESCRT component protein 202 is preferably immobilized to a substrate 201 (for example, a microtiter plate) via a linking group 203 (for example, an amine group). The substrate preferably includes an optional reference area that provides a control to prevent non-specific interactions with non-mobilized ESCRT complex protein 202 with substrate 201. The substrate 201 is washed and irradiated with broadband light so that a baseline refractive index is measured. Test compound 204 is added to the system to permit its binding to the immobilized ESCRT component protein 202 to form a resultant associative complex 205. The substrate 201 is irradiated with broadband light again to detect a change in the wavelength of the reflected light.

Commercial instruments are available to enable high-throughput screening of test compounds 204 for their ability to bind ESCRT component protein 202 (for example, TSG101 (SEQ ID NOs: 32 or 33) or a Nedd4 family polypeptide (for example, WWP1 (SEQ ID NO:29), WWP2 (SEQ ID NO:24), Nedd4 L, among others)) for example, the Epic® technology; PerkinElmer, Inc. (Watham, Mass.)). As will be apparent to one skilled in the art, either the ESCRT component protein 202 or the test compound 204 may be immobilized to substrate 201. However, it is preferable to immobilize ESCRT component protein 202 to provide a high-throughput platform for screening a plurality of test compounds 204 in parallel for their ability to form associative complex 205. These assays and other aspects are described in detail in the Examples.

This screening method can be used in conjunction with the method outlined in FIG. 2 to further refine the collection of identified compounds to identify those that directly interact with ESCRT component polypeptides. For example, the screening method was applied to 30 candidates from the collection of 130 compounds identified previously to provide seven compounds having the ability to bind directly to Nedd4 family polypeptides in the micromolar range of inhibitor compound concentrations. As further described below, two of these compounds were found to be non-toxic to cultured cells and were capable of blocking PPPPY-dependent virus-like particle (VLP) budding and release from cells.

The advantages of performing the screening method of FIG. 3 (relative, for example, to the embodiment illustrated in FIG. 2) is that one can measure direct binding interactions between test compounds 204 and ESCRT component proteins 202 in a label-free assay. In addition to being able to detect direct biomolecular interactions between test compounds 204 and ESCRT component proteins 202, one can rapidly perform thermodynamic measurements of the binding interaction (for example, $K_d$ determinations) resulting in formation of associative complex 205. This latter advantage can provide an estimate of whether certain compounds (204) display viable binding properties supportive of continuing on with biological testing of the compounds in viral inhibition studies.

FTS Assay for Detecting Direct Binding Interactions Between Test Compounds and ESCRT Component Proteins.

The fluorescence-based thermal shift assay is based on the observation that a protein unfolds upon heating, exposing the hydrophobic residues within its tertiary structure. The unfolding temperature ($T_m$) is determined by the protein's primary sequence and solution environment. The FTS assay uses a fluorescent dye sensitive to a hydrophobic environment to probe protein stability and its modulation by small molecule ligands. The dye has a low fluorescence quantum yield when in a polar environment. Once in contact with the hydrophobic core normally buried within a folded protein that has become exposed during the thermal unfolding (melting) process, the quantum yield of the dye increases, thus providing a reporting signal. Furthermore, a protein's stability can be affected by ligand binding, resulting in an increase or decrease in its melting temperature. FTS assay uses the Tm shift upon binding of a ligand to identify hit compounds for drug discovery. See Pantoliano M W, Petrella E C, Kwasnoski J D, Lobanov V S, Myslik J, Graf E, Carver T, Asel E, Springer B A, Lane P, Salemme F R. (2001) High-density miniaturized thermal shift assays as a general strategy for drug discovery. J Biomol Screen 6: 429-440; Lo M C, Aulabaugh A, Jin G, Cowling R, Bard J, et al. (2004) Evaluation of fluorescence-based thermal shift assays for hit identification in drug discovery. Anal Biochem 332: 153-159, which are incorporated by reference in their entireties.

Figure 4:
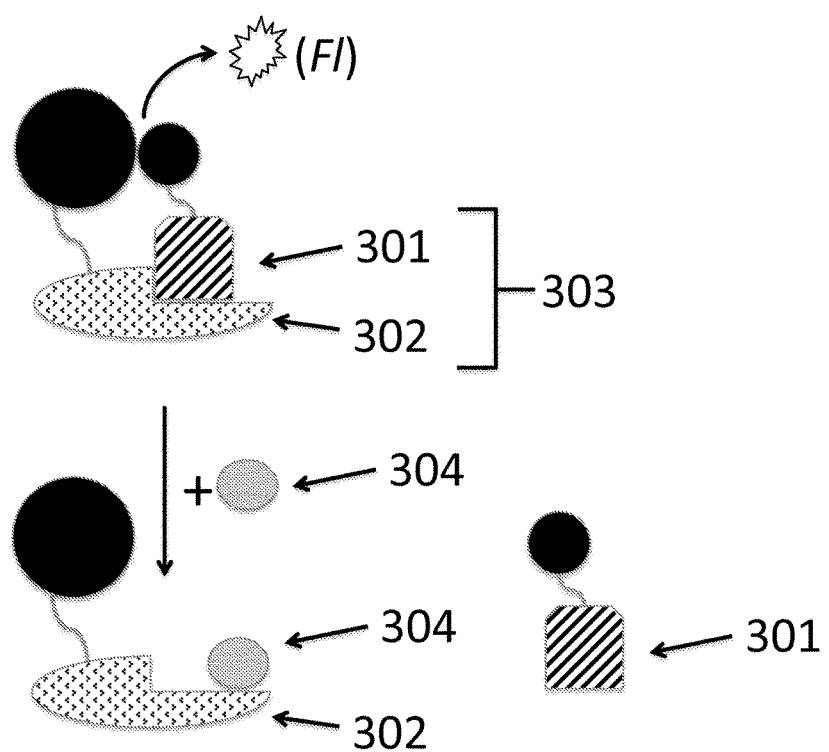
FIG. 4 depicts a third embodiment to screen in vivo for the ability of a test compound (304) to inhibit a reconstituted EGFP two-hybrid complex (303) formed between a partial N-terminal fusion EGFP polypeptide (denoted by small ball) that includes a viral peptide (301) containing a viral L-domain motif and a complementary partial C-terminal EGFP fusion polypeptide that includes a cellular ESCRT complex protein or a viral L-domain binding domain derived therefrom (302). The reconstituted EGFP complex 303 produces the fluorescence (Fl) analogous to native EGFP when 301 and 302 interact in vivo. If test compound 304 interferes with formation of 403, the cells produce less fluorescence.
Figure 6A:
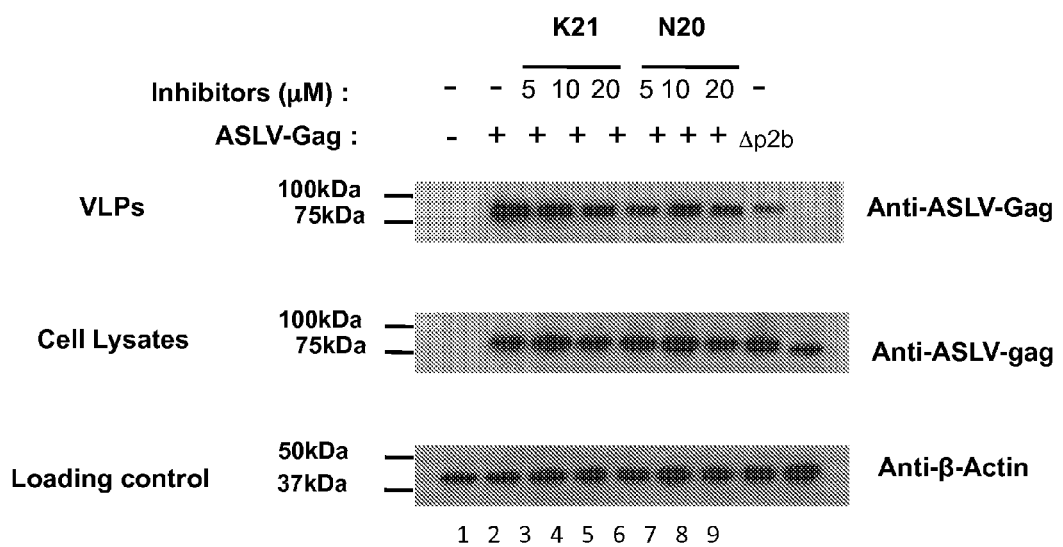
FIG. 6A depicts an exemplary assay that shows the effect of small molecule inhibitors targeting Nedd4 interaction with PPPY-containing viral Gag motif L-domain on the release of ASLV virus like particles (VLPs) from 293 cells, as adjudged by Western blot assay using an anti-ASLV Gag antibody to detect ASLV Gag protein that remains associated with the cells (cell lysates) or released from cells (VLPs) when 293 cells that express ASLV Gag protein are contacted with no inhibitor or with inhibitors (K21 [Benserazide Hydrochloride] and N20 [Oxytetracycline]) at the indicated concentrations in the media. The ASLV Gag protein denoted as Δp2b contains a deletion of the L-domain motif. The budding defect can be seen by comparing release of VLPs from untreated cells (lane 2) to K21-contacted cells (lanes 3-5) and N20-contacted cells (lanes 6-8). Lane 1 is loading control for untreated cells that do not express ASLV Gag protein. Lane 9 is a control for untreated cells that express ASLV Gag with an L-domain deletion (Δp2b). These inhibitor concentrations are not cell toxic.
Figure 6B:
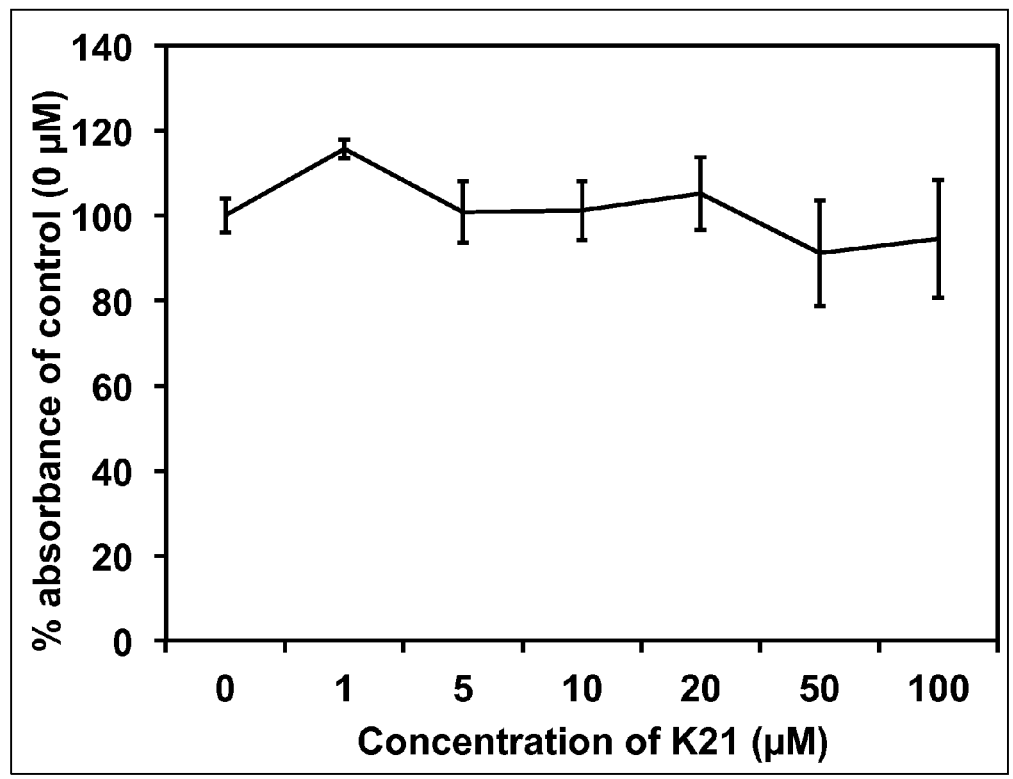
FIG. 6B depicts percentage of absorbance of control (0 μM) as a function of concentration of the inhibitor K21 [Benserazide Hydrochloride] in the media.
Figure 6C:
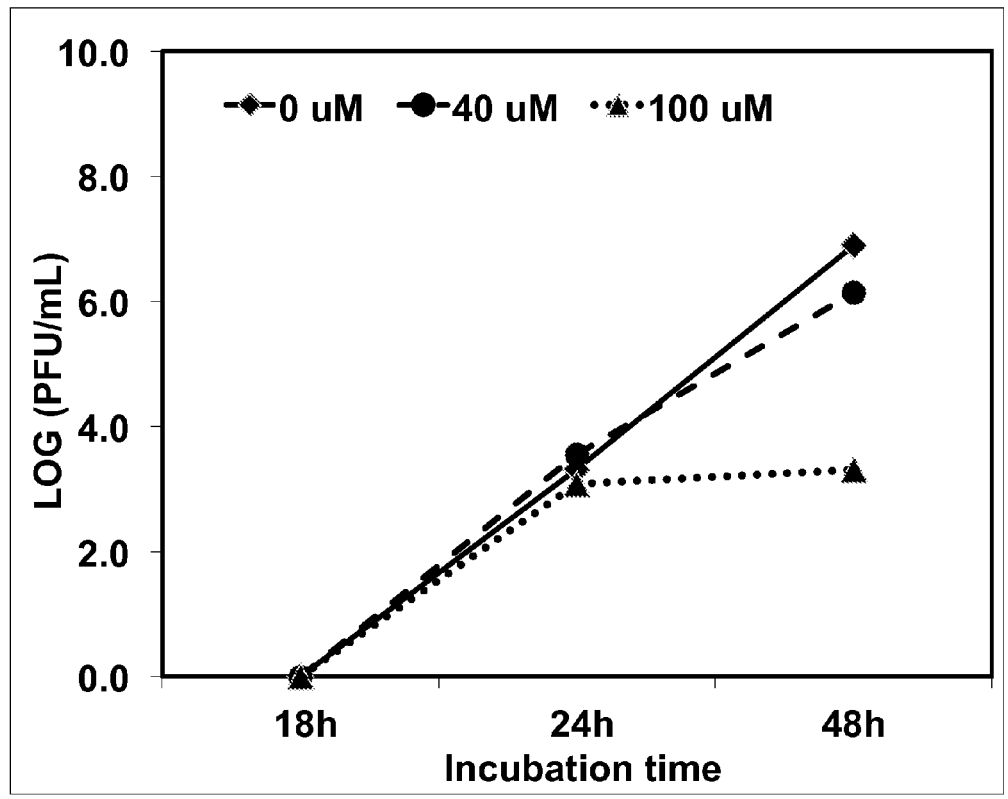
FIG. 6C depicts VLP release (LOG(PFU/ml) as a function of time for the indicated concentrations of the inhibitor K21 [Benserazide Hydrochloride] in the media.
Figure 6D:
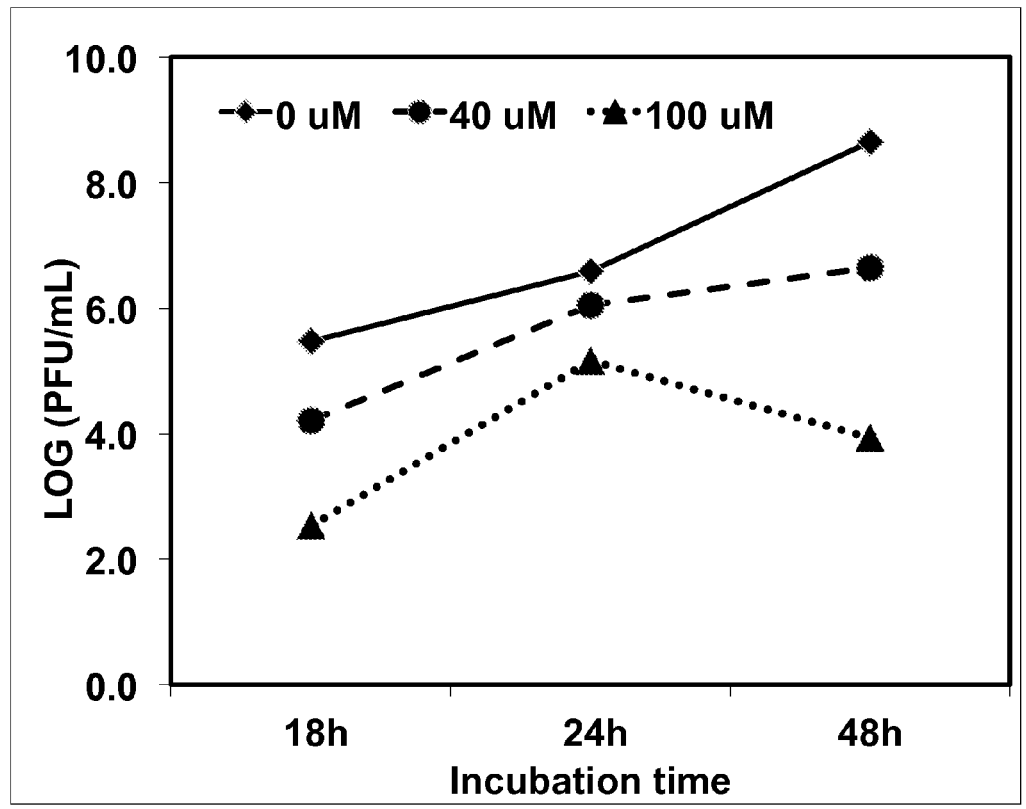
FIG. 6D depicts VLP release (LOG(PFU/ml) as a function of time for the indicated concentrations of the inhibitor K21 [Benserazide Hydrochloride] in the media.

In Vivo Screening Methods-Based Molecular Genetic Assays, Cell-Based VLP Production Assays and Whole-Virus Replication Assays As an alternative or complementary embodiment to the described screening methods in vitro, an in vivo screening method is contemplated as depicted in FIG. 4. In this method, EGFP is genetically engineered as two-half polypeptide gene cassettes (that is, N-terminal portion of EGFP and C-terminal portion of EGFP), which when expressed simultaneously in the cells, fail to provide a functionally reconstituted EGFP having fluorescence properties. The two-half EGFP polypeptide gene cassettes are engineered to include a viral L-domain motif (for examples, a PY motif or a PTAP motif) in one of the EGPF cassettes (see FIG. 4, 301) and a cellular ESCRT component protein (for example, a Nedd4 family polypeptide or a TSG101 polypeptide or fragment thereof (SEQ ID NOs: 32 or 33)) in the other EGFP cassette (see FIG. 4, 302). When cells are co-transfected with expression vectors containing half-EGFP gene cassettes, the corresponding fusion proteins are expressed to enable reconstitution of EGFP functional activity via interaction between the two heterologous fusion partners, the viral L-domain motif and the corresponding ESCRT complex polypeptide in the form of an associative complex (see FIG. 4, 303). Cells (either transiently or stably expressing the EGFP constructs) can be evaluated using test compounds (see FIG. 4, 304) to assess whether the compounds reduce cellular fluorescence. These assays and other aspects are described in detail in the Examples.

Candidate compounds having an inhibitory effect of fluorescence have also been evaluated for their ability to interfere with normal cellular physiology and growth by, for example, determining cytotoxicity profiles of the compounds as a function of dose response and incubation time with the cells. One advantage of the in vivo assay is that it provides additional opportunities to survey test compounds that otherwise might not be possible with the aforementioned biochemical assays (for example, with assays involving certain ESCRT component polypeptides having limited solubility in vitro). Other further advantages of in vivo assays of this sort is that they can provide a useful model for studying compound transport and clearance in cells as would be important for determining ADME profiles (for examples, bioactivity, bioavailability, bio-inactivation, among others) at a cellular level, as well as provide additional confirmatory evidence of the biological potency of the compounds in a more meaningful, biological context.

For candidate lead compounds identified through one or more of the aforementioned screening methods, biological assays have been established to evaluate the specific antiviral inhibitory effects the compounds have on virus budding and release. In one assay, virus like particle ("VLP") production can be evaluated as a function of test compound dose. For example, human 293 cells can permit use of ASLV gag expression systems to study viral protein expression and VLP production as a function of test compound dose response. Likewise, human 293 cells can be used to follow VLP production with HIV-1 gag expression systems as a function of test compound dose response. Follow-up experiments well within the skilled artisan's grasp include evaluating other aspects of viral replication, as monitored by standard biochemical assays (PCR, RT-PCR, western blot methods and the like) as well as cell toxicity effects. These assays and other aspects are described in detail in the Examples or are otherwise well understood in the art.

VLP production assays have provided evidence of candidate lead compounds showing antiviral inhibitory effect on virus particle release as a function of dose, experiments then can proceed to demonstrate the antiviral effect in whole virus replication assays. Three preferred whole virus replication assay systems include the rhabdovirus VSV replication system, the herpes virus KSHV replication system, HSV-1 replication assay in Vero cells, and HIV-1 virus replication system with assays in the physiological host, i.e., CD4+ T cells. These assays and other aspects are described in detail in the Examples.

The aforementioned in vitro and in vivo screening methods can be combined either in series or in parallel (and in any order) to identify compounds having either narrow-spectrum activity against a few viruses or broad-spectrum antiviral activity against many different viruses. For example, lead compounds identified that interact with Nedd4 family members can be evaluated for their ability to interact with TSG101 or to disrupt TSG101—viral L-domain interactions. In this manner, different antiviral compounds can be discerned having discrete types of inhibitory activity. Further, one can identify gradients of antiviral potency across entire classes of viruses by evaluating the dose response profiles in a combination of biochemical and biological assays with different virus families having different viral L-domain motifs, as described herein. Moreover, combinations of compounds have TSG101-specific inhibitory activity and Nedd4 family-specific inhibitory activity can be tested against virus infection to determine whether the drug combinations block virus access to the ESCRT-complex dependent pathways are blocked for enveloped virus release.

These approaches have clear utility for two simple reasons. First, L-domains encoding the aforementioned PY motifs and PTAP motifs can be found with viral proteins for single virus families. Thus, viruses having both types of L-domains can potentially utilize both pathways mediated by Nedd 4 and TSG101. Second, the L-domains used by viruses are interchangeable. Thus, there is a need for compounds to disrupt both interactions between viral L-domains with the two different pathways mediated by Nedd 4 and TSG101, wherein virus budding and release can occur from different cellular membranes.

The identified compound inhibitors have utility as antiviral therapeutic agents. The therapy is a post infection treatment that will slow down the spread of virus by preventing particles from releasing from infected cell surfaces. The accumulation of particles will enhance detection by the immune system, which will clear the infection. The human body already has an innate immunity response that targets the release of virus particles late in infection. Thus, the above approach has viability because it will complement the natural immunity mechanism.

By using the in vivo screening assays described herein, several compounds have been identified having inhibitory effects on viral L-domain motif interaction with ESCRT component polypeptides, or in the alternative, having the capability to bind directly to the ESCRT component polypeptides. These compounds are listed in Tables II-IV.

TABLE II

Candidate compounds that inhibit viral budding and release.

| Compound | Assay Identification[1] | Relevant Property[2] |
|---|---|---|
| NSC306711; 813419-93-1 | FP Assay (FITC/TAMRA); Epic; VLP-ASLV | 1 μM |
| NSC128437 | FP Assay (FITC/TAMRA); Epic Assay | 3 μM |

TABLE II-continued

Candidate compounds that inhibit viral budding and release.

| Compound | Assay Identification[1] | Relevant Property[2] |
|---|---|---|
| CD27-G10 | FP Assay (FITC/TAMRA); Epic Assay | 1 μM |
| CD23-G07 | FP Assay (FITC/TAMRA); Epic Assay | 20-30 μM |
| CD15-B10 | FP Assay (FITC/TAMRA); Epic Assay | |

[1] Assays used include the fluorescence polarization assay ("FP Assay") with SEQ ID NO: 17 coupled to either a FITC label (SEQ ID NO: 18) or a TAMRA label (SEQ ID NO: 19) ("FITC/TMR"); label-free, refractive index assay ("Epic Assay").
[2] Relevant property is [compound] to achieve 50% change in fluorescence polarization in FP Assay.

Candidate compound NSC306711; 813419-93-1 has the following structure (I):

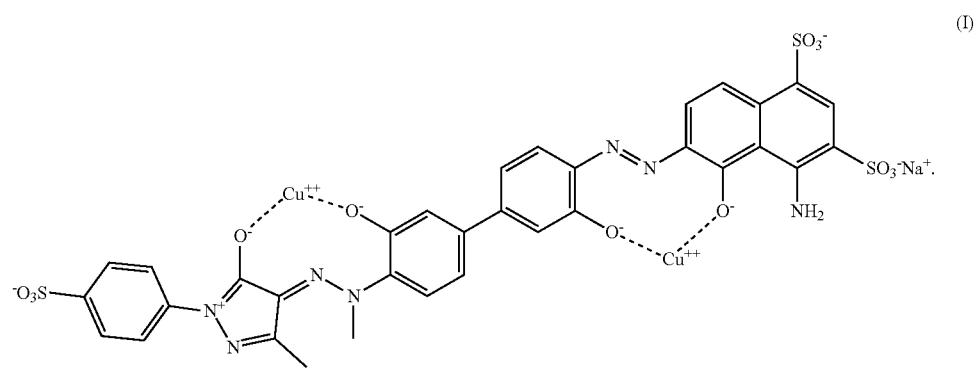

Candidate compound NSC128437 has the following structure (II):

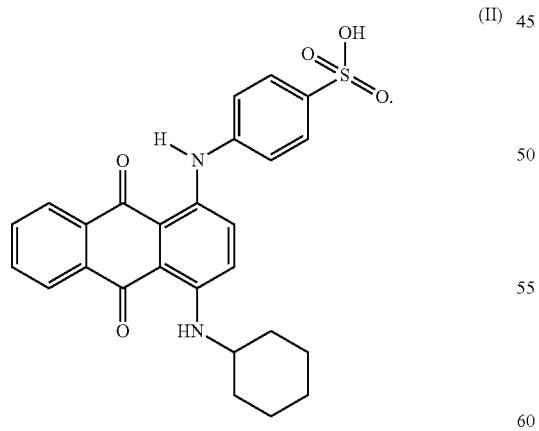

Candidate compound CD27-G10 has the following structure (III):

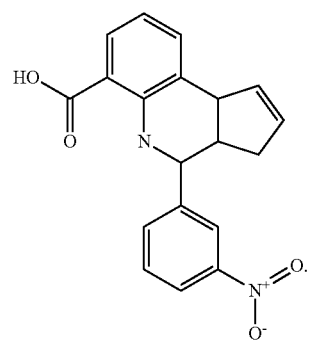

CD27-G10
106D05

Candidate compound CD23-G07 has the following structure (IV):

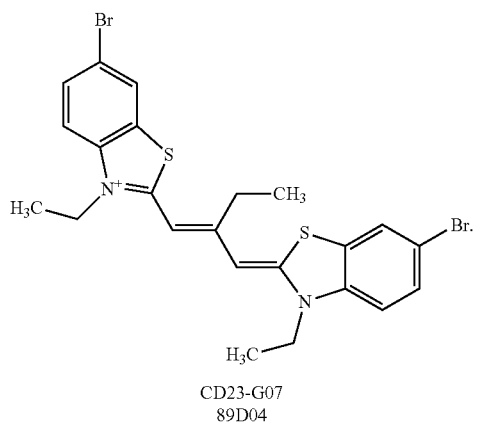

CD23-G07
89D04

Additional candidate compounds were identified with the fluorescence polarization assay and Epic label-free binding assay using WWP2 (SEQ ID NO:24) as the target. These candidate compounds and their properties are presented in Table III. The respective binding assays using the Epic label-free system are depicted in FIG. 5.

Candidate compound CD15-B10 has the following structure (V):

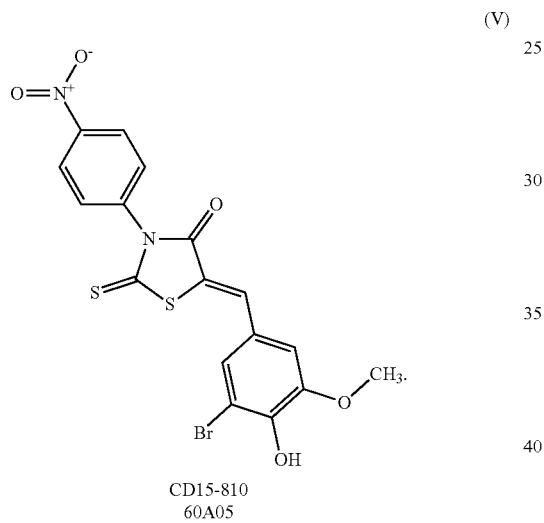

CD15-810
60A05

TABLE III

Candidate compounds that inhibit PY-motif interactions with WWP2

| Kd (μM) | IUPAC Name (Common Name) | CAS Reg. No. | Structure |
|---|---|---|---|
| 18.5 | 3-Hydroxy-9β,13α-dimethyl-2-oxo-24,25,26-trinoroleana-1(10),3,5,7-tetraen-29-oic acid (Celastrol) | 34157-83-0 | (VI) |

TABLE III-continued

Candidate compounds that inhibit PY-motif interactions with WWP2

| Kd (μM) | IUPAC Name (Common Name) | CAS Reg. No. | Structure |
|---|---|---|---|
| 10.6 | (4S,4aR,5S,5aR,6S,12aS)-4-(dimethylamino)-3,5,6,10,11,12a-hexahydroxy-6-methyl-1,12-dioxo-1,4,4a,5,5a,6,12,12a-octahydrotetracene-2-carboxamide (Oxytetracycline) | 79-57-2 | 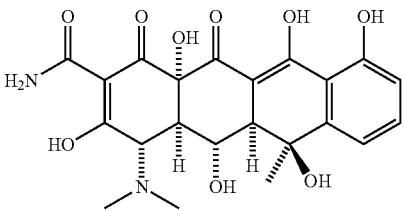 (VII) |
| 7.9 | (RS)-2-amino-3-hydroxy-N'-(2,3,4-trihydroxybenzyl)propanehydrazide hydrochloride (Benserazide Hydrochloride) | 322-35-0 | 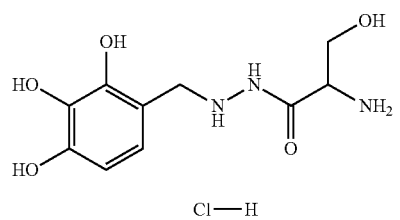 (VIII) |

Figure 7:
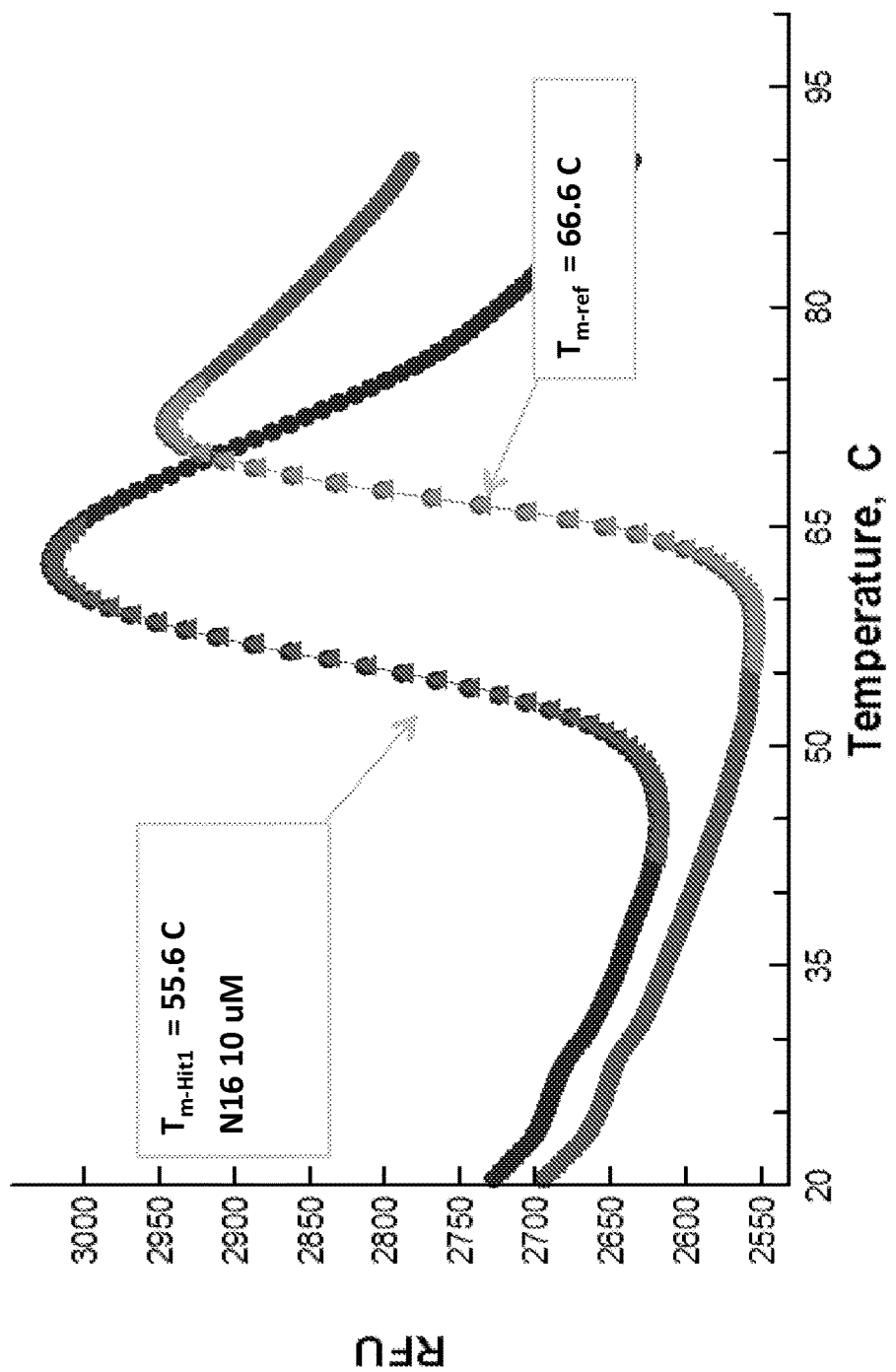
FIG. 7 depicts an fluorescence-based thermal shift (FTS) assay to detect a thermal shift in protein folding of TSG101 (SEQ ID NO:33) due to the presence of inhibitor compound N16. In this case, the inhibitor compound induced thermal instability, resulting in a lower $T_m$ for protein unfolding.

Additional candidate compounds were identified with the fluorescence polarization assay and Epic label-free binding assay using a soluble fragment of TSG101 (SEQ ID NO:33) as the target. These candidate compounds and their properties are presented in Table IV. The fluorescence-based thermal shift assay is another exemplary binding assay for identifying lead candidates (FIG. 7).

TABLE IV

Candidate compounds that inhibit PTAP-motif interactions with TSG101 (SEQ ID NO: 33)

| IUPAC Name (Common Name) | CAS Reg. No. | Structure |
|---|---|---|
| 5-methoxy-2-[(R)-[(4-methoxy-3,5-dimethypyridin-2-yl)methane]sulfinyl]-1H-1,3-benzodiazole, potassium (Esomeprazole potassium) | 161796-78-7 | 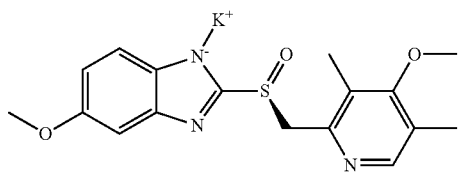 (IX) |
| (RS)-3-Methoxy-8-[(4-methoxy-3,5-dimethyl-pyridin-2-yl)methylsulfinyl]-2,7,9-triazabicyclo[4.3.0]nona-2,4,8,10-tetraene (Tenatoprazole) | 113712-98-4 | 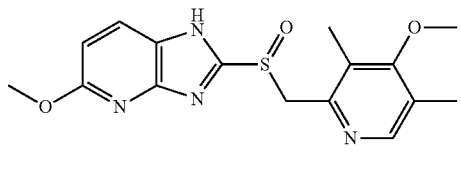 (X) |
| 2-Phenyl-1,2-benzoselenazol-3-one (Ebselen) | 6090-34-3 | 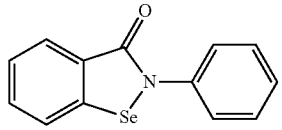 (XI) |

TABLE IV-continued

Candidate compounds that inhibit PTAP-motif interactions with TSG101 (SEQ ID NO: 33)

| IUPAC Name (Common Name) | CAS Reg. No. | Structure |
|---|---|---|
| (4E)-5-Methyl-2-phenyl-4-{[(2,4,6-tribromophenyl)-amino]methylene}-2,4-dihydro-3H-pyrazole-3-thione | | 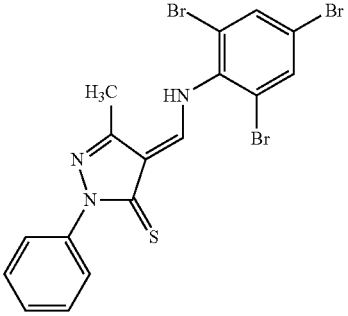 (XII) |
| [4-{[(4-Methylphenyl)-sulfonyl]amino}-3,6-dihydro-1,3,5-triazin-1(2H)-yl]acetic acid | | 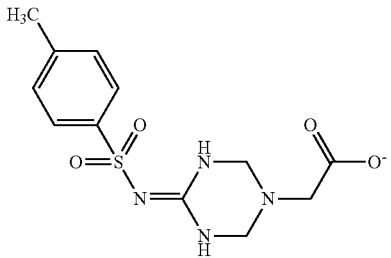 (XIII) |

These compounds were further evaluated as antiviral inhibitors of virus budding and release using the methods disclosed herein. Cultured T cells contacted with either Benserazide Hydrochloride (K21) or Oxytetracycline (N20) [candidate PY-binding motif inhibitors against the Nedd 4 peptide family members] and then subsequently infected with HIV-1 display significant reduction in HIV-1 particle release, as adjudged by detection of HIV-1 CA protein in the cell culture media by ELISA (see Table V).

TABLE V

Activity of compounds to Inhibit HIV-1 release from T-Cells in culture

| Compound | [Compound][1] | HIV-1 CA protein in culture media[2] |
|---|---|---|
| None | 0 μM | 3.2 ng/mL |
| Benserazide Hydrochloride | 100 μM | 0.46 ng/mL |
| Oxytetracycline | 20 μM | 1.9 ng/mL |

[1]Indicated inhibitor concentrations tested are not toxic to the contacted cells.
[2]Results averaged for six experiments, as detected by ELISA.

Vero cells were inoculated with HSV-1 (strain F) at a multiplicity of infection (MOI) of 0.01 for 2 hr. The cells were washed and treated with 0.10 M sodium citrate buffer to inactivate viruses on the outside of the cells (for example, in the culture medium). The culture medium was replaced with fresh culture medium containing no inhibitor compound or different concentrations (40 μM or 80 μM) of inhibitor compounds F15 or N16 (candidate PTAP motif inhibitors against the TSG101 peptide [SEQ ID NO:33]) for 48 hr. The supernatants (culture medium) and total cells (culture medium and cells) were collected for determining infectious virus titer. The virus titers were determined by standard plaque assay on Vero cells.

Figure 8A:
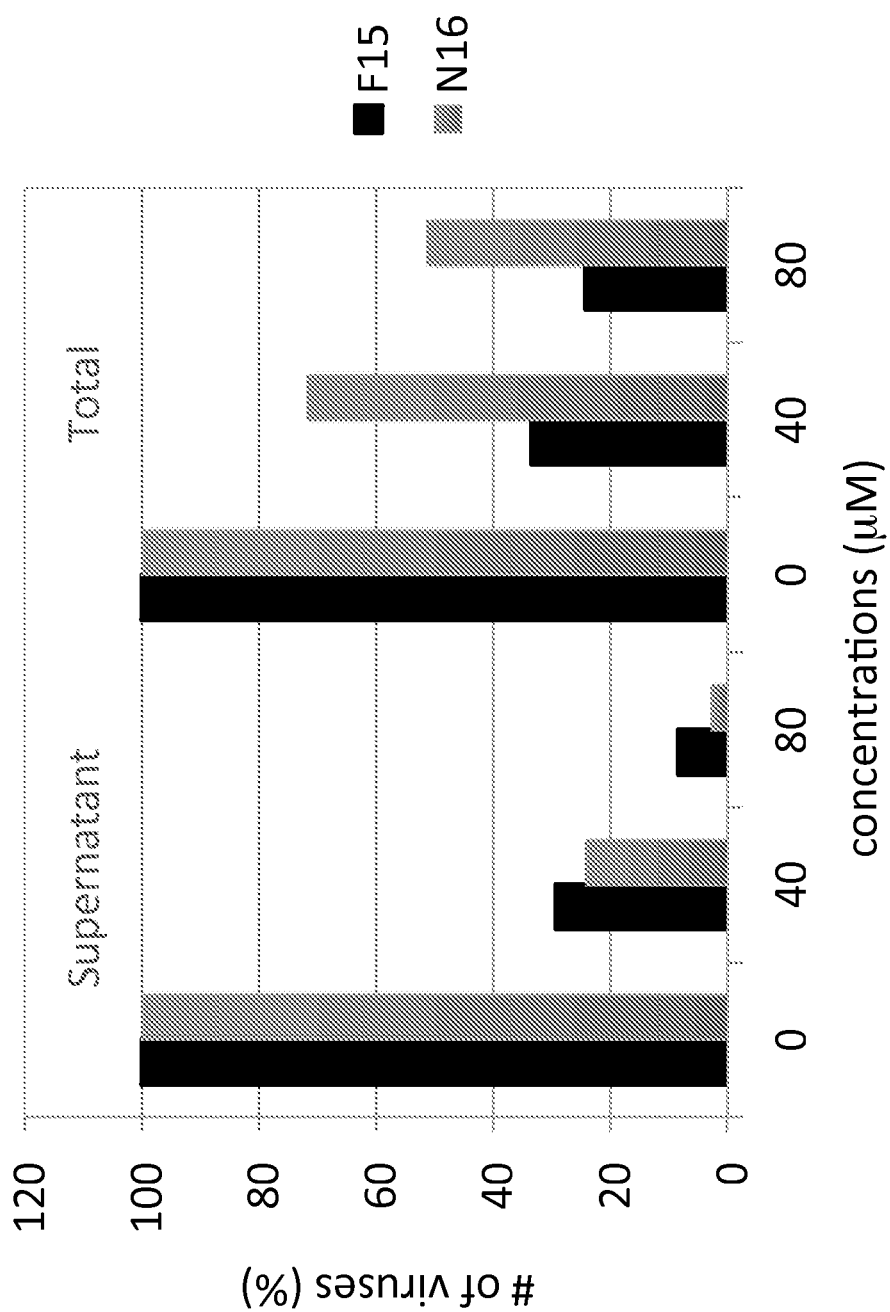
FIG. 8A depicts results of infectious HSV-1 virion production from HSV-1 infected VERO cells alone or HSV-1 infected VERO cells contacted with PTAP-motif inhibitor compounds, F15 (Esomeprazole potassium) and N16, at the indicated concentrations. The titers of infectious HSV-1 virus particles was determined from plaque assays with naïve (uninfected) VERO cell cultures infected with virions harvested from either the cultured cell media containing the VERO cells contacted with no inhibitor compound or with one of compounds F15 or N16 ("supernatant"), or from both the cultured cell media and the VERO cells contacted no inhibitor compound or with one of compounds F15 or N16 ("total"). The indicated concentrations of the PTAP-motif inhibitor compounds, F15 and N16, are not toxic to the contacted VERO cells.

As shown in FIG. 8A, inhibitor compound F15 (Esomeprazole potassium) reduced infectious HSV-1 virion release from HSV-1 infected cells by more than 90% as compared to infected cells not contacted with an inhibitor compound at the higher concentration tested (80 μM) Inhibitor compound F15 (Esomeprazole potassium) also reduced the total load of infectious virions produced in the cells, whether released or not from the cells, by more than 75% relative to that observed with infected cells not contacted with an inhibitor compound at the higher concentration tested (80 μM).

Still referring to FIG. 8A, inhibitor compound N16 (Tenatoprazole) reduced infectious HSV-1 virion release from HSV-1 infected cells by more than 95% as compared to infected cells not contacted with an inhibitor compound at the higher concentration tested (80 μM). Thus, inhibitor compound N16 was slightly more effective than F15 at reducing infectious virion particle release from HSV-1 infected cells at the concentrations tested.

Furthermore, the inhibitor compounds disrupted infectious particle assembly for virions that remained associated with cells in an unreleased state (FIG. 8A). Thus, the inhibitor compounds F15 and N16 were demonstrated to inhibit HSV-1 virion release from cells.

Figure 8B:
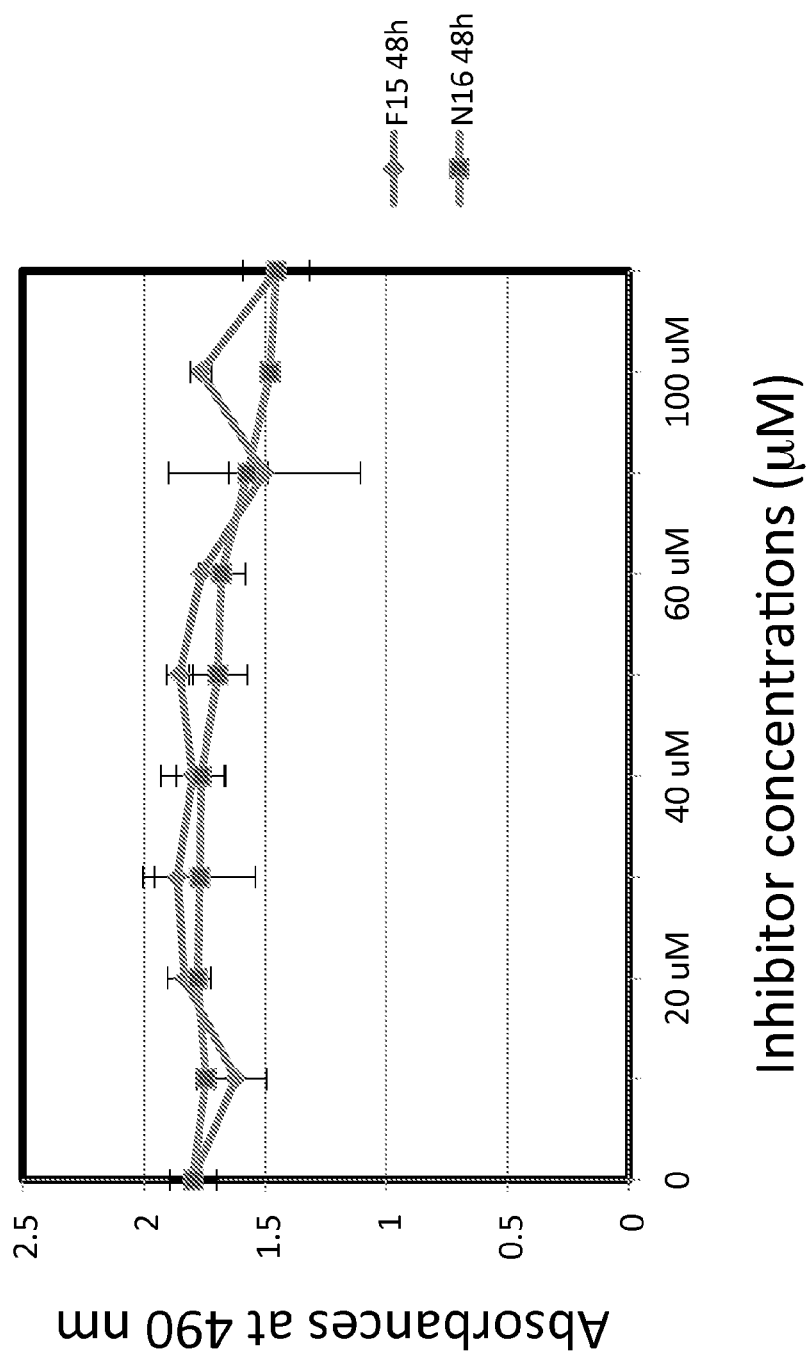
FIG. 8B depicts results of MTS-based assays for evaluating cytotoxicity of cells contacted with the PTAP-motif inhibitor compounds, F15 and N16, where Absorbance at 490 nm (indicative of cell viability) is plotted as a function of inhibitor concentration present in cell culture medium in contact with the cells.

To rule out the possibility that the reduced infectious virion production was attributed to the inhibitor compounds exhibiting a general cytotoxic effect on the host cells, cytotoxicity assays were performed on uninfected cells, wherein the cells were contacted with culture medium containing the inhibitor compounds in a concentration range from 0 µM to 100 µM. As shown in FIG. 8B, the two evaluated inhibitor compounds, F15 and N16, did not display cytotoxic effects on the Vero cells at the concentrations tested.

Thus, the methods disclosed herein can provide compounds having antiviral activity for inhibiting envelope virus release from cells. Moreover, the methods provided herein can identify compounds having antiviral activity for inhibiting formation of or disrupting an associative complex, wherein the associative complex comprises an isolated enveloped virus L-domain motif and at least one isolated cellular polypeptide, or fragment thereof, capable of binding the isolated virus L-domain motif. Furthermore the disclosed methods can yield compounds having binding affinity for at least one isolated cellular polypeptide, or fragment thereof, capable of binding the isolated virus L-domain motif.

Pharmaceutical Compositions

Pharmaceutical compositions comprising a compound having an antiviral activity for inhibiting release of an enveloped virus from a cell are contemplated herein. Such compositions can include pharmaceutically acceptable carrier. Such carriers are amenable for enhancing one or more ADME characteristics, including solubility and bioavailability of compound inhibitors in physiologically acceptable or suitable media systems or biological fluids. For example, compound inhibitors having poor solubility can be encapsulated in nanoparticles or vesicles comprising at least one micelle-forming lipid. Examples of such delivery systems are disclosed in the literature, as exemplified by one or more of the following citations, the contents of each of which are hereby incorporated by reference in their entireties: U.S. Pat. Publication No. US2002/0099164 A1 to Watterson et al.; U.S. Pat. Publication No. US2008/0008749 A1 to Pearlman et al.; and U.S. Pat. Publication No. US2013/0164379 A1 to Gartel et al.

Exemplary pharmaceutical compositions are well known in the art and fully amenable for use with the present compound inhibitors described herein. See, for example, U.S. Pat. No. 8,202,553 to Lan et al., the contents of which are hereby incorporated by reference in its entirety.

EXAMPLES

Example 1

Materials and Methods

Expression and Purification of Nedd4 Related Proteins

Construction and purification of WWP2 protein. The WWP2 encoding gene was excised by EcoR1 and Xho1 (NEB) cleavage from WWP2_pCNA3.1 construct and was ligated to pET28b(+) His-tag plasmid (Novagen) by using T4 DNA ligase (NEB) in 50 mM Tris-HCL (pH 7.5), 10 mM $MgCl_2$, 10 mM dithiothreitol, 1 mM ATP, 25 mg/ml bovine serum albumin at 16° C. overnight. E. coli. BL21 DE3 cells (Invitrogen) were transformed with WWP2_pET28b and were expressed protein by 0.1 mM (final) IPTG induction for 3 hrs at 25° C. His-tagged WWP2 proteins were purified with His-Bind column (Novagen). Proteins were purified by manufacturer's protocol. Cells were lysed by sonication for 2 min at 4° C. in the presence of 1× binding buffer (20 mM Tris-HCl, 0.5 M NaCl, 5 mM Imidazole, pH 7.9) with a proteinase inhibitor cocktail-EDTA free (Roche), 0.1% NP40, and 1 mM PMSF. The cell debris and inclusion bodies were pelleted by centrifugation at 9000 rpm for 8 min. The supernatant fraction was then passed through a 0.45 µm filter and loaded onto a $Ni^{+2}$-NTA His-Bind column at 4° C. The column was washed with Binding buffer (10 times bed volume of resin) followed by an equivalent amount of Wash buffer (20 mM Tris-HCl, 0.5 M NaCl, 60 mM Imidazole, pH 7.9). Poly His containing protein could be eluted with Elute buffer (20 mM Tris-HCl, 0.5 M NaCl, 1 M Imidazole, pH 7.9) and dialyzes against 1× binding buffer without imidazole.

However, to remove the poly His sequence to yield a native protein, the column was instead washed with 10 times the bed volume with thrombin cleavage buffer (20 mM Tris-HCl, pH7.5, 150 mM NaCl, 2.5 mM $CaCl_2$). Then 1 bed volume of biotinylated thrombin solution (1 u/mg of protein, Novagen) was added and the column incubated at room temperature overnight. Untagged proteins were eluted by thrombin cleavage buffer. The biotinylated thrombins were cleared by steptaviding agarose (supplied in the Novagen Thrombin cleavage kit) using a ratio of 16-µl resin per unit of enzyme. Finally, proteins were dialyzed with 1× binding buffer without imidazole. Uncleaved protein could be recovered from the column as above. The nucleotide and amino acid sequence of the WWP2 recombinant protein are shown in Table VI.

TABLE VI

Nucleotide and amino acid sequences for WWP2 recombinant protein

| SEQ ID NO: | Sequence[1] |
|---|---|
| 23 | gaattcggcttcgggatccaccATGGATTACAAGGATGACGACGATAAGATGGCATCTG<br>CCAGCTCTAGCCGGGCAGGAGTGGCCCTGCCTTTTGAGAAGTCTCAGCT<br>CACTTTGAAAGTGGTGTCCGCAAAGCCCAAGGTGCATAATCGTCAACC<br>TCGAATTAACTCCTACGTGGAGGTGGCGGTGGATGGACTCCCCAGTGA<br>GACCAAGAAGACTGGGAAGCGCATTGGGAGCTCTGAGCTTCTCTGGAA<br>TGAGATCATCATTTTGAATGTCACGGCACAGAGTCATTTAGATTTAAAG<br>GTCTGGAGCTGCCATACCTTGAGAAATGAACTGCTAGGCACCGCATCT<br>GTCAACCTCTCCAACGTCTTGAAGAACAATGGGGGCAAAATGGAGAAC<br>ATGCAGCTGACCCTGAACCTGCAGACGGAGAACAAAGGCAGCGTTGTC<br>TCAGGCGGAGAGCTGACAATTTTCCTGCGGGCCAACTGTTGATCTG<br>GGAAATGTGCCTAATGGCAGTGCCCTGACAGATGGATCACAGCTGCCT<br>TCGAGAGACTCCAGTGGAACAGCAGTAGCTCCAGAGAACCGGCACCAG<br>CCCCCCAGCACAAACTGCTTTGGTGGAAGATCCCGGACGCACAGACAT<br>TCGGGTGCTTCAGCCAGAACAACCCCAGCAACCGGCGAGCAAAGCCCC<br>GGTGCTCGGAGCCGGCACCGCCAGCCCGTCAAGAACTCAGGCCACAGT |

TABLE VI-continued

Nucleotide and amino acid sequences for WWP2 recombinant protein

| SEQ ID NO: | Sequence[1] |
|---|---|
| | GGCTTGGCCAATGGCACAGTGAATGATGAACCCACAACAGCCACTGAT<br>CCCGAAGAACCTTCCGTTGTTGGTGTGACGTCCCCACCTGCTGCACCCT<br>TGAGTGTGACCCCGAATCCCAACACGACTTCTCTCCCTGCCCCAGCCAC<br>ACCGGCTGAAGGAGAGGAACCCAGCACTTCGGGTACACAGCAGCTCCC<br>AGCGGCTGCCCAGGCCCCCGACGCTCTGCCTGCTGGATGGGAACAGCG<br>AGAGCTGCCCAACGGACGTGTCTATTATGTTGACCACAATACCAAGAC<br>CACCACCTGGGAGCGGCCCCTTCCTCCAGGCTGGGAAAAACGCACAGA<br>TCCCCGAGGCAGGTTTTACTATGTGGATCACAATACTCGGACCACCACC<br>TGGCAGCGTCCGACCGCGGAGTACGTGCGCAACTATGAGCAGTGGCAG<br>TCGCAGCGGAATCAGCTCCAGGGGGCCATGCAGCACTTCAGCCAAAGA<br>TTCCTCTACCAGTCTTCGAGTGCTTCGACTGACCATGATCCCCTGGGCC<br>CCCTCCCTCCTGGCTGGGAGAAGAGACAGGACAATGGACGGGTGTATT<br>ACGTGAACCATAACACTCGCACGACCCAGTGGGAGGATCCCCGGACCC<br>AGGGGATGATCCAGGAACCAGCTCTGCCCCCAGGATGGGAGATGAAAT<br>ACACCAGCGAGGGGGTGCGATACTTTGTGGACCACAATACCCGCACCA<br>CCACCTTTAAGGATCCTCGCCCGGGGTTTGAGTCGGGGACGAAGCAAG<br>GTTCCCCTGGTGCTTATGACCGCAGTTTTCGGTGGAAGTATCACCAGTT<br>CCGTTTCCTCTGCCATTCAAATGCCCTACCTAGCCACGTGAAGATCAGC<br>GTTTCCAGGCAGACGCTTTTCGAAGATTCCTTCCAACAGATCATGAACA<br>TGAAACCCTATGACCTGCGCCGCCGGCTCTACATCATCATGCGTGGCGA<br>GGAGGGCCTGGACTATGGGGGCATCGCCAGAGAGTGGTTTTTCCTCCT<br>GTCTCATGAGGTGCTCAACCCTATGTATTGTTTATTTGAATATGCCGGA<br>AAGAACAATTACTGCCTGCAGATCAACCCCGCCTCCTCCATCAACCCG<br>GACCACCTCACCTACTTTCGCTTTATAGGCAGATTCATCGCCATGGCGC<br>TGTACCATGGAAAGTTCATCGACACGGGCTTCACCCTCCCTTTCTACAA<br>GCGGATGCTCAATAAGAGACCAACCCTGAAAGACCTGGAGTCCATTGA<br>CCCTGAGTTCTACAACTCCATTGTCTGGATCAAAGAGAACAACCTGGA<br>AGAATGTGGCCTGGAGCTGTACTTCATCCAGGACATGGAGATACTGGG<br>CAAGGTGACGACCCACGAGCTGAAGGAGGGCGGCGAGAGCATCCGGG<br>TCACAGAGGAGAACAAGGAAGAGTACATCATGCTGCTGACTGACTGGC<br>GTTTCACCCGAGGCGTGGAAGAGCAGACCAAAGCCTTCCTGGATGGCT<br>TCAACGAGGTGGCCCCGCTGGAGTGGCTGCGCTACTTTGACGAGAAAG<br>AGCTGGAGCTGATGCTGTGCGGCATGCAGGAGATAGACATGAGCGACT<br>GGCAGAAGAGCACCATCTACCGGCACTACACCAAGAACAGCAAGCAG<br>ATCCAGTGGTTCTGGCAGGTGGTGAAGGAGATGGACAACGAGAAGAG<br>GATCCGGCTGCTGCAGTTTGTCACCGGTACCTGCCGCCTGCCCGTCGGG<br>GGATTTGCCGAACTCATCGGTAGCAACGGACCACAGAAGTTTTGCATT<br>GACAAAGTTGGCAAGGAAACCTGGCTGCCCAGAAGCCACACCTGCTTC<br>AACCGTCTGGATCTTCCACCCTACAAGAGCTACGAACAGCTGAGAGAG<br>AAGCTGCTGTATGCCATTGAGGAGACCGAGGGCTTTGGACAGGAGTAA<br><u>ctcgag</u> |
| 24 | MDYKDDDDKMASASSSRAGVALPFEKSQLTLKVVSAKPKVHNRQPRINSYVEVAVDGLPS<br>ETKKTGKRIGSSELLWNEIIILNVTAQSHLDLKVWSCHTLRNELLGTASVNLSNVLKNNG<br>GKMENMQLTLNLQTENKGSVVSGGELTIFLDGPTVDLGNVPNGSALTDGSQLPSRDSSGT<br>AVAPENRHQPPSTNCFGGRSRTHRHSGASARTTPATGEQSPGARSRHRQPVKNSGHSGLA<br>NGTVNDEPTTATDPEEPSVVGVTSPPAAPLSVTPNPNTTSLPAPATPAEGEEPSTSGTQQ<br>LPAAAQAPDALPAGWEQRELPNGRVYYVDHNTKTTTWERPLPPGWEKRTDPRGRFYYVDH<br>NTRTTTWQRPTAEYVRNYEQWQSQRNQLQGAMQHFSQRFLYQSSSASTDHDPLGPLPPGW<br>EKRQDNGRVYYVNHNTRTTQWEDPRTQGMIQEPALPPGWENKYTSEGVRYFVDHNTRTTT<br>FKDPRPGFESGTKQGSPGAYDRSFRWKYHQFRFLCHSNALPSHVKISVSRQTLFEDSFQQ<br>IMNMKPYDLRRRLYIIMRGEEGLDYGGIAREWFFLLSHEVLNPMYCLFEYAGKNNYCLQI<br>NPASSINPDHLTYFRFIGRFIAMALYHGKFIDTGFTLPFYKRMLNKRPTLKDLESIDPEF<br>YNSIVWIKENNLEECGLELYFIQDMEILGKVTTHELKEGGESIRVTEENKEEYIMLLTDW<br>RFTRGVEEQTKAFLDGFNEVAPLEWLRYFDEKELELMLCGMQEIDMSDWQKSTIYRHYTK<br>NSKQTQWFWQVVKEMDNEKRIRLLQFVTGTCRLPVGGFAELIGSNGPQKFCIDKVGKETW<br>LPRSHTCFNRLDLPPYKSYEQLREKLLYAIEETEGFGQE |

[1]The upper case nucleotide sequence denotes the recombinant polypeptide coding sequence, wherein the italicized sequence encodes the FLAG tag epitope. The underlined nucleotide sequences at the 5'- and 3'-termini of the nucleotide sequence correspond to the EcoRI and XhoI restriction site sequences for introducing the recombinant insert into the pET28b vector.

The complete sequence of the pET28b expression vector that includes the WWP2 recombinant protein is presented below.

SEQ ID NO: 25:
TGGCGAATGGGACGCGCCCTGTAGCGGCGCATTAAGCGCGGCGGGTGTGGTGGTTACGCGCAGC

-continued

```
GTGACCGCTACACTTGCCAGCGCCCTAGCGCCCGCTCCTTTCGCTTTCTTCCCTTCCTTTCTCG

CCACGTTCGCCGGCTTTCCCCGTCAAGCTCTAAATCGGGGGCTCCCTTTAGGGTTCCGATTTAG

TGCTTTACGGCACCTCGACCCCAAAAAACTTGATTAGGGTGATGGTTCACGTAGTGGGCCATCG

CCCTGATAGACGGTTTTTCGCCCTTTGACGTTGGAGTCCACGTTCTTTAATAGTGGACTCTTGT

TCCAAACTGGAACAACACTCAACCCTATCTCGGTCTATTCTTTTGATTTATAAGGGATTTTGCC

GATTTCGGCCTATTGGTTAAAAAATGAGCTGATTTAACAAAAATTTAACGCGAATTTTAACAAA

ATATTAACGTTTACAATTTCAGGTGGCACTTTTCGGGGAAATGTGCGCGGAACCCCTATTTGTT

TATTTTTCTAAATACATTCAAATATGTATCCGCTCATGAATTAATTCTTAGAAAAACTCATCGA

GCATCAAATGAAACTGCAATTTATTCATATCAGGATTATCAATACCATATTTTTGAAAAAGCCG

TTTCTGTAATGAAGGAGAAAACTCACCGAGGCAGTTCCATAGGATGGCAAGATCCTGGTATCGG

TCTGCGATTCCGACTCGTCCAACATCAATACAACCTATTAATTTCCCCTCGTCAAAAATAAGGT

TATCAAGTGAGAAATCACCATGAGTGACGACTGAATCCGGTGAGAATGGCAAAAGTTTATGCAT

TTCTTTCCAGACTTGTTCAACAGGCCAGCCATTACGCTCGTCATCAAAATCACTCGCATCAACC

AAACCGTTATTCATTCGTGATTGCGCCTGAGCGAGACGAAATACGCGATCGCTGTTAAAAGGAC

AATTACAAACAGGAATCGAATGCAACCGGCGCAGGAACACTGCCAGCGCATCAACAATATTTTC

ACCTGAATCAGGATATTCTTCTAATACCTGGAATGCTGTTTTCCCGGGGATCGCAGTGGTGAGT

AACCATGCATCATCAGGAGTACGGATAAAATGCTTGATGGTCGGAAGAGGCATAAATTCCGTCA

GCCAGTTTAGTCTGACCATCTCATCTGTAACATCATTGGCAACGCTACCTTTGCCATGTTTCAG

AAACAACTCTGGCGCATCGGGCTTCCCATACAATCGATAGATTGTCGCACCTGATTGCCCGACA

TTATCGCGAGCCCATTTATACCCATATAAATCAGCATCCATGTTGGAATTTAATCGCGGCCTAG

AGCAAGACGTTTCCCGTTGAATATGGCTCATAACACCCCTTGTATTACTGTTTATGTAAGCAGA

CAGTTTTATTGTTCATGACCAAAATCCCTTAACGTGAGTTTTCGTTCCACTGAGCGTCAGACCC

CGTAGAAAAGATCAAAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCTACCAACTCTTTTTC

CGAAGGTAACTGGCTTCAGCAGAGCGCAGATACCAAATACTGTCCTTCTAGTGTAGCCGTAGTT

AGGCCACCACTTCAAGAACTCTGTAGCACCGCCTACATACCTCGCTCTGCTAATCCTGTTACCA

GTGGCTGCTGCCAGTGGCGATAAGTCGTGTCTTACCGGGTTGGACTCAAGACGATAGTTACCGG

ATAAGGCGCAGCGGTCGGGCTGAACGGGGGGTTCGTGCACACAGCCCAGCTTGGAGCGAACGAC

CTACACCGAACTGAGATACCTACAGCGTGAGCTATGAGAAAGCGCCACGCTTCCCGAAGGGAGA

AAGGCGGACAGGTATCCGGTAAGCGGCAGGGTCGGAACAGGAGAGCGCACGAGGGAGCTTCCAG

GGGGAAACGCCTGGTATCTTTATAGTCCTGTCGGGTTTCGCCACCTCTGACTTGAGCGTCGATT

TTTGTGATGCTCGTCAGGGGGCGGAGCCTATGGAAAAACGCCAGCAACGCGGCCTTTTTACGG

TTCCTGGCCTTTTGCTGGCCTTTTGCTCACATGTTCTTTCCTGCGTTATCCCCTGATTCTGTGG

ATAACCGTATTACCGCCTTTGAGTGAGCTGATACCGCTCGCCGCAGCCGAACGACCGAGCGCAG

CGAGTCAGTGAGCGAGGAAGCGGAAGAGCGCCTGATGCGGTATTTTCTCCTTACGCATCTGTGC

GGTATTTCACACCGCATATATGGTGCACTCTCAGTACAATCTGCTCTGATGCCGCATAGTTAAG

CCAGTATACACTCCGCTATCGCTACGTGACTGGGTCATGGCTGCGCCCCGACACCCGCCAACAC

CCGCTGACGCGCCCTGACGGGCTTGTCTGCTCCCGGCATCCGCTTACAGACAAGCTGTGACCGT

CTCCGGGAGCTGCATGTGTCAGAGGTTTTCACCGTCATCACCGAAACGCGCGAGGCAGCTGCGG

TAAAGCTCATCAGCGTGGTCGTGAAGCGATTCACAGATGTCTGCCTGTTCATCCGCGTCCAGCT

CGTTGAGTTTCTCCAGAAGCGTTAATGTCTGGCTTCTGATAAAGCGGGCCATGTTAAGGGCGGT
```

-continued

```
TTTTTCCTGTTTGGTCACTGATGCCTCCGTGTAAGGGGGATTTCTGTTCATGGGGGTAATGATA

CCGATGAAACGAGAGAGGATGCTCACGATACGGGTTACTGATGATGAACATGCCCGGTTACTGG

AACGTTGTGAGGGTAAACAACTGGCGGTATGGATGCGGCGGGACCAGAGAAAAATCACTCAGGG

TCAATGCCAGCGCTTCGTTAATACAGATGTAGGTGTTCCACAGGGTAGCCAGCAGCATCCTGCG

ATGCAGATCCGGAACATAATGGTGCAGGGCGCTGACTTCCGCGTTTCCAGACTTTACGAAACAC

GGAAACCGAAGACCATTCATGTTGTTGCTCAGGTCGCAGACGTTTTGCAGCAGCAGTCGCTTCA

CGTTCGCTCGCGTATCGGTGATTCATTCTGCTAACCAGTAAGGCAACCCCGCCAGCCTAGCCGG

GTCCTCAACGACAGGAGCACGATCATGCGCACCCGTGGGGCCGCCATGCCGGCGATAATGGCCT

GCTTCTCGCCGAAACGTTTGGTGGCGGGACCAGTGACGAAGGCTTGAGCGAGGGCGTGCAAGAT

TCCGAATACCGCAAGCGACAGGCCGATCATCGTCGCGCTCCAGCGAAAGCGGTCCTCGCCGAAA

ATGACCCAGAGCGCTGCCGGCACCTGTCCTACGAGTTGCATGATAAAGAAGACAGTCATAAGTG

CGGCGACGATAGTCATGCCCCGCGCCCACCGGAAGGAGCTGACTGGGTTGAAGGCTCTCAAGGG

CATCGGTCGAGATCCCGGTGCCTAATGAGTGAGCTAACTTACATTAATTGCGTTGCGCTCACTG

CCCGCTTTCCAGTCGGGAAACCTGTCGTGCCAGCTGCATTAATGAATCGGCCAACGCGCGGGGA

GAGGCGGTTTGCGTATTGGGCGCCAGGGTGGTTTTTCTTTTCACCAGTGAGACGGGCAACAGCT

GATTGCCCTTCACCGCCTGGCCCTGAGAGAGTTGCAGCAAGCGGTCCACGCTGGTTTGCCCCAG

CAGGCGAAAATCCTGTTTGATGGTGGTTAACGGCGGGATATAACATGAGCTGTCTTCGGTATCG

TCGTATCCCACTACCGAGATATCCGCACCAACGCGCAGCCCGGACTCGGTAATGGCGCGCATTG

CGCCCAGCGCCATCTGATCGTTGGCAACCAGCATCGCAGTGGGAACGATGCCCTCATTCAGCAT

TTGCATGGTTTGTTGAAAACCGGACATGGCACTCCAGTCGCCTTCCCGTTCCGCTATCGGCTGA

ATTTGATTGCGAGTGAGATATTTATGCCAGCCAGCCAGACGCAGACGCGCCGAGACAGAACTTA

ATGGGCCCGCTAACAGCGCGATTTGCTGGTGACCCAATGCGACCAGATGCTCCACGCCCAGTCG

CGTACCGTCTTCATGGGAGAAAATAATACTGTTGATGGGTGTCTGGTCAGAGACATCAAGAAAT

AACGCCGGAACATTAGTGCAGGCAGCTTCCACAGCAATGGCATCCTGGTCATCCAGCGGATAGT

TAATGATCAGCCCACTGACGCGTTGCGCGAGAAGATTGTGCACCGCCGCTTTACAGGCTTCGAC

GCCGCTTCGTTCTACCATCGACACCACCACGCTGGCACCCAGTTGATCGGCGCGAGATTTAATC

GCCGCGACAATTTGCGACGGCGCGTGCAGGGCCAGACTGGAGGTGGCAACGCCAATCAGCAACG

ACTGTTTGCCCGCCAGTTGTTGTGCCACGCGGTTGGGAATGTAATTCAGCTCCGCCATCGCCGC

TTCCACTTTTTCCCGCGTTTTCGCAGAAACGTGGCTGGCCTGGTTCACCACGCGGGAAACGGTC

TGATAAGAGACACCGGCATACTCTGCGACATCGTATAACGTTACTGGTTTCACATTCACCACCC

TGAATTGACTCTCTTCCGGGCGCTATCATGCCATACCGCGAAAGGTTTTGCGCCATTCGATGGT

GTCCGGGATCTCGACGCTCTCCCTTATGCGACTCCTGCATTAGGAAGCAGCCCAGTAGTAGGTT

GAGGCCGTTGAGCACCGCCGCCGCAAGGAATGGTGCATGCAAGGAGATGGCGCCCAACAGTCCC

CCGGCCACGGGGCCTGCCACCATACCCACGCCGAAACAAGCGCTCATGAGCCCGAAGTGGCGAG

CCCGATCTTCCCCATCGGTGATGTCGGCGATATAGGCGCCAGCAACCGCACCTGTGGCGCCGGT

GATGCCGGCCACGATGCGTCCGGCGTAGAGGATCGAGATCTCGATCCCGCGAAATTAATACGAC

TCACTATAGGGGAATTGTGAGCGGATAACAATTCCCCTCTAGAAATAATTTTGTTTAACTTTAA

GAAGGAGATATACCATGGGCAGCAGC<u>CATCATCATCATCATCAT</u>CACAGCAGCGGC<u>CTGGTGCCGCG</u>

<u>CGGCAGCC</u>ATATGGCTAGCATGACTGGTGGACAGCAAATGGGTCGCGGATCCGAATTC*ggcttc*

*gggatccacc*ATGGATTACAAGGATGACGACGATAAG*atggcatctgccagctctagccgggca*
```

-continued

```
ggagtggccctgccttttgagaagtctcagctcactttgaaagtggtgtccgcaaagcccaagg
tgcataatcgtcaacctcgaattaactcctacgtggaggtggcggtggatggactccccagtga
gaccaagaagactgggaagcgcattgggagctctgagcttctctggaatgagatcatcattttg
aatgtcacggcacagagtcatttagatttaaaggtctggagctgccataccttgagaaatgaac
tgctaggcaccgcatctgtcaacctctccaacgtcttgaagaacaatgggggcaaaatggagaa
catgcagctgaccctgaacctgcagacggagaacaaaggcagcgttgtctcaggcggagagctg
acaattttcctggacgggccaactgttgatctgggaaatgtgcctaatggcagtgccctgacag
atggatcacagctgccttcgagagactccagtggaacagcagtagctccagagaaccggcacca
gccccccagcacaaactgctttggtggaagatcccggacgcacagacattcgggtgcttcagcc
agaacaaccccagcaaccggcgagcaaagccccggtgctcggagccggcaccgccagcccgtca
agaactcaggccacagtggcttggccaatggcacagtgaatgatgaacccacaacagccactga
tcccgaagaaccttccgttgttggtgtgacgtccccacctgctgcaccctttgagtgtgaccccg
aatcccaacacgacttctctccctgccccagccacaccggctgaaggagaggaacccagcactt
cgggtacacagcagctcccagcggctgcccaggccccgacgctctgcctgctggatgggaaca
gcgagagctgcccaacggacgtgtctattatgttgaccacaataccaagaccaccacctgggag
cggccccttcctccaggctgggaaaaacgcacagatccccgaggcaggttttactatgtggatc
acaatactcggaccaccacctggcagcgtccgaccgcggagtacgtgcgcaactatgagcagtg
gcagtcgcagcggaatcagctccaggggggccatgcagcacttcagccaaagattcctctaccag
tcttcgagtgcttcgactgaccatgatcccctgggccccctccctcctggctgggagaagagac
aggacaatggacgggtgtattacgtgaaccataacactcgcacgacccagtgggaggatccccg
gacccaggggatgatccaggaaccagctctgcccccaggatgggagatgaaatacaccagcgag
ggggtgcgatactttgtggaccacaatacccgcaccaccacctttaaggatcctcgcccggggt
ttgagtcggggacgaagcaaggttcccctggtgcttatgaccgcagttttcggtggaagtatca
ccagttccgtttcctctgccattcaaatgccctacctagccacgtgaagatcagcgtttccagg
cagacgcttttcgaagattccttccaacagatcatgaacatgaaaccctatgacctgcgccgcc
ggctctacatcatcatgcgtggcgaggagggcctggactatgggggcatcgccagagagtggtt
tttcctcctgtctcatgaggtgctcaaccctatgtattgtttatttgaatatgccggaaagaac
aattactgcctgcagatcaaccccgcctcctccatcaacccggaccacctcacctactttcgct
ttataggcagattcatcgccatggcgctgtaccatggaaagttcatcgacacgggcttcaccct
ccctttctacaagcggatgctcaataagagaccaaccctgaaagacctggagtccattgaccct
gagttctacaactccattgtctggatcaaagagaacaacctggaagaatgtggcctggagctgt
acttcatccaggacatggagatactgggcaaggtgacgacccacgagctgaaggagggcggcga
gagcatccgggtcacagaggagaacaaggaagagtacatcatgctgctgactgactggcgtttc
acccgaggcgtggaagagcagaccaaagccttcctggatggcttcaacgaggtggccccgctgg
agtggctgcgctactttgacgagaaagagctggagctgatgctgtgcggcatgcaggagataga
catgagcgactggcagaagagcaccatctaccggcactacaccaagaacagcaagcagatccag
tggttctggcaggtggtgaaggagatggacaacgagaagaggatccggctgctgcagtttgtca
ccggtacctgccgcctgcccgtcggggggatttgccgaactcatcggtagcaacgaccacagaa
gttttgcattgacaaagttggcaaggaaacctggctgcccagaagccacacctgcttcaaccgt
ctggatcttccacccctacaagagctacgaacagctgagagagaagctgctgtatgccattgagg
agaccgagggctttggacaggagtaaCTCGAGCACCACCACCACCACCACTGAGATCCGGCTGC
```

-continued

TAACAAAGCCCGAAAGGAAGCTGAGTTGGCTGCTGCCACCGCTGAGCAATAACTAGCATAACCC

CTTGGGGCCTCTAAACGGGTCTTGAGGGGTTTTTTGCTGAAAGGAGGAACTATATCCGGAT wherein the bold font denote the locations of the initiator and terminator codons for the recombinant peptide pro-form; the upper case letters denote pET28b vector sequences; the lower case letter denote the WWP2 coding sequences, the single-underlined sequences are the poly-His coding sequences, the double-underlined sequences encode the Thrombin cleavage site, the italicized font includes the FLAG-tag coding sequences in frame with the WWP2 coding sequences as configured in the expression vector, pET28b (Novagen).

Construction and preparation of WWP1 protein. The WWP1 encoding gene was amplified by PCR reaction from FLAG-WWP1_pCNA3.1 construct and was ligated to pET28b(+) His-tag plasmid (Novagen). His-tagged WWP1 plasmids were transformed into BL21 DE3 cells. Protein expression and purification were followed the procedure of WWP2 protein preparation. The WWP1 encoding gene was amplified by PCR reaction using Deep Vent polymerase (NEB) from the FLAG-WWP1_pCNA3.1 construct using the oligodeoxynucleotides 5'-ATAGGATTCATGGCCACT-GCTTCACCAAGGTCT-3' forward primer (SEQ ID NO:26) and 5'-ATAGCGGCCGCTCATTCTTGTC-CAAATCCCTCTGT-3' reverse primer (SEQ ID NO:27) and was ligated to pET28b(+) His-tag plasmid between the EcoR1 and Not cloning sites. The nucleotide and amino acid sequences for WWP1 recombinant protein are illustrated in Table VII.

TABLE VII

Nucleotide and amino acid sequences for WWP1 recombinant protein[1]

| SEQ ID NO: | Sequence[2] |
|---|---|
| 28 | gaattcATGGCCACTGCTTCACCAAGGTCTGATACTAGTAATAACCACAGT GGAAGGTTGCAGTTACAGGTAACTGTTTCTAGTGCCAAACTTAAAAGA AAAAAGAACTGGTTCGGAACAGCAATATATACAGAAGTAGTTGTAGAT GGAGAAATTACGAAAACAGCAAAATCCAGTAGTTCTTCTAATCCAAAA TGGGATGAACAGCTAACTGTAAATGTTACGCCACAGACTACATTGGAA TTTCAAGTTTGGAGCCATCGCACTTTAAAAGCAGATGCTTTATTAGGAA AAGCAACGATAGATTTGAAACAAGCTCTGTTGATACACAATAGAAAAT TGGAAAGAGTGAAAGAACAATTAAAACTTTCCTTGGAAAACAAGAATG GCATAGCACAAACTGGTGAATTGACAGTTGTGCTTGATGGATTGGTGA TTGAGCAAGAAAATATAACAAACTGCAGCTCATCTCCAACCATAGAAA TACAGGAAAATGGTGATGCCTTACATGAAAATGGAGAGCCTTCAGCAA GGACAACTGCCAGGTTGGCTGTTGAAGGCACGAATGGAATAGATAATC ATGTACCTACAAGCACTCTAGTCCAAAACTCATGCTGCTCGTATGTAGT TAATGGAGACAACACACCTTCATCTCCGTCTCAGGTTGCTGCCAGACCC AAAAATACACCAGCTCCAAAACCACTCGCATCTGAGCCTGCCGATGAC ACTGTTAATGGAGAATCATCCTCATTTGCACCAACTGATAATGCGTCTG TCACGGGTACTCCAGTAGTGTCTGAAGAAAATGCCTTGTCTCCAAATTG CACTAGTACTACTGTTGAAGATCCTCCAGTTCAAGAAATACTGACTTCC TCAGAAAACAATGAATGTATTCCTTCTACCAGTGCAGAATTGGAATCTG AAGCTAGAAGTATATTAGAGCCTGACACCTCTAATTCTAGAAGTAGTTC TGCTTTTGAAGCAGCCAAATCAAGACAGCCAGATGGGTGTATGGATCC TGTACGGCAGCAGTCTGGGAATGCCAACACAGAAACCTTGCCATCAGG GTGGGAACAAAGAAAAGATCCTCATGGTAGAACCTATTATGTGGATCA TAATACTCGAACTACCACATGGGAGAGACCACAACCTTTACCTCCAGG TTGGGAAAGAAGAGTTGATGATCGTAGAAGAGTTTATTATGTGGATCA TAACACCAGAACAACAACGTGGCAGCGGCCTACCATGGAATCTGTCCG AAATTTTGAACAGTGGCAATCTCAGCGGAACCAATTGCAGGGAGCTAT GCAACAGTTTAACCAACGATACCTCTATTCGGCTTCAATGTTAGCTGCA GAAAATGACCCTTATGGACCTTTGCCACCAGGCTGGGAAAAAAGAGTG GATTCAACAGACAGGGTTTACTTTGTGAATCATAACACAAAAACAACC CAGTGGGAAGATCCAAGAACTCAAGGCTTACAGAATGAAGAACCCCTG CCAGAAGGCTGGGAAATTAGATATACTCGTGAAGGTGTAAGGTACTTT GTTGATCATAACAAGAACAACAACATTCAAAGATCCTCGCAATGGG AAGTCATCTGTAACTAAAGGTGGTCCACAAATTGCTTATGAACGCGGC TTTAGGTGGAAGCTTGCTCACTTCCGTTATTTGTGCCAGTCTAATGCAC TACCTAGTCATGTAAAGATCAATGTGTCCCGGCAGACATTGTTTGAAGA TTCCTTCCAACAGATTATGGCATTAAAACCCTATGACTTGAGGAGGCGC TTATATGTAATATTTAGAGGAGAAGAAGGACTTGATTATGGTGGCCTA GCGAGAGAATGGTTTTTCTTGCTTTCACATGAAGTTTTGAACCCAATGT ATTGCTTATTTGAGTATGCGGGCAAGAACAACTATTGTCTGCAGATAAA TCCAGCATCAACCATTAATCCAGACCATCTTTCATACTTCTGTTTCATTG GTCGTTTTATTGCCATGGCACTATTTCATGGAAAGTTTATCGATACTGG TTTCTCTTTACCATTCTACAAGCGTATGTTAAGTAAAAAACTTACTATT AAGGATTTGGAATCTATTGATACTGAATTTTATAACTCCCTTATCTGGA TAAGAGATAACAACATTGAAGAATGTGGCTTAGAAATGTACTTTTCTGT TGACATGGAGATTTTGGGAAAAGTTACTTCACATGACCTGAAGTTGGG AGGTTCCAATATTCTGGTGACTGAGGAGAACAAAGATGAATATATTGG TTTAATGACAGAATGGCGTTTTTCTCGAGGAGTACAAGAACAGACCAA |

TABLE VII-continued

Nucleotide and amino acid sequences for WWP1 recombinant protein[1]

SEQ ID NO: Sequence[2]

AGCTTTCCTTGATGGTTTTAATGAAGTTGTTCCTCTTCAGTGGCTACAGT
ACTTCGATGAAAAAGAATTAGAGGTTATGTTGTGTGGCATGCAGGAGG
TTGACTTGGCAGATTGGCAGAGAAATACTGTTTATCGACATTATACAAG
AAACAGCAAGCAAATCATTTGGTTTTGGCAGTTTGTGAAAGAGACAGA
CAATGAAGTAAGAATGCGACTATTGCAGTTCGTCACTGGAACCTGCCG
TTTACCTCTAGGAGGATTTGCTGAGCTCATGGGAAGTAATGGGCCTCAA
AAGTTTTGCATTGAAAAAGTTGGCAAAGACACTTGGTTACCAAGAAGC
CATACATGTTTTAATCGCTTGGATCTACCACCATATAAGAGTTATGAAC
AACTAAAGGAAAAACTTCTTTTTGCAATAGAAGAGACAGAGGGATTTG
GACAAGAATGAgcggccgc 29 MATASPRSDTSNNHSGRLQLQVTVSSAKLKRKKNWFGTAIYTEVVVDGEITKTAKSSSSS
NPKWDEQLTVNVTPQTTLEFQVWSHRTLKADALLGKATIDLKQALLIHNRKLERVKEQLK
LSLENKNGIAQTGELTVVLDGLVIEQENITNCSSSPTIEIQENGDALHENGEPSARTTAR
LAVEGTNGIDNHVPTSTLVQNSCCSYVVNGDNTPSSPSQVAARPKNTPAPKPLASEPADD
TVNGESSSFAPTDNASVTGTPVVSEENALSPNCTSTTVEDPPVQEILTSSENNECIPSTS
AELESEARSILEPDTSNSRSSSAFEAAKSRQPDGCMDPVRQQSGNANTETLPSGWEQRKD
PHGRTYYVDHNTRTTTWERPQPLPPGWERRVDDRRRVYYVDHNTRTTTWQRPTMESVRNF
EQWQSQRNQLQGAMQQFNQRYLYSASMLAAENDPYGPLPPGWEKRVDSTDRVYFVNHNTK
TTQWEDPRTQGLQNEEPLPEGWEIRYTREGVRYFVDHNTRTTTFKDPRNGKSSVTKGGPQ
IAYERGFRWKLAHFRYLCQSNALPSHVKINVSRQTLFEDSFQQIMALKPYDLRRRLYVIF
RGEEGLDYGGLAREWFFLLSHEVLNPMYCLFEYAGKNNYCLQINPASTINPDHLSYFCFI
GRFIAMALFHGKFIDTGFSLPFYKRMLSKKLTIKDLESIDTEFYNSLIWIRDNNIEECGL
EMYFSVDMEILGKVTSHDLKLGGSNILVTEENKDEYIGLMTEWRFSRGVQEQTKAFLDGF
NEVVPLQWLQYFDEKELEVMLCGMQEVDLADWQRNTVYRHYTRNSKQIIWFWQFVKETDN
EVRMRLLQFVTGTCRLPLGGFAELMGSNGPQKFCIEKVGKDTWLPRSHTCFNRLDLPPYK
SYEQLKEKLLFAIEETEGFGQE

[1]Recombinant protein illustrated without the His-tag sequence present (cleaved off).
[2]The upper case nucleotide sequence denotes the recombinant polypeptide coding sequence. The underlined nucleotide sequences at the 5'- and 3'-termini of the nucleotide sequence correspond to the EcoRI and NotI restriction site sequences for introducing the recombinant insert into the pET28b vector.

The complete sequence of the pET28b expression vector that includes the WWP1 recombinant protein is presented below.

SEQ ID NO: 30:
TGGCGAATGGGACGCGCCCTGTAGCGGCGCATTAAGCGCGGCGGGTGTGGTGGTTACGCGCAGC

GTGACCGCTACACTTGCCAGCGCCCTAGCGCCCGCTCCTTTCGCTTTCTTCCCTTCCTTTCTCG

CCACGTTCGCCGGCTTTCCCCGTCAAGCTCTAAATCGGGGGCTCCCTTTAGGGTTCCGATTTAG

TGCTTTACGGCACCTCGACCCCAAAAAACTTGATTAGGGTGATGGTTCACGTAGTGGGCCATCG

CCCTGATAGACGGTTTTTCGCCCTTTGACGTTGGAGTCCACGTTCTTTAATAGTGGACTCTTGT

TCCAAACTGGAACAACACTCAACCCTATCTCGGTCTATTCTTTTGATTTATAAGGGATTTTGCC

GATTTCGGCCTATTGGTTAAAAAATGAGCTGATTTAACAAAAATTTAACGCGAATTTTAACAAA

ATATTAACGTTTACAATTTCAGGTGGCACTTTTCGGGGAAATGTGCGCGGAACCCCTATTTGTT

TATTTTTCTAAATACATTCAAATATGTATCCGCTCATGAATTAATTCTTAGAAAAACTCATCGA

GCATCAAATGAAACTGCAATTTATTCATATCAGGATTATCAATACCATATTTTTGAAAAAGCCG

TTTCTGTAATGAAGGAGAAAACTCACCGAGGCAGTTCCATAGGATGGCAAGATCCTGGTATCGG

TCTGCGATTCCGACTCGTCCAACATCAATACAACCTATTAATTTCCCCTCGTCAAAAATAAGGT

TATCAAGTGAGAAATCACCATGAGTGACGACTGAATCCGGTGAGAATGGCAAAAGTTTATGCAT

TTCTTTCCAGACTTGTTCAACAGGCCAGCCATTACGCTCGTCATCAAAATCACTCGCATCAACC

AAACCGTTATTCATTCGTGATTGCGCCTGAGCGAGACGAAATACGCGATCGCTGTTAAAGGAC

AATTACAAACAGGAATCGAATGCAACCGGCGCAGGAACACTGCCAGCGCATCAACAATATTTTC

-continued

```
ACCTGAATCAGGATATTCTTCTAATACCTGGAATGCTGTTTTCCCGGGGATCGCAGTGGTGAGT

AACCATGCATCATCAGGAGTACGGATAAAATGCTTGATGGTCGGAAGAGGCATAAATTCCGTCA

GCCAGTTTAGTCTGACCATCTCATCTGTAACATCATTGGCAACGCTACCTTTGCCATGTTTCAG

AAACAACTCTGGCGCATCGGGCTTCCCATACAATCGATAGATTGTCGCACCTGATTGCCCGACA

TTATCGCGAGCCCATTTATACCCATATAAATCAGCATCCATGTTGGAATTTAATCGCGGCCTAG

AGCAAGACGTTTCCCGTTGAATATGGCTCATAACACCCCTTGTATTACTGTTTATGTAAGCAGA

CAGTTTTATTGTTCATGACCAAAATCCCTTAACGTGAGTTTTCGTTCCACTGAGCGTCAGACCC

CGTAGAAAAGATCAAAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCTACCAACTCTTTTTC

CGAAGGTAACTGGCTTCAGCAGAGCGCAGATACCAAATACTGTCCTTCTAGTGTAGCCGTAGTT

AGGCCACCACTTCAAGAACTCTGTAGCACCGCCTACATACCTCGCTCTGCTAATCCTGTTACCA

GTGGCTGCTGCCAGTGGCGATAAGTCGTGTCTTACCGGGTTGGACTCAAGACGATAGTTACCGG

ATAAGGCGCAGCGGTCGGGCTGAACGGGGGGTTCGTGCACACAGCCCAGCTTGGAGCGAACGAC

CTACACCGAACTGAGATACCTACAGCGTGAGCTATGAGAAAGCGCCACGCTTCCCGAAGGGAGA

AAGGCGGACAGGTATCCGGTAAGCGGCAGGGTCGGAACAGGAGAGCGCACGAGGGAGCTTCCAG

GGGGAAACGCCTGGTATCTTTATAGTCCTGTCGGGTTTCGCCACCTCTGACTTGAGCGTCGATT

TTTGTGATGCTCGTCAGGGGGCGGAGCCTATGGAAAAACGCCAGCAACGCGGCCTTTTTACGG

TTCCTGGCCTTTTGCTGGCCTTTTGCTCACATGTTCTTTCCTGCGTTATCCCCTGATTCTGTGG

ATAACCGTATTACCGCCTTTGAGTGAGCTGATACCGCTCGCCGCAGCCGAACGACCGAGCGCAG

CGAGTCAGTGAGCGAGGAAGCGGAAGAGCGCCTGATGCGGTATTTTCTCCTTACGCATCTGTGC

GGTATTTCACACCGCATATATGGTGCACTCTCAGTACAATCTGCTCTGATGCCGCATAGTTAAG

CCAGTATACACTCCGCTATCGCTACGTGACTGGGTCATGGCTGCGCCCCGACACCCGCCAACAC

CCGCTGACGCGCCCTGACGGGCTTGTCTGCTCCCGGCATCCGCTTACAGACAAGCTGTGACCGT

CTCCGGGAGCTGCATGTGTCAGAGGTTTTCACCGTCATCACCGAAACGCGCGAGGCAGCTGCGG

TAAAGCTCATCAGCGTGGTCGTGAAGCGATTCACAGATGTCTGCCTGTTCATCCGCGTCCAGCT

CGTTGAGTTTCTCCAGAAGCGTTAATGTCTGGCTTCTGATAAAGCGGGCCATGTTAAGGGCGGT

TTTTTCCTGTTTGGTCACTGATGCCTCCGTGTAAGGGGGATTTCTGTTCATGGGGGTAATGATA

CCGATGAAACGAGAGAGGATGCTCACGATACGGGTTACTGATGATGAACATGCCCGGTTACTGG

AACGTTGTGAGGGTAAACAACTGGCGGTATGGATGCGGCGGGACCAGAGAAAAATCACTCAGGG

TCAATGCCAGCGCTTCGTTAATACAGATGTAGGTGTTCCACAGGGTAGCCAGCAGCATCCTGCG

ATGCAGATCCGGAACATAATGGTGCAGGGCGCTGACTTCCGCGTTTCCAGACTTTACGAAACAC

GGAAACCGAAGACCATTCATGTTGTTGCTCAGGTCGCAGACGTTTTGCAGCAGCAGTCGCTTCA

CGTTCGCTCGCGTATCGGTGATTCATTCTGCTAACCAGTAAGGCAACCCCGCCAGCCTAGCCGG

GTCCTCAACGACAGGAGCACGATCATGCGCACCCGTGGGGCCGCCATGCCGGCGATAATGGCCT

GCTTCTCGCCGAAACGTTTGGTGGCGGGACCAGTGACGAAGGCTTGAGCGAGGGCGTGCAAGAT

TCCGAATACCGCAAGCGACAGGCCGATCATCGTCGCGCTCCAGCGAAAGCGGTCCTCGCCGAAA

ATGACCCAGAGCGCTGCCGGCACCTGTCCTACGAGTTGCATGATAAAGAAGACAGTCATAAGTG

CGGCGACGATAGTCATGCCCCGCGCCCACCGGAAGGAGCTGACTGGGTTGAAGGCTCTCAAGGG

CATCGGTCGAGATCCCGGTGCCTAATGAGTGAGCTAACTTACATTAATTGCGTTGCGCTCACTG

CCCGCTTTCCAGTCGGGAAACCTGTCGTGCCAGCTGCATTAATGAATCGGCCAACGCGCGGGGA

GAGGCGGTTTGCGTATTGGGCGCCAGGGTGGTTTTTCTTTTCACCAGTGAGACGGGCAACAGCT
```

-continued

```
GATTGCCCTTCACCGCCTGGCCCTGAGAGAGTTGCAGCAAGCGGTCCACGCTGGTTTGCCCCAG

CAGGCGAAAATCCTGTTTGATGGTGGTTAACGGCGGGATATAACATGAGCTGTCTTCGGTATCG

TCGTATCCCACTACCGAGATATCCGCACCAACGCGCAGCCCGGACTCGGTAATGGCGCGCATTG

CGCCCAGCGCCATCTGATCGTTGGCAACCAGCATCGCAGTGGGAACGATGCCCTCATTCAGCAT

TTGCATGGTTTGTTGAAAACCGGACATGGCACTCCAGTCGCCTTCCCGTTCCGCTATCGGCTGA

ATTTGATTGCGAGTGAGATATTTATGCCAGCCAGCCAGACGCAGACGCGCCGAGACAGAACTTA

ATGGGCCCGCTAACAGCGCGATTTGCTGGTGACCCAATGCGACCAGATGCTCCACGCCCAGTCG

CGTACCGTCTTCATGGGAGAAAATAATACTGTTGATGGGTGTCTGGTCAGAGACATCAAGAAAT

AACGCCGGAACATTAGTGCAGGCAGCTTCCACAGCAATGGCATCCTGGTCATCCAGCGGATAGT

TAATGATCAGCCCACTGACGCGTTGCGCGAGAAGATTGTGCACCGCCGCTTTACAGGCTTCGAC

GCCGCTTCGTTCTACCATCGACACCACCACGCTGGCACCCAGTTGATCGGCGCGAGATTTAATC

GCCGCGACAATTTGCGACGGCGCGTGCAGGGCCAGACTGGAGGTGGCAACGCCAATCAGCAACG

ACTGTTTGCCCGCCAGTTGTTGTGCCACGCGGTTGGGAATGTAATTCAGCTCCGCCATCGCCGC

TTCCACTTTTTCCCGCGTTTTCGCAGAAACGTGGCTGGCCTGGTTCACCACGCGGGAAACGGTC

TGATAAGAGACACCGGCATACTCTGCGACATCGTATAACGTTACTGGTTTCACATTCACCACCC

TGAATTGACTCTCTTCCGGGCGCTATCATGCCATACCGCGAAAGGTTTTGCGCCATTCGATGGT

GTCCGGGATCTCGACGCTCTCCCTTATGCGACTCCTGCATTAGGAAGCAGCCCAGTAGTAGGTT

GAGGCCGTTGAGCACCGCCGCCGCAAGGAATGGTGCATGCAAGGAGATGGCGCCCAACAGTCCC

CCGGCCACGGGGCCTGCCACCATACCCACGCCGAAACAAGCGCTCATGAGCCCGAAGTGGCGAG

CCCGATCTTCCCCATCGGTGATGTCGGCGATATAGGCGCCAGCAACCGCACCTGTGGCGCCGGT

GATGCCGGCCACGATGCGTCCGGCGTAGAGGATCGAGATCTCGATCCCGCGAAATTAATACGAC

TCACTATAGGGGAATTGTGAGCGGATAACAATTCCCCTCTAGAAATAATTTTGTTTAACTTTAA

GAAGGAGATATACCATGGGCAGCAGC*CATCATCATCATCATCACAGCAGCGGCCTGGTGCCGCG

CGGCAGC*CATATGGCTAGCATGACTGGTGGACAGCAAATGGGTCGCGGATCCGAATTCatggcc actgcttcaccaaggtctgatactagtaataaccacagtggaaggttgcagttacaggtaactg tttctagtgccaaacttaaaagaaaaaagaactggttcggaacagcaatatatacagaagtagt tgtagatggagaaattacgaaaacagcaaaatccagtagttcttctaatccaaaatgggatgaa cagctaactgtaaatgttacgccacagactacattggaatttcaagtttggagccatcgcactt taaaagcagatgctttattaggaaaagcaacgatagatttgaaacaagctctgttgatacacaa tagaaaattggaaagagtgaaagaacaattaaaactttccttggaaaacaagaatggcatagca caaactggtgaattgacagttgtgcttgatggattggtgattgagcaagaaaatataacaaact gcagctcatctccaaccatagaaatacaggaaatggtgatgccttacatgaaaatggagagcc ttcagcaaggacaactgccaggttggctgttgaaggcacgaatggaatagataatcatgtacct acaagcactctagtccaaaactcatgctgctcgtatgtagttaatggagacaacacaccttcat ctccgtctcaggttgctgccagacccaaaaatacaccagctccaaaaccactcgcatctgagcc tgccgatgacactgttaatggagaatcatcctcatttgcaccaactgataatgcgtctgtcacg ggtactccagtagtgtctgaagaaaatgccttgtctccaaattgcactagtactactgttgaag atcctccagttcaagaaatactgacttcctcagaaaacaatgaatgtattccttctaccagtgc agaattggaatctgaagctagaagtatattagagcctgacacctctaattctagaagtagttct gcttttgaagcagccaaatcaagacagccagatgggtgtatggatcctgtacggcagcagtctg
```

-continued

```
ggaatgccaacacagaaaccttgccatcagggtgggaacaaagaaaagatcctcatggtagaac ctattatgtggatcataatactcgaactaccacatgggagagaccacaacctttacctccaggt tgggaaagaagagttgatgatcgtagaagagtttattatgtggatcataacaccagaacaacaa cgtggcagcggcctaccatggaatctgtccgaaattttgaacagtggcaatctcagcggaacca attgcagggagctatgcaacagtttaaccaacgatacctctattcggcttcaatgttagctgca gaaaatgacccttatggacctttgccaccaggctgggaaaaagagtggattcaacagacaggg tttactttgtgaatcataacacaaaaacaacccagtgggaagatccaagaactcaaggcttaca gaatgaagaaccctgccagaaggctgggaaattagatatactcgtgaaggtgtaaggtactttt gttgatcataacacaagaacaacaacattcaaagatcctcgcaatgggaagtcatctgtaacta aaggtggtccacaaattgcttatgaacgcggctttaggtggaagcttgctcacttccgttattt gtgccagtctaatgcactacctagtcatgtaaagatcaatgtgtcccggcagacattgtttgaa gattccttccaacagattatggcattaaaaccctatgacttgaggaggcgcttatatgtaatat ttagaggagaagaaggacttgattatggtggcctagcgagagaatggttttttcttgctttcaca tgaagttttgaacccaatgtattgcttatttgagtatgcgggcaagaacaactattgtctgcag ataaatccagcatcaaccattaatccagaccatctttcatacttctgtttcattggtcgttta ttgccatggcactatttcatggaaagtttatcgatactggtttctctttaccattctacaagcg tatgttaagtaaaaaacttactattaaggatttggaatctattgatactgaattttataactcc cttatctggataagagataacaacattgaagaatgtggcttagaaatgtacttttctgttgaca tggagattttgggaaaagttacttcacatgacctgaagttgggaggttccaatattctggtgac tgaggagaacaaagatgaatatattggtttaatgacagaatggcgttttctcgaggagtacaa gaacagaccaaagctttccttgatggttttaatgaagttgttcctcttcagtggctacagtact tcgatgaaaagaattagaggttatgttgtgtggcatgcaggaggttgacttggcagattggca gagaaatactgtttatcgacattatacaagaaacagcaagcaaatcatttggttttggcagttt gtgaaagagacagacaatgaagtaagaatgcgactattgcagttcgtcactggaacctgccgtt tacctctaggaggattttgctgagctcatgggaagtaatgggcctcaaaagttttgcattgaaaa agttggcaaagacacttggttaccaagaagccatacatgttttaatcgcttggatctaccacca tataagagttatgaacaactaaaggaaaaacttcttttttgcaatagaagagacagagggatttg gacaagaatgaGCGGCCGCACTCGAGCACCACCACCACCACCACTGAGATCCGGCTGCTAACAA

AGCCCGAAAGGAAGCTGAGTTGGCTGCTGCCACCGCTGAGCAATAACTAGCATAACCCCTTGGG

GCCTCTAAACGGGTCTTGAGGGGTTTTTGCTGAAAGGAGGAACTATATCCGGAT
``` wherein the bold font denote the locations of the initiator and terminator codons for the recombinant peptide pro-form; the upper case letters denote pET28b vector sequences; the lower case letter denote the WWP1 coding sequences, the italicized font includes the leader peptide coding sequence that includes a polyhistidine motif and thrombin cleavage site derived from the expression vector, pET28b (Novagen).

Example 2

Screening for Small Molecule Compounds that Disrupt the Binding of Nedd4 Proteins to the PY Motif Fluorescent Polarization Assay (FPA) to detect binding of the Nedd4 proteins WWP1/2 to peptides containing the PY L-domain motif sequences: The FPA uses a fluorescein labeled peptide (FTIC-peptide) probe with three tandem PY motif binding units (FITC-ATASAPPPYVGSGGGA-TASAPPPYVGSGGGATASAPPPYVGSGGGRRR-OH, Biosynthesis, TX (SEQ ID NO: 18); (SEQ ID NO: 17 corresponds to SEQ ID NO: 18 without the N-terminal FITC moiety) derived from the p2 region of avian sarcoma/leucosis virus (ASLV) gag gene. With the tandem probe, a Kd of 0.2 µM was obtained from WWP2 protein dose-response study with highest protein concentration at 19.6 µM and FITC-peptide probe concentration of 5 nM. In contrast, Kd value for the probe with a single binding unit is >15 mM. Screens for compounds that disrupt the binding of the FTIC-peptide and WWP2 (SEQ ID NO:24) were carried out in 384-well plate format with 25 ml assay volume at ~0.5 mM WWP2. Non-binding solid black plates (Corning Costar 3575) were used. The assay buffer contained 20 mM Tris and 150 mM NaCl at pH 7.9. FP was measured on either a Biotek Synergy4 or an Analyst GT plate reader. Data analysis was performed using the in-house software excelHTS. The typical Z value of a screen plate was greater than 0.7. Each assay plate included 16 negative control wells containing protein-probe mix but no compounds and 16 wells containing only probe. The difference in FP values of these wells was used as 100% readout signal to calculate the percentage of inhibition of a compound well.

The FTIC-labeled probe was premixed at a concentration of 20 nM with WWP1/2 protein at 0.5 mM. Then 25 ml of the protein-probe mix was added to assay plates by using a ViaFill dispenser. A Labcyte Echo550 acoustic transfer robot was used to transfer compounds (30 to 100 nl, equal to 10 to 50 mM) to the assay plates. The plates were shaken to ensure proper assay mix. Then FP was measured on an Analyst GT plate reader equipped with a plate stacker so that data of multiple plates were recorded in a single file to facilitate data reduction and analysis. The first read was performed one hour after compound addition then the plates were sealed and stored at 4° C. overnight before reading again after 18 hours.

Hit confirmation by TAMRA-probe in dose-response format. The primary hits include false positives due to experimental error and fluorescent compounds that fluoresce or absorb in the FTIC emission range. After primary screen, a hit confirmation screen was performed using TAMRA-probe in dose-response format to rid false positives. TAMRA excites and emits at a longer wavelength range than FITC. The false positives caused by overlap of excitation/emission wavelengths of FITC and some fluorescent compounds can be delineated.

Example 3

Screening for Small Molecule Compounds that Bind to Nedd4 Proteins

Epic label-free assay procedure to measure binding of compounds to WWP2/1: High sensitivity biochemical plates (PerkinElmer Cat. No. 6057468) are used in WWP2 (SEQ ID NO:24) binding assay to maximize protein immobilization. The plate was activated before use with 10 µl of 200 mM EDC (N-(3-dimethylaminopropyl)-N'-ethylcarbodiimide hydrochloride) (Sigma Cat. No. 03449)/50 mM sulfo-NHS (N-hydroxysulfosuccinimide) (Pierce Cat. No. 24510) diluted in H₂O. After 30 min incubation at room temperature, the plates are washed 3 times with 25 µl H₂O and then centrifuged inverted at 800 RPM for 1 min. WWP2 (SEQ ID NO:24) immobilization was accomplished by adding 10 µl of 80 µg/ml protein in HEPES buffer (100 mM HEPES, 150 mM NaCl, pH 7.5) followed by centrifugation at 800 RPM for 1 minute, and then incubated for 3 hours at room temperature or overnight at 4° C. Plates were then washed three times with assay buffer (HEPES buffer with 0.5% DMSO) and then followed with a final volume of 15 µl assay buffer. The binding assay was performed in 4 or 6-point dose-response format. Testing compounds were diluted with assay buffer in 384-well compound plates. Because compound stocks are in DMSO that affects the Epic label-free readout, the compound plates were prepared by Echo550 acoustic dispenser to keep DMSO content balanced for all wells. Compounds were then transferred to assay plates by a multichannel robotic liquid handler. An alternative approach was to add compounds in dose-curve format directly to assay plates using the nanoliter dispenser Echo550.

The binding of compounds to WWP2 (SEQ ID NO:24) was measured on the EnSpire label-free plate reader. After 25 minutes of thermal equilibration, a baseline reading was taken on the label-free plates with protein immobilized in assay buffer. In the next step, 25 µl of reconstituted compounds were added to the plates and mixed. The final reading was taken after 25 min of thermal equilibration and over a period of 60 minutes. The label-free responses were measured as shifts in reflected wavelength and were expressed in picometers (pm). Results were analyzed using the EnSpire label-free user interface software. The difference between the last baseline measurements and the signal max was used to determine the binding of compounds to WWP2.

Example 4

Expression of Soluble TSG101 Fragment Containing PTAP-motif Binding Domain

The full-length nucleotide and amino acid sequence of TSG101 is presented in Table VIII. The full-length TSG101 polypeptide (SEQ ID NO:32) is not sufficiently soluble for performing the in vitro screening assays disclosed herein. Accordingly, a truncated TSG101 peptide that contains amino acids corresponding to positions 2-145 of the full-length TSG101 peptide and includes a PTAP-binding domain was prepared having sufficient solubility for these in vitro screening assays. The resultant TSG101 peptide (SEQ ID NO:33) used for these studies is illustrated in Table VIII.

TABLE VIII

Nucleotide and amino acid sequences of full-length TSG101 peptide and expression construct for UEV domain of truncated-length TSG101 recombinant peptide

| SEQ ID NO: | Sequence[1] |
| --- | --- |
| 31 | gaagcggaag tggtgtagtg gtgccgactt cctgttgttt gaggccgggt tgggggtgtg cgattgtgtg ggacggtctg gggcagccca gcagcggctg accctctgcc tgcggggaag ggagtcgcca ggcggccgtc ATGgcggtgt cggagagcca gctcaagaaa atggtgtcca agtacaaata cagagaccta actgtacgtg aaactgtcaa tgttattact ctatacaaag atctcaaacc tgttttggat tcatatgttt ttaacgatgg cagttccagg gaactaatga acctcactgg aacaatccct gtgccttata gaggtaatac atacaatatt ccaatatgcc tatggctact ggacacatac ccatataatc cccctatctg ttttgttaag cctactagtt caatgactat taaaacagga aagcatgttg atgcaaatgg gaagatatat cttccttatc tacatgaatg gaaacaccca cagtcagact tgttgggggct tattcaggtc atgattgtgg tatttggaga tgaacctcca gtcttctctc gtcctatttc ggcatcctat ccgccatacc |

TABLE VIII-continued

Nucleotide and amino acid sequences of full-length TSG101 peptide and expression construct for UEV domain of truncated-length TSG101 recombinant peptide

| SEQ ID NO: | Sequence[1] |
|---|---|
| | aggcaacggg gccaccaaat acttcctaca tgccaggcat gccaggtgga atctctccat acccatccgg ataccctccc aatcccagtg gttacccagg ctgtccttac ccacctggtg gtccatatcc tgccacaaca agttctcagt acccttctca gcctcctgtg accactgttg gtcccagtag ggatggcaca atcagcgagg acaccatccg agcctctctc atctctgcgg tcagtgacaa actgagatgg cggatgaagg aggaaatgga tcgtgcccag gcagagctca atgccttgaa acgaacagaa gaagacctga aaaagggtca ccagaaactg gaagagatgg ttacccgttt agatcaagaa gtagccgagg ttgataaaaa catagaactt ttgaaaaaga aggatgaaga actcagttct gctctggaaa aaatggaaaa tcagtctgaa aacaatgata tcgatgaagt tatcattccc acagctccct tatacaaaca gatcctgaat ctgtatgcag aagaaaacgc tattgaagac actatctttt acttgggaga agccttgaga aggggcgtga tagacctgga tgtcttcctg aagcatgtac gtcttctgtc ccgtaaacag ttccagctga gggcactaat gcaaaaagca agaaagactg ccggtctcag tgacctctac TGActtctct gataccagct ggaggttgag ctcttcttaa agtattcttc tcttccttt atcagtaggt gcccagaata agttattgca gtttatcatt caagtgtaaa atattttgaa tcaataatat attttctgtt ttctttggt aaagactggc ttttattaat gcactttcta tcctctgtaa actttttgtg ctgaatgttg ggactgctaa ataaaatttg ttgcataaaa aaaaaaaaaa aa |
| 32 | MAVSESQLKKMVSKYKYRDLTVRETVNVITLYKDLKPVLDSYVFNDGSSRELMNLTGTIP VPYRGNTYNIPICLWLLDTYPYNPPICFVKPTSSMTIKTGKHVDANGKIYLPYLHEWKHP QSDLLGLIQVMIVVFGDEPPVFSRPISASYPPYQATGPPNTSYMPGMPGGISPYPSGYPP NPSGYPGCPYPPGGPYPATTSSQYPSQPPVTTVGPSRDGTISEDTIRASLISAVSDKLRW RMKEEMDRAQAELNALKRTEEDLKKGHQKLEEMVTRLDQEVAEVDKNIELLKKKDEELSS ALEKMENQSENNDIDEVIIPTAPLYKQILNLYAEENAIEDTIFYLGEALRRGVIDLDVFL KHVRLLSRKQFQLRALMQKARKTAGLSDLY |
| 33 | *MGSSHHHHHHSSGLVPRGSHMAS*<u>ENLYFQG</u>AVSESQLKKMVSKYKYRDLTVRETVNVITLYKDLKPVL DSYVFNDGSSRELMNLTGTIPVPYRGNTYNIPICLWLLDTYPYNPPICFVKPTSSMTIKTGKHVDANG KIYLPYLHEWKHPQSDLLGLIQVMIVVFGDEPPVFSRP |

[1]The initiator and terminator codons in the full-length TSG101 nucleotide sequence are bolded. The UEV domain of TSG101 peptide sequence for amino acids 2-145 are presented in bolded fonts in the full-length TSG101 peptide and the truncated-length TSG101 recombinant peptide. With respect to the truncated-length TSG101 recombinant peptide, the italicized font is leader peptide sequence that includes a polyhistidine motif and thrombin cleavage site derived from the expression vector, pET28b (Novagen). The underlined sequence is a TEV cleavage site introduced at the amino terminus of the TGS101 peptide sequence.

The complete sequence of the pET28b expression vector that includes the truncated TSG101 is presented below.

SEQ ID NO: 34:
TGGCGAATGGGACGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCTTCCTTTCTCG
CCACGTTCGCCGGCTTTCCCCGTCAAGCTCTAAATCGGGGGCTCCCTTTAGGGTTCCGATTTAG
TGCTTTACGGCACCTCGACCCCAAAAAACTTGATTAGGGTGATGGTTCACGTAGTGGGCCATCG
CCCTGATAGACGGTTTTTCGCCCTTTGACGTTGGAGTCCACGTTCTTTAATAGTGGACTCTTGT
TCCAAACTGGAACAACACTCAACCCTATCTCGGTCTATTCTTTTGATTTATAAGGGATTTTGCC
GATTTCGGCCTATTGGTTAAAAAATGAGCTGATTTAACAAAAATTTAACGCGAATTTTAACAAA
ATATTAACGTTTACAATTTCAGGTGGCACTTTTCGGGGAAATGTGCGCGGAACCCCTATTTGTT
TATTTTTCTAAATACATTCAAATATGTATCCGCTCATGAATTAATTCTTAGAAAAACTCATCGA
GCATCAAATGAAACTGCAATTTATTCATATCAGGATTATCAATACCATATTTTTGAAAAAGCCG
TTTCTGTAATGAAGGAGAAAACTCACCGAGGCAGTTCCATAGGATGGCAAGATCCTGGTATCGG
TCTGCGATTCCGACTCGTCCAACATCAATACAACCTATTAATTTCCCCTCGTCAAAAATAAGGT
TATCAAGTGAGAAATCACCATGAGTGACGACTGAATCCGGTGAGAATGGCAAAAGTTTATGCAT
TTCTTTCCAGACTTGTTCAACAGGCCAGCCATTACGCTCGTCATCAAAATCACTCGCATCAACC
AAACCGTTATTCATTCGTGATTGCGCCTGAGCGAGACGAAATACGCGATCGCTGTTAAAAGGAC
AATTACAAACAGGAATCGAATGCAACCGGCGCAGGAACACTGCCAGCGCATCAACAATATTTTC
ACCTGAATCAGGATATTCTTCTAATACCTGGAATGCTGTTTTCCCGGGGATCGCAGTGGTGAGT
AACCATGCATCATCAGGAGTACGGATAAAATGCTTGATGGTCGGAAGAGGCATAAATTCCGTCA
GCCAGTTTAGTCTGACCATCTCATCTGTAACATCATTGGCAACGCTACCTTTGCCATGTTTCAG
AAACAACTCTGGCGCATCGGGCTTCCCATACAATCGATAGATTGTCGCACCTGATTGCCCGACA
TTATCGCGAGCCCATTTATACCCATATAAATCAGCATCCATGTTGGAATTTAATCGCGGCCTAG
AGCAAGACGTTTCCCGTTGAATATGGCTCATAACACCCCTTGTATTACTGTTTATGTAAGCAGA
CAGTTTTATTGTTCATGACCAAAATCCCTTAACGTGAGTTTTCGTTCCACTGAGCGTCAGACCC
CGTAGAAAAGATCAAAGGATCTTCTTGAGATCCTTTTTTTCTGCGCGTAATCTGCTGCTTGCAA
ACAAAAAAACCACCGCTACCAGCGGTGGTTTGTTTGCCGGATCAAGAGCTACCAACTCTTTTTC
CGAAGGTAACTGGCTTCAGCAGAGCGCAGATACCAAATACTGTCCTTCTAGTGTAGCCGTAGTT
AGGCCACCACTTCAAGAACTCTGTAGCACCGCCTACATACCTCGCTCTGCTAATCCTGTTACCA
GTGGCTGCTGCCAGTGGCGATAAGTCGTGTCTTACCGGGTTGGACTCAAGACGATAGTTACCGG
ATAAGGCGCAGCGGTCGGGCTGAACGGGGGGTTCGTGCACACAGCCCAGCTTGGAGCGAACGAC
CTACACCGAACTGAGATACCTACAGCGTGAGCTATGAGAAAGCGCCACGCTTCCCGAAGGGAGA
AAGGCGGACAGGTATCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGACTTGAGCGTCGATT
TTTGTGATGCTCGTCAGGGGGCGGAGCCTATGGAAAAACGCCAGCAACGCGGCCTTTTTACGG
TTCCTGGCCTTTTGCTGGCCTTTTGCTCACATGTTCTTTCCTGCGTTATCCCCTGATTCTGTGG
ATAACCGTATTACCGCCTTTGAGTGAGCTGATACCGCTCGCCGCAGCCGAACGACCGAGCGCAG
CGAGTCAGTGAGCGAGGAAGCGGAAGAGCGCCTGATGCGGTATTTTCTCCTTACGCATCTGTGC
GGTATTTCACACCGCATATATGGTGCACTCTCAGTACAATCTGCTCTGATGCCGCATAGTTAAG
CCAGTATACACTCCGCTATCGCTACGTGACTGGGTCATGGCTGCGCCCCGACACCCGCCAACAC
CCGCTGACGCGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAGGCAGCTGCGG

-continued

```
TAAAGCTCATCAGCGTGGTCGTGAAGCGATTCACAGATGTCTGCCTGTTCATCCGCGTCCAGCT
CGTTGAGTTTCTCCAGAAGCGTTAATGTCTGGCTTCTGATAAAGCGGGCCATGTTAAGGGCGGT
TTTTTCCTGTTTGGTCACTGATGCCTCCGTGTAAGGGGGATTTCTGTTCATGGGGGTAATGATA
CCGATGAAACGAGAGAGGATGCTCACGATACGGGTTACTGATGATGAACATGCCCGGTTACTGG
AACGTTGTGAGGGTAAACAACTGGCGGTATGGATGCGGCGGGACCAGAGAAAAATCACTCAGGG
TCAATGCCAGCGCTTCGTTAATACAGATGTAGGTGTTCCACAGGGTAGCCAGCAGCATCCTGCG
ATGCAGATCCGGAACATAATGGTGCAGGGCGCTGACTTCCGCGTTTCCAGACTTTACGAAACAC
GGAAACCGAAGACCATTCATGTTGTTGCTCAGGTCGCAGACGTTTTGCAGCAGCAGTCGCTTCA
CGTTCGCTCGCGTATCGGTGATTCATTCTGCTAACCAGTAAGGCAACCCCGCCAGCCTAGCCGG
GTCCTCAACGACAGGAGCACGATCATGCGCACCCGTGGGGCCGCCATGCCGGCGATAATGGCCT
GCTTCTCGCCGAAACGTTTGGTGGCGGGACCAGTGACGAAGGCTTGAGCGAGGGCGTGCAAGAT
TCCGAATACCGCAAGCGACAGGCCGATCATCGTCGCGCTCCAGCGAAAGCGGTCCTCGCCGAAA
ATGACCCAGAGCGCTGCCGGCACCTGTCCTACGAGTTGCATGATAAAGAAGACAGTCATAAGTG
CGGCGACGATAGTCATGCCCCGCGCCCACCGGAAGGAGCTGACTGGGTTGAAGGCTCTCAAGGG
CATCGGTCGAGATCCCGGTGCCTAATGAGTGAGCTAACTTACATTAATTGCGTTGCGCTCACTG
CCCGCTTTCCAGTCGGGAAACCTGTCGTGCCAGCTGCATTAATGAATCGGCCAACGCGCGGGGA
GAGGCGGTTTGCGTATTGGGCGCCAGGGTGGTTTTTCTTTTCACCAGTGAGACGGGCAACAGCT
GATTGCCCTTCACCGCCTGGCCCTGAGAGAGTTGCAGCAAGCGGTCCACGCTGGTTTGCCCCAG
CAGGCGAAAATCCTGTTTGATGGTGGTTAACGGCGGGATATAACATGAGCTGTCTTCGGTATCG
TCGTATCCCACTACCGAGATATCCGCACCAACGCGCAGCCCGGACTCGGTAATGGCGCGCATTG
CGCCCAGCGCCATCTGATCGTTGGCAACCAGCATCGCAGTGGGAACGATGCCCTCATTCAGCAT
TTGCATGGTTTGTTGAAAACCGGACATGGCACTCCAGTCGCCTTCCCGTTCCGCTATCGGCTGA
ATTTGATTGCGAGTGAGATATTTATGCCAGCCAGCCAGACGCAGACGCGCCGAGACAGAACTTA
ATGGGCCCGCTAACAGCGCGATTTGCTGGTGACCCAATGCGACCAGATGCTCCACGCCCAGTCG
CGTACCGTCTTCATGGGAGAAAATAATACTGTTGATGGGTGTCTGGTCAGAGACATCAAGAAAT
AACGCCGGAACATTAGTGCAGGCAGCTTCCACAGCAATGGCATCCTGGTCATCCAGCGGATAGT
TAATGATCAGCCCACTGACGCGTTGCGCGAGAAGATTGTGCACCGCCGCTTTACAGGCTTCGAC
GCCGCTTCGTTCTACCATCGACACCACCACGCTGGCACCCAGTTGATCGGCGCGAGATTTAATC
GCCGCGACAATTTGCGACGGCGCGTGCAGGGCCAGACTGGAGGTGGCAACGCCAATCAGCAACG
ACTGTTTGCCCGCCAGTTGTTGTGCCACGCGGTTGGGAATGTAATTCAGCTCCGCCATCGCCGC
TTCCACTTTTTCCCGCGTTTTCGCAGAAACGTGGCTGGCCTGGTTCACCACGCGGGAAACGGTC
TGATAAGAGACACCGGCATACTCTGCGACATCGTATAACGTTACTGGTTTCACATTCACCACCC
TGAATTGACTCTCTTCCGGGCGCTATCATGCCATACCGCGAAAGGTTTTGCGCCATTCGATGGT
GTCCGGGATCTCGACGCTCTCCCTTATGCGACTCCTGCATTAGGAAGCAGCCCAGTAGTAGGTT
GAGGCCGTTGAGCACCGCCGCCGCAAGGAATGGTGCATGCAAGGAGATGGCGCCCAACAGTCCC
CCGGCCACGGGGCCTGCCACCATACCCACGCCGAAACAAGCGCTCATGAGCCCGAAGTGGCGAG
CCCGATCTTCCCCATCGGTGATGTCGGCGATATAGGCGCCAGCAACCGCACCTGTGGCGCCGGT
GATGCCGGCCACGATGCGTCCGGCGTAGAGGATCGAGATCTCGATCCCGCGAAATTAATACGAC
TCACTATAGGGAATTGTGAGCGGATAACAATTCCCCTCTAGAAATAATTTTGTTTAACTTTAA
GAAGGAGATATACCATG*GGCAGCAGCCATCATCATCATCATCACAGCAGCGGCCTGGTGCCGCG
CGGCAGCC*ATATGGCTAGCgaaaacctgtacttccagggcgcggtgtcggagagccagctcaag
```

-continued

```
aaaatggtgtccaagtacaaatacagagacctaactgtacgtgaaactgtcaatgttattactc tatacaaagatctcaaacctgttttggattcatatgttttaacgatggcagttccagggaact aatgaacctcactggaacaatccctgtgccttatagaggtaatacatacaatattccaatatgc ctatggctactggacacatacccatataatccccctatctgttttgttaagcctactagttcaa tgactattaaaacaggaaagcatgttgatgcaaatgggaagatatatcttccttatctacatga atggaaacacccacagtcagacttgttggggcttattcaggtcatgattgtggtatttggagat gaacctccagtcttctctcgtccttgataaGGATCCGAATTCGAGCTCCGTCGACAAGCTTGCG

GCCGCACTCGAGCACCACCACCACCACCACTGAGATCCGGCTGCTAACAAAGCCCGAAAGGAAG

CTGAGTTGGCTGCTGCCACCGCTGAGCAATAACTAGCATAACCCCTTGGGGCCTCTAAACGGGT

CTTGAGGGGTTTTTGCTGAAAGGAGGAACTATATCCGGAT
``` wherein the bold font denote the locations of the initiator and terminator codons for the recombinant peptide pro-form; the upper case letters denote pET28b vector sequences; the lower case letter denote the truncated TSG101 (2-145) coding sequences, the italicized font includes the leader peptide coding sequence that includes a polyhistidine motif and thrombin cleavage site derived from the expression vector, pET28b (Novagen). The underlined sequence is a TEV cleavage site introduced at the amino terminus of the TGS101 peptide sequence.

Example 5

High Throughput Fluorescence-based Thermal Shift (FTS) Assay for TSG101

The NU-HTA has developed a robotic pipeline for small molecule protein ligand screening by FTS. See Luan C H, Light S H, Dunne S F, Anderson W F. Ligand screening using Fluorescence Thermal Shift Analysis (FTS). In Structural Genomics and Drug Discovery: Methods and Protocols. *Methods Mol. Biol.* 2013, Humana Press (In press), which is incorporated by reference in its entirety. The pipeline uses an Echo550 acoustic transfer robot (Labcyte, CA) for compound addition and the Mosquito robot (TTP LabTechnologies, UK) for protein dispensing followed by thermal scanning coupled with fluorescence detection which is performed on a real-time PCR machine CFX384 (Bio-Rad Laboratories). The method does not require any labeling on either protein or compound. A fluorescent dye Sypro-Orange (Invitrogen) is used for assay detection. TSG101 (SEQ ID NO:33) has a thermal unfolding profile ideal for using FTS as primary screen assay.
Compound Library Screening.

For primary screening, the TSG101 protein (SEQ ID NO:33) was premixed at a concentration of 2 uM with a 5× concentration of Sypro-Orange in Hepes buffer (100 mM HEPES, 150 mM NaCl, pH 7.5). Then 10 uL of the protein-dye mix was added to an assay plate. And 10 to 50 nanoliters of compound, equal to 10 to 50 uM, were added. The plate was shaken to ensure proper mixing and then sealed with optical seal and centrifuged. The thermal scan was performed from 10 to 95° C. with a temperature ramp rate of 1.5° C./min. The fluorescence was recorded every 10 sec. Data analysis and report generation were performed by using the in-house software excelFTS. Hit compounds identified were tested in dose-response format.

Validation of the Confirmed Hits with TSG101 by FP and EpicLF.

The confirmed hits from the primary FTS screening were validated by fluorescent polarization (FP) and Epic label-free (EpicLF) assays. The EpicLF assay was performed on an EnSpire multifunction plate reader (Perkin Elmer) to determine the Kd of hit compound binding to TSG101 (SEQ ID NO:33) as described generally in Example 3 for candidate compound binding to Nedd 4 peptide family members. The hit compounds were also tested by FP assay to determine the IC50 of disrupting TSG101 (SEQ ID NO: 33) and PTAP-probe interaction as described generally in Example 2 for candidate compound screening to determine IC50 of disrupting Nedd 4 peptide family members and PY-probe interaction.

For this purpose, tandem-linked versions of the PTAP motif from HIV-1 gag was designed and synthesized for use in these experiments. The structures of the resulting peptides are presented below.

```
SEQ ID NO: 20:
RPGNFLQSRPEPTAPPFLQSRPEPTAPPEESFRRRR

SEQ ID NO: 21:
FITC-RPGNFLQSRPEPTAPPFLQSRPEPTAPPEESFRRRR

SEQ ID NO: 22:
TAMRA-RPGNFLQSRPEPTAPPFLQSRPEPTAPPEESFRRRR
```

Example 6

In Vivo Screening for Compounds that Disrupt the Interaction of TSG101 and the PTAP L-domain Sequence in the p6 Region of HIV-1 Gag
(Prophetic Example)

Cells will be transfected with suitable vector constructs to express (either transiently or stably) EGFP reconstituted from a two-hybrid system comprising a fusion protein containing PTAPP motifs and the N-terminal portion of EGFP and a fusion protein containing TSG101 polypeptides and the C-terminal portion of EGFP. Following establishment of stable EGFP expression, the ability of test compound to enter the cells and inhibit EGFP expression will be evaluated. A reduction of EGFP fluorescence as a function of test compound administration to cells will indicate that the compound inhibits formation of functional GFP complexes from the two component system. Controls will be performed that include evaluation the cytotoxicity of the test compounds having positive effect in this assay.

Plasmids for CEGFP-N1. The plasmid pCEGFP-N1, which places CEGFP under control of the T7 promoter, was created by PCR amplification (Deep Vent polymerase) of the gene for C-terminal EGFP (from 159 to 265 amino acids) from pEGFP-N1 using the oligonucleotides 5'-ataggatccac-cgg tcgccaccggtggctctggc aagaacgg catcaaggtg aacttcaa-3' forward primer (SEQ ID NO:35) and 5'-gtcgcggccgctttact-tgtacagctcgtccatg-3' reverse primer (SEQ ID NO:36). The 4-residue linker (GGSG (SEQ ID NO:37)) is located at the beginning of the CEGFP gene. This was followed by digestion of PCR products and the plasmid pEGFP-N1 with NheI and XhoI, and then ligation with T4 DNA ligase. The C-terminal EGFP ligation was confirmed by DNA sequencing by using sequencing primer (5'-gcagagctggtttagtg-3' forward (SEQ ID NO:38), from 561 to 577 bp of pEGFP-N1 sequences).

Plasmids for NEGFP-C3. The plasmid pNEGFP-N1, which places NEGFP under control of the T7 promoter, was created by PCR amplification (Deep Vent polymerase) of the gene for N-terminal EGFP (from 1 to 158 amino acids) from pEGFP-C3 using the oligonucleotides 5'-cagatcc gctagcgc-taccggtcgcca ccatggtgag forward primer (SEQ ID NO:39) and 5'-atactcgagatctgagtacccagagccagagccaccctgatgtcggc-catgatatag-3' reverse primer (SEQ ID NO:40). The 6-residue peptide linker (GGSGSG [(SEQ ID NO:41)]) is located at the end of the NEGFP gene. This was followed by digestion of PCR products and the plasmid pEGFP-C3 with BamHI and NotI, and then ligation with T4 DNA ligase. The N-terminal EGFP ligation was confirmed by DNA sequencing by using sequencing primer 5'gtgggaggttttttaaa-3' reverse (from 1451 to 1467 bp of pEGFP-C3 sequences) (SEQ ID NO:42).

Construct NEGFP-2×PTAPP. Two copies of PTAPP sequences of HIV Gag were amplified from pGBT9_HIV Gag with 2PTAP template (from Dr. Carol Carter's lab) by PCR reaction by using the oligonucleotides. This was followed by digestion of PCR products and the plasmid pNEGFP-C3 with EcoRI and BamHI, and then ligation with T4 DNA ligase.

Construct CEGFP-TSG101. TSG101 was amplified by PCR reaction by using the oligonucleotides. This was followed by digestion of PCR products and the plasmid pNEGFP-C3 with EcoRI and BamHI, and then ligation with T4 DNA ligase.

Example 7

Biological Testing of Compounds to Inhibit Virus Budding Detected by Release of VLPs from Cells Transfection of 293/E Cells and chemical inhibitor treatment. 293/E cells were cultured in DMEM supplemented with 10% fetal bovine serum, penicillin (1,000 units/ml), and streptomycin (1,000 µg/ml) to 50% confluence at 37° C. Expression of plasmids from p2036 was high in 293/E cells because these cells stably express the EBNA1 protein of EBV and the p2036 constructs contain the EBV FR plasmid maintenance element that EBNA1 binds. Therefore 293/E cells were used when proteins expressed from p2036 were to be detected by western analysis. In all experiments, 24-well plates of 293/E cells were transfected with 0.5 µg of p2036-ASLV Gag with the X-treme Gene9 transfection reagent (Roche Diagnostics, Alameda, Calif., USA) according to the manufacturer's instructions. After 24 h after DNA transfection, the cells were washed with 1×DPS that contained $CaCl_2$ (0.1 mM) and $MgCl_2$ (1 mM) [Gibco #14040-133], and 1 ml of cell culture medium (10% FBS, 1% Penicillin/Streptomycin) containing $CaCl_2$ (0.5 mM) and $MgCl_2$ (5 mM) was added. Thereafter, the inhibitor compounds were added to the culture medium of parallel culture wells at one of the following final concentrations: 5 µM, 10 µM, 20 µM, or 40 µM and the cells remained in contact with the culture medium containing the inhibitor compounds for 5 hr. Cells and virus-like particles (VLPs) released into the cell media were collected 5 h after chemical treatment.

Detection of Gag proteins by western blotting. For the budding assay, both media and cell lysate fractions were collected. The cell lysate fractions were prepared by suspension in radioimmune precipitation assay (RIPA) buffer [PBS containing 1% Nonidet P-40, 0.5% sodium deoxycholate, 0.1% SDS, and protease inhibitor mixture tablets] 48 hours post-transfection. VLPs were purified from the cell culture medium by centrifugation through a 20% sucrose cushion at 100,000×g for 1 h at 4° C. (Beckman SW50.1 rotor). The pelleted VLPs were suspended in 100 µl of RIPA buffer containing protease inhibitor mixture tablets. For lysate fractions, Gag proteins were immunoprecipitated overnight at 4° C. with an anti-ASLV monoclonal serum (1:500-1:1000 dilution) and 20 µl of protein A-agarose beads. The precipitated proteins were separated by SDS-PAGE and transferred to a polyvinylidene difluoride membrane. After blocking of the membrane with wash buffer (10 mM Tris-HCl, pH 8.0, 150 mM NaCl, and 0.1% Tween 20) containing 5% nonfat dry milk, ASLV Gag proteins were detected with an AMV MA (p19) directed monoclonal antibody (mAb) and an anti-mouse IgG-HRP secondary antibody for ECL (Denville Scientific; Metuchen, N.J.).

Viral Replication Assays.

293/E cells in 6-well plates were transfected with HIV-1 luciferase reporter vector consisting of the following plasmids: 1.5 µg of pHIV env-Luc and 0.75 µg of VSV-G (Provided by Tom Hope, Northwestern University). Supernatants containing pseudo-typed virions were harvested 24 or 48 h after the chemical treatments, and the cells were harvested at the same time for western blot analyses. To measure titers, virus particles were filtered through a 0.45 µm filter, and infectivity was assayed by incubating in duplicate $1\times10^5$ 293/E cells/well with 1 ml of pseudo typed virus in 6-well plates for 5 h. Virus was then removed and cell growth media was added. The cells were lysed in 400 µl of cell culture lysis reagent (Promega, Madison, Wis.) at 72 h post-transfection. The luciferase activity was measured with a luciferase assay kit (Promega, Madison, Wis.) and a FB12 luminometer according to manufacturer's instructions. The data are presented as the average of the duplicates.

Example 8

Biological Testing of Nedd4 Inhibitor Candidate Compounds K21 (Benserazide Hydrochloride) and N20 (Oxytetracycline) by Cell Culture Assays In Vitro Cell-based Inhibition Assay COS-1 cells were seeded on twelve-well plates and grown in 1 ml of DMEM with 10% fbs and 1% Penicillin/Streptomycin. The following day, well were confluency was ~60% were selected for co-transfection with an NL4-3 derived construct (pdeltaEnv) and pIIIEnv for expression of HIV-1 virus-encoded proteins. Inhibitor treatment was done on two sets of transfected cells: one, at 5 hr post-transfection and the other, at 24 hours post-transfection. In each case, the tissue culture media was removed and replaced with treatment Nedd4 inhibitor (100 µM final concentration for K21 and 20 µM final concentration for N20) or DMSO control (1% final concentration) in DMEM with 10% FBS, 1% Penicillin/Streptomycin, 5 mM $MgCl_2$, and 0.5 mM $CaCl_2$. After a 24-hr treatment period, the tissue culture media was collected, cleared of debris by running through a 0.45 um syringe filter and analyzed for amount of virus particles by Elisa p24 capture assay.

Cell Death Evaluation.

The standard trypan blue assay, where dead cells are blue when visualized under a light microscope, was used to determine the percent of dead cells in the culture. Briefly, cells from a well of DMSO-treated, K21-treated and N20-treated samples were dislodged from the well with a stream of 1 ml PBS, collected, pelleted at 200 rpm for 2 min, and suspended in 300 µl trypsin-EDTA, incubated at 37° C. for 30 min. A diluted cell suspension was prepared by mixing 200 µl of the trypsin-treated cell suspension and 800 µl of PBS was used for the assay. For the assay itself: from the 1 ml of diluted cell suspension, 50 µl was taken an placed on paraffin and to this was mixed in 50 µl of 0.4% Trypan Blue dye in PBS, after exactly 2 minutes later, the mixture was loaded on a hematocytometer. The hematocytometer was placed on the light microscope stage and a blue cell count and an all cells count (blue and not blue cells) obtained. Two 50 µl aliquots were counted per sample. The results are presented in Table VII.

TABLE VII

Cytotoxicity results for contacting cells with inhibitor compounds.

| Compound | Blue cells | Total cells | Cytotoxicity[1] |
|---|---|---|---|
| DMSO | 7 | 29 | 24% |
|  | 9 | 49 | 18% |
|  |  |  | (21%) |
| K21 | 13 | 38 | 34% |
|  | 17 | 60 | 28% |
|  |  |  | (31%) |
| N20 | 11 | 37 | 29% |
|  | 7 | 20 | 35% |
|  |  |  | (32%) |

[1]Cytotoxicity (%) is determined by the fraction (blue cells)/(total cells) multiplied by 100 (%). The average of the independent experiments is shown in parentheses.

Cell Growth Based on Cell Lysate Actin Levels

The levels of actin of cell lysates prepared from DMSO-treated, K21-treated and N20-treated cells were determined by SDS-PAGE followed by Western analysis where the immunoblot were probed with mouse anti-actin antibody. The intensity of the actin bands were essentially comparable for all samples (not shown).

Effects on HIV-1 Production

Accumulation of Gag-related Proteins in the Cell

The levels of Gag-related proteins in cell lysates were immune-precipitated with polyclonal anti CA antibody. Proteins in the immune-precipitate were separated by SDS-PAGE and followed by Western analysis where the blot was probed with mouse anti-CA antibody. The commercial antibody used (NEN NEA-9306) is known to recognize the Gag precursor better than the mature p24 proteins (Dietrich et al 2001). Both GagPr55 and mature p24, as adjudged by their respective band intensities, were essentially comparable for all samples (not shown).

Elisa p24 Capture Assay of Tissue Culture Media

At 100 µM, K21 was inhibitory to virus particle release. There was a reduction in the amount of virus particle detected in the tissue culture media. This was true whether the inhibitor was added at 5 hrs post-transfection or at 24 hrs post transfection. At 20 µM, N20 was also exerted an inhibitory effect on virus particle release but it was different from that of K21. There was a reduction in the amount of virus particle detected in the tissue culture media when inhibitor was added at 5 hr post-transfection. This reduction was not seen when inhibitor was added 24 hrs post-transfection.

Specific Infectivity

The amount of infectious virus normalized to ng of p24 obtained from the ELISA assay in the tissue cultures was determined by multinuclear activation of a galactosidase indicator (MAGI) assay. In this assay, infectious unit is scored by the blue color that is assumed by infected MAGI cells (Hela cells that have been engineered to express the indicator when the infecting particle is able to simulated natural infection up until expression of HIV-1 Tat). Counts of Blue cells per ng p24 for the DMSO controls, K21-treated and N20-treated samples were comparable.

Example 9

HSV-1 Inhibition Assay by PTAP-Inhibitor Compounds F15 (Esomeprazole Potassium) and N16 (Tenatoprazole)

MTS Assay

The cytotoxicity of the compounds was determined by a commercially available assay (Celltiter 96® $AQ_{ueous}$ One Solution cell proliferation assay reagent; Promega, Madison, Wis.), as described previously (Akkarawongsa et al., 2006). The CellTiter 96® $AQ_{ueous}$ One Solution Cell Proliferation Assay is a colorimetric method for determining the number of viable cells in proliferation, cytotoxicity or chemosensitivity assays. The CellTiter 96® $AQ_{ueous}$ One Solution Reagent contains a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES). PES has enhanced chemical stability, which allows it to be combined with MTS to form a stable solution. The CellTiter 96® $AQ_{ueous}$ Assay uses phenazine methosulfate (PMS) as the electron coupling reagent, and PMS Solution and MTS Solution are supplied separately. PES has enhanced chemical stability, which allows it to be combined with MTS to form a stable solution. Assays are performed by adding a small amount of the CellTiter 96® $AQ_{ueous}$ One Solution Reagent directly to culture wells, incubating for 1-4 hours and then recording absorbance at 490 nm with a 96-well plate reader. The quantity of formazan product as measured by the amount of 490 nm absorbance is directly proportional to the number of living cells in culture.

Briefly, Vero cells ($1.5 \times 10^4$ cells/well) were seeded in a 96-well plate, and the plate was incubated for 24 h at 37° C. A total of 20 µl of medium containing the desired concentration of inhibitors was added to the cells. Control cells received medium only. After incubation of the cells in the presence of peptide overnight at 37° C., 20 µl of the 96 AQqueous One Solution cell proliferation assay reagent was added to each well. The plate was then incubated for 2 h at 37° C., and the absorbance at 490 nm was determined with a 96-well plate reader (Perkin Elmer).

Assay for Inhibitor Compound Effects on Infected Cells and HSV-1 Virus Production and Release.

Vero cells were grown in DMEM supplemented with 10% FBS. Viral infections were performed in DMEM supplemented with 1% heat-inactivated FBS. Vero cells were inoculated HSV-1 (strain F) at indicated concentrations, after 2 h, the cells were washed and treated with 0.1 M sodium citrate buffer (pH 3.0) for 1 min to inactivate unpenetrated viruses, washed again and incubated with fresh medium containing 1% heat-inactivated FBS. At different times after inoculation, one-half of the medium was harvested as a supernatant sample and the cells were scraped into the rest of the half medium containing released viruses as a total virus sample and lysed by sonication. Then virus titers were determined by standard plaque assay on Vero cells.

As shown in FIG. 8, inhibitor compound F15 (Esomepazole) resulted in infectious HSV-1 virion release from HSV-1 infected cells at about 10% of the level observed for virus release from infected cells not contacted with an inhibitor compound at the higher concentration tested (that is, more than a 90% reduction in virus release when F15 is present at 80 µM in the culture medium). Inhibitor compound F15 also reduced the total load of infectious virions produced in the cells, whether released or not from the cells, to about 25% of the level observed for virus release from infected cells not contacted with an inhibitor compound at the higher concentration tested (that is, more than a 75% reduction in total infectious virus when F15 is present at 80 µM in the culture medium). As shown in FIG. 8A, inhibitor compound N16 (Tenatoprazole) reduced infectious HSV-1 virion release from HSV-1 infected cells at about 5% of the level observed for virus release from infected cells not contacted with an inhibitor compound at the higher concentration tested (that is, more than a 95% reduction in virus release when N16 is present at 80 µM in the culture medium). Thus, inhibitor compound N16 was slightly more effective than F15 at reducing infectious HSV-1 virion particle release from HSV-1 infected cells at the concentrations tested. Neither inhibitor compound was cytotoxic to the Vero cells at the concentrations tested (FIG. 8B).

Example 10

Testing of Compounds to Inhibit the Budding of KSHV (Prophetic Example)

KSHV, a member of the herpes virus family, buds from cells with a Vps4 dependence, probably using the PY motif-dependent pathway. To test the effect of inhibitors on KSHV release, of a recently reported cell line (iSLK.219) will be used that allows the doxycycline (Dox) inducible expression of the KSHV lytic transactivator protein (RTA) and is infected with recombinant KSHV.219. See Myoung J, Ganem D. Generation of a doxycycline-inducible KSHV producer cell line of endothelial origin: maintenance of tight latency with efficient reactivation upon induction. J Virol Methods. 2011, 174(1-2):12-21. PMCID: 3095772 and Vieira J, O'Hearn P M. Use of the red fluorescent protein as a marker of Kaposi's sarcoma-associated herpesvirus lytic gene expression. Virology. 2004; 325(2):225-40. The contents of these printed publication are incorporated by reference in their entirety. Upon Dox treatment of these cells, lytic reactivation results in the production of infectious KSHV carrying a GFP reporter cassette. The ability of individual dominant negative ESCRT proteins interfere with the release of infectious KSHV will be evaluated initially. For this purpose, $10^5$ iSLK.219 cells will be plated per well in 6 well plates and transfected the next day with increasing amounts of control vectors or vectors expressing dominant negative ESCRT proteins (range 0.2 µg-2 mg/well) using Lipofectamine 2000 (Invitrogen) as instructed. Four hours after transfection, growth medium will be exchanged for medium containing 1 mg/ml Dox and cells will be incubated for 48 hours. Resulting virus containing supernatant will be cleared by centrifugation (5 min, 2000 rpm), filtered through 450 nm pore size filters and will titered on the KSHV-negative endothelial cell line SLK by serial dilutions in a 24 well format. For this, 20,000 cells will be infected with filtered virus in serial dilutions into normal growth medium (i.e. 1:1, 1:5, 1:25). Forty-eight hours after infection, SLK cells will be trypsinized, recovered by centrifugation (5 min, 1400 rpm), fixed with 4% paraformaldehyde for 20 min at room temperature, washed once with PBS, suspended in 300 ml PBS and subjected to flow cytometry on a FACS Canto II in order to establish the percentage of green cells. If ESCRT proteins are indeed required for KSHV production, a reduction in virus titer will be expected.

In a parallel positive control experiment, the effect of wild type or dominant negative ESCRT proteins on the release of a GFP-positive lentiviral vector pLCE from SLK cells will be monitored by titration and flow cytometry. The lentiviral vector pLCE is described in Zhang J, Jima D D, Jacobs C, Fischer R, Gottwein E, Huang G, et al. Patterns of microRNA expression characterize stages of human B-cell differentiation. Blood. 2009; 113(19):4586-94, the contents of which are incorporated by reference in its entirety. This experiment will be conducted as outlined above, except that ESCRT vectors will be co-transfected with 0.5 mg pLCE and 0.125 mg each of three packaging plasmids (pMDLg-pRRE, pRSV-Rev and pVSV-G). Because lentiviral release depends on the ESCRT machinery, we expect that dominant negative ESCRT vectors will result in a reduction of lentiviral titers. If a dependence of KSHV budding on the ESCRT machinery can be established in the experiments outlined above, iSLK.219 cells will be used to test the effectiveness of novel small molecule inhibitors using the experimental procedure described above.

DEFINITIONS

When introducing elements of aspects of the embodiments, the articles "a," "an," "the," and "said" are intended to mean that there are one or more of the elements. The terms "comprising," "including," and "having" are intended to be inclusive and mean that there may be additional elements other than the listed elements. The word "or" means any one member of a particular list and also includes any combination of members of that list, unless otherwise specified.

The modal verb "may" refers to the preferred use or selection of one or more options or choices among several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the model verb "may" has the same meaning and connotation as the auxiliary verb "can."

The term "about" is used herein to mean approximately, roughly, around, or in the region of. When the term "about" is used in conjunction with a numerical range, it modifies that range by extending the boundaries above and below the numerical values set forth. Preferably, the term "about" is used herein to modify a numerical value above and below the stated value by a variance of 20 percent up or down (higher or lower).

The term "associative complex" refers to two or more molecular entities (for example, two separate polypeptides; an isolated compound and an isolated polypeptide; two separate fusion proteins that interact in a two-hybrid system, two separate proteins, among others) that are present in a complex or that are capable of forming a complex.

The chemical structures described herein are named according to IUPAC nomenclature rules and include art-accepted common names and abbreviations where appropriate. The IUPAC nomenclature can be derived with chemical structure drawing software programs, such as ChemDraw® (PerkinElmer, Inc.), ChemDoodle® (iChemLabs, LLC) and Marvin (ChemAxon Ltd.). The chemical structure controls in the disclosure to the extent that an IUPAC name is misnamed or otherwise conflicts with the chemical structure disclosed herein.

The chemical structures described herein are also cataloged according to CAS Registry Nos. where appropriate. The chemical structure controls in the disclosure to the extent that an CAS Registry No. is misidentified or otherwise conflicts with the chemical structure disclosed herein.

In view of the above, it will be seen that several advantages of the invention are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the invention by way of example and not by way of limitation. This description clearly enables one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangement of components set forth in the following description or illustrated in the drawings. The invention is capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

All references, citations, patent applications, patent publications specifically mentioned in this disclosure are hereby incorporated by reference in their entireties.

---

What is claimed:

1. A method of inhibiting release of an enveloped virus from a cell, consisting of contacting the cell with a compound having an antiviral activity, said antiviral activity comprises:
   (i) inhibiting formation of an associative complex; or
   (ii) disrupting formation of an associative complex,
   wherein the associative complex comprises an L-domain motif of the enveloped virus and at least one cellular polypeptide, or fragment thereof, capable of binding the L-domain motif of the enveloped virus,
   wherein the enveloped virus is selected from the group consisting of Lassa fever virus, lymphocytic choriomeningitis virus, Ebola virus, Marberg virus, hepatitis B virus, Herpes simplex virus, type 1, Herpes simplex virus, type 2, cytomegalovirus, Simian virus, type 5, Mumps virus, avian sarcoma leucosis virus, human immunodeficiency virus, type 1, human T-lymphotrophic virus, type 1, equine infectious anemia virus, vesicular stomatitis virus, rabies virus and combinations thereof,
   wherein the compound is formula (VIII):

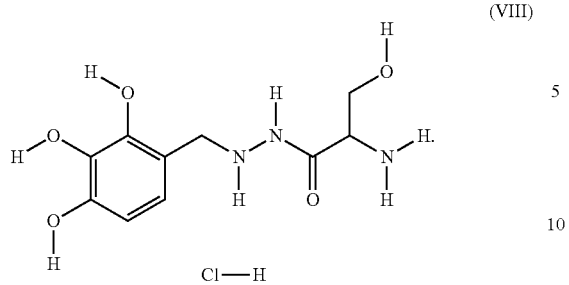

(VIII)

2. The method of claim 1, wherein L-domain motif comprises at least one of a PY-motif or a PTAP-motif.

3. The method of claim 1, wherein L-domain motif comprises at least one member selected from the group consisting of SEQ ID NOS:1-22.

4. The method of claim 1, wherein the at least one cellular polypeptide comprises an ESCRT complex protein.

5. The method of claim 4, wherein the ESCRT component protein comprises at least one member selected from a Nedd 4-related family peptide and TSG101, fragments thereof, and combinations thereof.

6. The method of claim 4, wherein ESCRT component protein comprises one of SEQ ID NOS: 24, 29, 32 and 33.

7. The method of claim 1, wherein the cell comprises a host cell for supporting active replication of the enveloped virus.

* * * * *